(12) United States Patent
Hodge et al.

(10) Patent No.: US 11,530,458 B2
(45) Date of Patent: Dec. 20, 2022

(54) METHODS OF USING MULTI-LIGAND METAL COMPLEXES TO PERFORM OXIDATIVE CATALYTIC PRETREATMENT OF LIGNOCELLULOSIC BIOMASS

(71) Applicant: Board of Trustees of Michigan State University, East Lansing, MI (US)

(72) Inventors: David B. Hodge, East Lansing, MI (US); Eric L. Hegg, East Lansing, MI (US); Zhenglun Li, Lansing, MI (US); Vaidyanathan Mathrubootham, Cary, NC (US); Aditya Bhalla, Lansing, MI (US); Namita Bansal, Lansing, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 15 days.

(21) Appl. No.: 16/206,848

(22) Filed: Nov. 30, 2018

(65) Prior Publication Data

US 2019/0091674 A1   Mar. 28, 2019

Related U.S. Application Data

(62) Division of application No. 14/729,756, filed on Jun. 3, 2015, now abandoned.

(60) Provisional application No. 62/007,306, filed on Jun. 3, 2014.

(51) Int. Cl.
| | |
|---|---|
| *C07F 1/08* | (2006.01) |
| *C13K 13/00* | (2006.01) |
| *C07F 13/00* | (2006.01) |
| *B01J 31/18* | (2006.01) |
| *D21B 1/02* | (2006.01) |
| *C13K 1/02* | (2006.01) |
| *B01J 31/22* | (2006.01) |

(52) U.S. Cl.
CPC ........... *C13K 13/002* (2013.01); *B01J 31/183* (2013.01); *B01J 31/1805* (2013.01); *B01J 31/1815* (2013.01); *B01J 31/2243* (2013.01); *C07F 1/08* (2013.01); *C07F 13/005* (2013.01); *C13K 1/02* (2013.01); *D21B 1/021* (2013.01); *B01J 2231/70* (2013.01); *B01J 2531/16* (2013.01); *B01J 2531/72* (2013.01); *B01J 2531/842* (2013.01); *B01J 2531/845* (2013.01); *C12P 2201/00* (2013.01)

(58) Field of Classification Search
None
See application file for complete search history.

(56) References Cited

U.S. PATENT DOCUMENTS

| | | |
|---|---|---|
| 4,806,475 A | 2/1989 | Gould |
| 2008/0026431 A1 | 1/2008 | Saito et al. |
| 2013/0045509 A1 | 2/2013 | Romero |
| 2015/0352540 A1 | 12/2015 | Hodge et al. |

FOREIGN PATENT DOCUMENTS

WO    2006121634 A2    11/2006

OTHER PUBLICATIONS

Li et al. (Biotechnology for Biofuels, 6, 119 (Year: 2013).*
Zhang et al. Bioresource Technology, 150, 321-327 (Year: 2013).*
Gao, et al., Comparison of Enzymatic Reactivity of Corn Stover Solids Prepared by Dilute Acid, Afex™, And Ionic Liquid Pretreatments Biotechnology for Biofuels, vol. 7, No. 71, 13 pages.
Gao, et al., Saccharification of Recalcitrant Biomass and Integration Options for Lignocellulosic Sugars from Catchlight Energy's Sugar Process (CLE Sugar) Biotechnology for Biofuels, vol. 6, No. 10, 7 pages.
Garrote, et al., Mild Autohydrolysis: An Environmentally Friendly Technology for Xylooligosaccharide Production from Wood Journal of Chemical Technology & Biotechnology, vol. 74, pp. 1101-1109.
Germer, Production of Bleachable Pulp Through Catalytic Oxygen-Alkaline Delignification of High-Yield Mechanical Pulp Tappi Journal, vol. 78, No. 11, 4 pages.
Goldstein, et al., Kinetics of Oxidation of Cuprous Complexes Of Substituted Phenanthroline and 2,2'-Bipyridyl by Molecular Oxygen and by Hydrogen Peroxide in Aqueous Solution Inorganic Chemistry, vol. 24, No. 7, pp. 1087-1092.
Goldstein, et al., Mechanisms of the Reactions of Some Copper Complexes in the Presence of DNA with O2-, H2O2, and Molecular Oxygen, 1986, vol. 108, No. 9, American Chemical Society, 2244-2250.
Gorski, et al., Fluoride-selective polymeric membrane electrodes based on Zr(IV)- and Al(III)-salen ionophores of various structures Analytica Chimica Acta, vol. 665, pp. 39-46.
Gould, et al., Alkaline Peroxide Delignification of Agricultural Residues to Enhance Enzymatic Saccharification Biotechnology and Bioengineering, vol. 26, pp. 46-52.
Gould, et al., High-Efficiency Ethanol Production from Lignocellulosic Residues Pretreated with Alkaline H2O2 Biotechnology and Bioengineering, vol. 26, pp. 628-631.
Gould, Studies on the Mechanism of Alkaline Peroxide Delignification of Agricultural Residues Biotechnology and Bioengineering, vol. 27, pp. 225-231.

(Continued)

*Primary Examiner* — Yun Qian
(74) *Attorney, Agent, or Firm* — Westman, Champlin & Koehler, P.A.; Visala C. Goswitz

(57) ABSTRACT

A homogeneous catalyst is provided comprising one or more metals; and at least two metal coordinating ligands wherein the homogeneous catalyst is a multi-ligand metal complex adapted for use with an oxidant in an oxidation reaction to catalytically pretreat lignocellulosic biomass. In one embodiment, the homogenous catalyst is copper (II) 2, 2' bipyridine ethylenediamine (Cu(bpy)en). Related methods are also disclosed.

20 Claims, 23 Drawing Sheets
(4 of 23 Drawing Sheet(s) Filed in Color)

(56) References Cited

OTHER PUBLICATIONS

Gould, et al., Treatment of Wheat Straw with Alkaline Hydrogen Peroxide in a Modified Extruder Biotechnology and Bioengineering, vol. 33, pp. 233-236.
Granholm, Desorption of Metal Ions from Kraft Pulps. Part 1. Chelation of Hardwood and Softwood Kraft Pulp with EDTA Bioresources, vol. 5, Issue 1, pp. 206-226.
Griesser, et al., Inorganic Chemistry vol. 9, No. 5, pp. 1238-1243.
Gueneau, Basile, et al., Pulp Delignification with Oxygen and Copper(II)-Polyimine Complexes Holzforschung, vol. 68, Issue 4, pp. 377-384.
Hage, et al., Applications of Transition-Metal Catalysts to Textile and Wood-Pulp Bleaching Angewandte Chemie International Edition, Dec. 23, 2005, vol. 45, Issue 2, pp. 206-222.
Hage, et al., Efficient Manganese Catalysts for Low-Temperature Bleaching, Nature, Jun. 23, 1994, vol. 369, 3 pages.
Hakola, et al., Liberation of Cellulose from the Lignin Cage: A Catalytic Pretreatment Method for the Production of Cellulosic Ethanol, ChemSusChem, Oct. 25, 2010, vol. 3, Issue 10, pp. 1142-1145 (Abstract only).
Harata, et al., Preparation, Structure and Properties Of A Copper(ii) Complex with a New Tripodal Tetradentate Ligand, Bis{(6-pivaloylamino-2-Pyridyl)methyl}{(5-carboxy-2-Pyridyl)methyl}amine (BPCA), and Reaction Of Its Cu(I) Complex with Dioxygen, Journal of Coordination Chemistry, 1998, vol. 44, pp. 311-324, OPA.
Hawkesford, et al., Functions of Macronutrients, Marschner's Mineral Nutrition of Higher Plants, Chapter 6, Third Edition, Nutritional Physiology, 2012, pp. 135-189.
Himmel, et al., Biomass Recalcitrance: Engineering Plants and Enzymes for Biofuels Production, Science, Feb. 9, 2007, vol. 315, No. 5813, pp. 804-807 (Abstract only).
Irvine, et al., The Significance of The Glass Transition of Lignin in Thermomechanical Pulping, Wood Science and Technology, 1985, vol. 19, Issue 2, pp. 139-149.
Jauneau, et al., Micro-Heterogeneity of Pectins And Calcium Distribution in the Epidermal and Cortical Parenchyma Cell Walls of Flax Hypocotyl, Protoplasma, 1997, vol. 198, Issue 1-2, pp. 9-19 (Abstract only).
Kerley, et al., Alkaline Hydrogen Peroxide Treatment Unlocks Energy in Agricultural By-Products, Science, Nov. 15, 1985, vol. 230, pp. 820-822.
Kim, et al., Enzymatic Digestion of Liquid Hot Water Pretreated Hybrid Poplar, Biotechnol Progress, Mar./Apr. 2009, vol. 25, Issue 2, pp. 340-348 (Abstract only).
Kim, et al., Solution-state 2D NMR of Ball-milled Plant Cell Wall Gels in DMSO-d6, Bioenerg. Res., 2008, vol. 1, pp. 56-66.
Kim, et al., Solution-state 2D NMR of ball-milled plant cell wall gels in DMSO-d6/pyridine-d5, Organic & Biomolecular Chemistry, 2010, vol. 8, pp. 576-591.
Kirk, et al., Enzymatic "Combustion": The Microbial Degradation of Lignin, The Annual Review of Microbiology, vol. 41, pp. 465-505.
Korpi, et al., An Efficient Method to Investigate Metal-Ligand Combinations for Oxygen Bleaching, Applied Catalyst A, General, 2004, vol. 268, pp. 199-206.
Kudrev, A G. Formation Of Mixed-Ligand Copper(II) Complexes With 2,2'-Bipyridine And An Aliphatic Diamine In Aqueous Solutions, Russian Journal Of Coordination Chemistry C/C Of Koordinatsionnaia Khimiia, Jul. 1993, vol. 19, No. 7, 4 pages.
Kumar, et al., An Improved Method to Directly Estimate Cellulase Adsorption on Biomass Solids, Enzyme and Microbial Technology, 2008, vol. 42, pp. 426-433.
Kupce, et al., Compensated Adiabatic Inversion Pulses: Broadband Inept and HSQC, Journal of Magnetic Resonance, Aug. 2007, vol. 187, Issue 2, pp. 258-265.
Kurek, et al., Oxidation of Spruce Wood Sawdust by MnO2 Plus Oxalate: A Biochemical Investigation, Journal Of Agricultural & Food Chemistry, 2000, vol. 48, No. 7, pp. 3058-3062.
Lapierre, Catherine, et al., On the Molecular Origin of the Alkali Solubility of Gramineae Lignins, Phytochemistry, 1989, vol. 28, No. 5, pp. 1401-1403.
Li, et al., Catalysis with CuII(bpy) Improves Alkaline Hydrogen Peroxide Pretreatment Biotechnology and Bioengineering, Apr. 2013, vol. 10, No. 4, pp. 1078-1086.
Li, et al., Catalytic Oxidative Pretreatment of Woody Biomass At Mild Reaction Conditions and Enzymatic Conversion to Fermentable Hydrolysate, Great Lakes Bioenergy Research Center, 1 page.
Li, et al., Catalytic Oxidative Pretreatment of Woody Biomass At Mild Reaction Conditions and Low Oxidant Loadings, 2013 AIChE Annual Meeting on Developments in the Pretreatment of Lignocellulosics for Bioconversion II, Nov. 7, 2013, 30 pages.
Li, et al., Combinatorial Modification of Multiple Lignin Traits in Trees through Multigene Cotransformation, Proceedings of the National Academy of Sciences USA, Apr. 15, 2003, vol. 100, No. 8, pp. 4939-4944.
Li, et al., Comparison of Dilute Acid and Ionic Liquid Pretreatment of Switchgrass: Biomass Recalcitrance Delignification and Enzymatic Saccharfication, Bioresource Technology, 2010, vol. 101, pp. 4900-4906.
Li, et al., Effect of Transition Metal Catalyst On Alkaline Hydrogen Peroxide Pretreatment, AIChE National Conference, Minneapolis, Session: Developments In the Pretreatment of Lignocellulosics for Bioconversion I, Oct. 18, 2011, 17 pages.
Li, et al., Effects of SPORL and Dilute Acid Pretreatment on Substrate Morphology, Cell Physical and Chemical Wall Structures, and Subsequent Enzymatic Hydrolysis of Lodgepole Pine, Applied Biochemistry and Biotechnology, 2012, vol. 168, pp. 1556-1557.
Li, et al., Identification of Features Associated with Plant Cell Wall Recalcitrance to Pretreatment by Alkaline Hydrogen Peroxide in Diverse Bioenergy Feedstocks Using Glycome Profiling, RSC Advances, 2014, vol. 4, pp. 17282-17292.
Li, et al., Improved Pretreatment with Cu(bpy)-Catalyzed Oxidation, DOE Great Lakes Bioenergy Research Center, Michigan State University, May 2, 2013, pp. 1-23.
Li, et al., Lignin Monomer Composition affects *Arabidopsis* Cell-Wall Degradability after Liquid Hot Water Pretreatment, Biotechnology for Biofuels, 2010, vol. 3, No. 27, 7 pages.
Li, et al., Lignin Structural Changes Associated with Oxidative Pretreatment Catalyzed by Cu-Diimine Complexes, DOE Great Lakes Bioenergy Research Center, Michigan State University, Oct. 30, 2012, pp. 1-12.
Li, et al., Pretreatment of Hybrid Poplar with Cu(bpy)-Catalyzed Alkaline Hydrogen Peroxide, DOE Great lakes Bioenergy Research Center, Michigan State University, pp. 1-18.
Li, et al., Project 2.2.6: Improving Alkaline Peroxide Pretreatment of Biomass Using Metal Catalysts, DOE Great Lakes Bioenergy Research Center, Nov. 20, 2012, pp. 1-22.
Li, et al., Rapid and Effective Oxidative Pretreatment of Woody Biomass at Mild Reaction Conditions and Low Oxidant Loadings, Biotechnology for Biofuels, 2013, vol. 6, No. 119, 9 pages.
Li, et al., Structural Characterization of Alkaline Hydrogen Peroxide Pretreated Grasses Exhibiting Diverse Lignin Phenotypes, Biotechnology for Biofuels, 2012, vol. 5, No. 38, 15 pages.
Official Methods of Analysis of the Association of Official Analytical Chemists, 1990, 15th Edition, vol. 1, 5 pages.
AOAC Official Method Nov. 2001, Protein (Crude) in Animal Feed, Forage (Plant Tissue), Grain, and Oilseeds: Block Digestion Method Using Copper catalyst and Steam Distillation into Boric Acid, Apr. 2, 2011, 3 pages.
Final Office Action received for U.S. Appl. No. 14/729,756, dated Sep. 14, 2017, 26 pages.
Non Final Office Action received for U.S. Appl. No. 14/729,756, dated Aug. 2, 2018, 27 pages.
Non Final Office Action received for U.S. Appl. No. 14/729,756, dated Nov. 18, 2016, 14 pages.
Restriction Requirement received for U.S. Appl. No. 14/729,756, dated Oct. 12, 2016, 9 pages.
Afshar, et al., Stoichiometric and Catalytic Secondary O-Atom Transfer by Fe(III)-NO2 Complexes Derived from a Planar Tetradentate Non-heme Ligand: Reminiscence of Heme Chemistry, Inorganic Chemistry, 2006, 8 pages, vol. 45, No. 25.

(56) References Cited

OTHER PUBLICATIONS

Albersheim, et al., A Method for the Analysis of Sugars in Plant Cell-Wall Polysaccharides by Gas-Liquid Chromatography, Carbohyd. Res., 1967, 6 pages.

Allen, et al., A Comparison of Aqueous and Dilute-Acid Single-Temperature Pretreatment of Yellow Poplar Sawdust, Ind. Eng. Chem. Res., 2001, American Chemical Society, pp. 2352-2361, vol. 40, No. 10.

Alves, et al., Comparative Studies on Oxidation of Lignin Model Compounds with Hydrogen Peroxide using Mn(IV)-Me3TACN and Mn(IV)-Me4DTNE as Catalyst, Journal of Molecular Catalysis A: Chemical, 2003, pp. 37-51, Elsevier B.V.

Antonkine, et al., Paramagnetic 1H NMR Spectroscopy of the Reduced, Unbound Photosystem I Subunit PsaC: Sequence-specific Assignment of Contact-shifted Resonances and Identification of Mixed- and Equal-valence Fe-fe Pairs In [4Fe-4S] Centers FA- And FB-, J. Biol. Inorg. Chem., Jun. 5, 2000, pp. 381-392, vol. 3.

Arantes et al., Peculiarities of Brown-Rot Fungi and Biochemical Fenton Reaction with Regard to Their Potential as a Model for Bioprocessing Biomass, Applied Microbiology and Biotechnology, Mar. 2012, pp. 323-338, vol. 94, Springer-Verlag.

Araujo et al., A Model System to Study the Lignification Process in Eucalyptus Globulus, Biochemistry and Metabolism, Sep. 2014, 3 pages, vol. 152, Issue 1, Scandinavian Plant Physiology Society.

Argyropoulos et al., Nitrogen-Centered Activators of Peroxide-Reinforced Oxygen Delignification, Ind. Eng. Chem. Res., 2004, pp. 1200-1205, vol. 43, American Chemical Society.

Atik et al., Mass Balance of Silica in Straw From the Perspective Of Silica Reduction In Straw Pulp, BioResources, 2012, pp. 3274-3282, vol. 7, No. 3.

Azarpira et al., Catalytic Alkaline Oxidation of Lignin and its Model Compounds: A Pathway to Aromatic Biochemical, Bioenerg. Res., 2014, pp. 78-86, vol. 7, Springer.

Banerjee et al., Alkaline Peroxide Pretreatment of Corn Stover: Effects of Biomass, Peroxide, and Enzyme Loading and Composition on Yields of Glucose and Xylose, Biotechnology for Biofuels, 2011, 15 pages, vol. 4, No. 16.

Banerjee et al., Scale-Up and Integration of Alkaline Hydrogen Peroxide Pretreatment, Enzymatic Hydrolysis, and Ethanolic Fermentation, Biotechnology and Bioengineering, Apr. 2012, 10 pages, vol. 109, No. 4, Wiley Periodicals, Inc.

Barber, Photosystem II: The Engine of Life, Feb. 2003, pp. 71-89, vol. 36, No. 1.

Barnes et al., Macro and Trace Mineral Content of Selected South Texas Deer Forages, Journal of Range Management, May 1990, 4 pages, vol. 43, No. 3.

Barnes et al., Synthesis of Novel Bis(amides) by Means of Triphenyl Phosphite Intermediate, Journal of Chemical and Engineering Data, 1978, 2 pages, vol. 23, No. 4, American Chemical Society.

Barnett et al., A Soluble Copper-Bipyridine Water-Oxidation Electrocatalyst, Nature Chemistry, 2012, pp. 498-502, vol. 4.

Berglund et al., Spatial Distribution of Metal Ions in Spruce Wood by Synchrotron Radiation Microbeam X-Ray Fluorescence Analysis, Jun. 2005, pp. 474-480, vol. 53, Issue 5.

Bhalla et al., Improved Lignocellulose Conversion to Biofuels with Thermophilic Bacteria and Thermostable Enzymes, Bioresour. Technol., Jan. 2013, pp. 751-759, vol. 128.

BonawitZ et al., The Genetics of Lignin Biosynthesis: Connecting Genotype to Phenotype, Annu. Rev. Genet., 2010, pp. 337-363, vol. 44.

Bose et al., Lignin Content Versus Syringyl to Guaiacyl Ratio Amongst Poplars, 2008.

Broadley et al., Function of Nutrients: Micronutrients, Chapter 7, 2012, 58 pages, Elsevier Ltd.

Chang et al., Oxidative Lime Pretreatment of High-Lignin Biomass: Poplar Wood and Newspaper, Appl. Biochem. Biotechnol., Apr. 2001, pp. 1-28, vol. 94, No. 1.

Chang et al., Species Variation in Lignin: Effects of Species on the Rate of Kraft Delignification, Mar. 1973, 3 pages, vol. 56, No. 3.

Chang et al., Fundamental Factors Affecting Biomass Enzymatic Reactivity, Mar. 2000, pp. 5-37, vol. 84-86, Issue 1-9.

Chaudhuri et al., Electricity Generation by Direct Oxidation of Glucose in Mediatorless Microbial Fuel Cells, Oct. 2003, pp. 1229-1232, vol. 21, No. 10 (Abstract only).

Chen et al., The Improvement of Polysaccharide Hydrolysis in Lignocellulosic Biomass by Catalytic Hydrogen Peroxide Pretreatment, Great Lakes Bioenergy, 2012, 1 page.

Chundawat et al., Multi-scale Visualization and Characterization of Lignocellulosic Plant Cell Wall Deconstruction During Thermochemical Pretreatment, Energy & Environmental Science, Energy Environ. Sci., 2011, pp. 973-984, vol. 4, The Royal Society of Chemistry.

Cobbett et al., Phytochelatins and Metallothioneins: Roles in Heavy Metal Detoxification and Homeostasis, Annu. Rev. Plant Biol, 2002, pp. 159-182, vol. 53.

Cortright et al., Hydrogen from Catalytic Reforming of Biomass-Derived Hydrocarbons in Liquid Water, Nature, Aug. 29, 2002, 4 pages, vol. 418, Nature Publishing Group.

Dale et al., Energy Consumption, Wealth, and Biofuels: Helping Human Beings Achieve their Potential, Biofuels, Bioprod, Bioref, 2012, 3 pages, vol. 6, Society of Chemical Industry and John Wiley & Sons, Ltd.

Das et al., Production of Pure Cellulose from Kraft Pulp by A Totally Chlorine-Free Process Using Catalyzed Hydrogen Peroxide, Aug. 2013, pp. 844-850, vol. 49.

Davison, et al., Plant Cell Walls: Basics of Structure, Chemistry, Accessibility and the Influence on Conversion, pp. 23-38.

DeMartini, et al., Investigating Plant Cell Wall Components That Effect Biomass Recalcitrance in Poplar and Switchgrass, Energy & Environmental Science, 2013, vol. 6, pp. 898-909, The Royal Society of Chemistry.

Dignum, et al., Vanilla Production: Technological, Chemical, and Biosynthetic Aspects, Food Reviews International, 2001, vol. 17, Issue 2, pp. 119-120.

Ding, et al., How Does Plant Cell Wall Nanoscale Architecture Correlate with Enzymatic Digestibility?, Science, Nov. 23, 2012, vol. 338, pp. 1055-1060.

Donaldson, Delamination of Wood at the Microscopic Scale: Current Knowledge and Methods, Delamination in Wood, Wood Products and Wood-Based Composites, Oct. 20, 2010, pp. 123-144.

Donohoe, et al., Surface and Ultrastructural Characterization of Raw And Pretreated Switchgrass, Bioresource Technology, Dec. 2011, vol. 102, Issue 24, pp. 11097-11104.

Donohoe, et al., Visualizing Lignin Coalescence and Migration Through Maize Cell Walls Following Thermochemical Pretreatment, Biotechnology and Bioengineering, Dec. 1, 2008, vol. 101, Issue 5, pp. 11097-11104.

Epstein, The Anomaly of Silicon in Plant Biology, Proceedings of the National Academy of Sciences USA, Jan. 1994, vol. 91, pp. 11-17.

Fabian, Hydrolytic Reactions of Copper(II) Bipyridine Complexes, Inorganic Chemistry, 1989, p. 3805-3807, vol. 28, No. 20, American Chemical Society.

Fackler, et al., Biomimetic Pulp Bleaching with Copper Complexes and Hydroperoxides, Progress in Biotechnology, 2002, vol. 21, pp. 62-63.

Fahlen, et al., Pore and Matrix Distribution in the Fiber Wall Revealed by Atomic Force Microscopy and Image Analysis, Biomacromolecules, 2005, vol. 6, No. 1, pp. 433-438.

Foston, et al., Biomass Characterization: Recent Progress in Understanding Biomass Recalcitrance, Industrial Biotechnology, Aug. 2012, vol. 8, No. 4, pp. 191-208.

Fromma, et al., Lignin Distribution in Wood Cell Walls Determined by Tem and Backscattered SEM Techniques, Journal of Structural Biology, Jul. 2003, vol. 143, Issue 1, pp. 77-84.

Lin, et al., Application of TGA and EDX Analysis to Evaluate the Process of Preservative-Treated Woods, Journal of the Faculty of Agriculture, 2006, vol. 51, No. 2, pp. 337-344.

Liu, et al., Coupling Alkaline Pre-Extraction with Alkaline-Oxidative Post-Treatment of Corn Stover to Enhance Enzymatic Hydrolysis and Fermentability, Biotechnology for Biofuels, 2014, vol. 7, No. 48, 12 pages.

(56) References Cited

OTHER PUBLICATIONS

Liu, et al., Targeted Alterations in Iron Homeostasis Underlie Plant Defense Responses, Journal of Cell Science, vol. 120, No. 4, pp. 596-605.

Lu, et al., Naturally p-Hydroxybenzoylated Lignins in Palms, Bioenergy Research, Springer, 2015, 19 pages.

Lucas, et al., Evidence for Room Temperature Delignification of Wood Using Hydrogen Peroxide and Manganese Acetate as a Catalyst, Bioresource Technology, Sep. 2012, vol. 119, pp. 174-180.

Mansfield, et al., Designed for Deconstruction-Poplar Trees Altered in Cell Wall Lignification Improve the Efficacy of Bioethanol Production, New Phytologist, 2012, vol. 194, pp. 91-101.

Mansfield, et al., Solutions for Dissolution-Engineering Cell Walls for Deconstruction, Current Opinion in Biotechnology, Jun. 2009, vol. 20, Issue 3, pp. 286-294.

Mansfield, et al., Whole Plant Cell Wall Characterization Using Solution-State 2D NMR, Nature Protocols, 2012, vol. 7, pp. 1579-1589.

Martinez, et al., Genome, Transcriptome, and Secretome Analysis of Wood Decay Fungus *Postia placenta* Supports Unique Mechanisms of Lignocellulose Conversion, PNAS, Feb. 10, 2009, vol. 106, No. 6, pp. 1954-1959.

Marittila, et al., Practical Aspects of Immunomicroscopy on Plant Material, Modern Research and Educational Topics in Microscopy, 2007, pp. 1015-1021.

Nagendran, et al., Reduced Genomic Potential for Secreted Plant Cellwall-Degrading Enzymes in the Ectomycorrhizal Fungus *Amanita bisporigera*, Based on the Secretome of Trichoderma Reesei, Fungal Genetics and Biology, 2009, vol. 4 6, pp. 427-435.

Nakagame, et al., The Isolation, Characterization and Effect of Lignin Isolated from Steam Pretreated Douglas-Fir on the Enzymatic Hydrolysis of Cellulose, Bioresource Technology, Mar. 2011, vol. 102, pp. 4507-4517.

Odermatt, et al., A Manganese-Based Catalyst for Alkaline Peroxide Bleaching, Oxidative Delignification Chemistry, Jul. 23, 2009, vol. 785, Chapter 14, pp. 235-254.

Omori, et al., The Reactions of Alkaline Hydrogen Peroxide with Lignin Model Dimers, Wood Science and Technology, 1981, vol. 15, Issue 2, pp. 113-123 (Abstract only).

Ong, et al., Linking Plant Biology and Pretreatment: Understanding the Structure and Organization of the Plant Cell Wall and Interactions with Cellulosic Biofuel Production, Plants and BioEnergy, vol. 4, pp. 231-253.

Ovington, The Composition of Tree Leaves Forestry, pp. 22-28.

Pacek, et al., Catalytic Conversion of Sodium Lignosulfonate to Vanillin: Engineering Aspects. Part 1. Effects of Processing Conditions on Vanillin Yield and Selectivity, Industrial & Engineering Chemistry Research, 2013, vol. 52, No. 25, pp. 8361-8372.

Palonen, et al., Evaluation of Wet Oxidation Pretreatment for Enzymatic Hydrolysis of Softwood, Applied Biochemistry and Biotechnology, Apr. 2004, vol. 117, Issue 1, pp. 1-17.

Pan, et al., Bioconversion of Hybrid Poplar to Ethanol and Co-Products Using an Organosolv Fractionation Process: Optimization of Process Yields, Biotechnology and Bioengineering, Aug. 5, 2006, vol. 94, No. 5, pp. 851-861.

Paszczynski, et al., Delignification of Wood Chips and Pulps by Using Natural and Synthetic Porphyrins: Models of Fungal Decay, Applied and Environmental Microbiology, Jan. 1988, vol. 54, No. 1, pp. 62-68, American Society for Microbiology.

Pauly, et al., Plant Cell Wall Polymers as Precursors for Biofuels, Current Opinion in Plant Biology, 2010, vol. 13, pp. 305-312.

Perng, et al., Catalytic Oxygen Bleaching of Wood Pulp with Metal Porphyrin and Phthalocyanine Complexes, Tappi Journal, Nov. 1994, vol. 77, No. 11, pp. 119-125.

Pu, et al., Assessing the Molecular Structure Basis for Biomass Recalcitrance During Dilute Acid and Hydrothermal Pretreatments, Biotechnology for Biofuels, 2013, vol. 6, No. 15, 13 pages.

Rahikainen, et al., Inhibitory Effect of Lignin During Cellulose Bioconversion: The Effect of Lignin Chemistry on Non-productive Enzyme Adsorption., Bioresource Technology, Apr. 26, 2013, vol. 26, No. 133, pp. 270-278.

Rahimi, et al., Formic-Acid-Induced Depolymerization of Oxidized Lignin to Aromatics, Nature, Nov. 13, 2014, vol. 515, pp. 249-252.

Rencoret, et al., Structural Characterization of Lignin Isolated from Coconut (*Cocos nucifera*) Coir Fibers, Journal ol Agricultural and Food Chemistry, American Chemical Society, vol. 61, pp. 2434-2444.

Robinson, et al., Rapid Analysis of Poplar Lignin Monomer Composition by A Streamlined Thioacidolysis Procedure and Near-Infrared Reflectance-Based Prediction Modeling, 2009, The Plant Journal, vol. 58, pp. 706-714.

Rodsrud, History and Future of World's Most Advanced Biorefinery in Operation, Biomass and Bioenergy, vol. 46, pp. 46-59 (Abstract only).

Rovio, et al., Catalyzed Alkaline Oxidation as A Wood Fractionation Technique Bioresources, vol. 7, No. 1, pp. 756-776 (Abstract only).

Rubin, Genomics of Cellulosic Biofuels, Nature, Aug. 14, 2008, vol. 454, No. 14, pp. 841-845.

Ruffella, et al., Pretreatment and Enzymatic Hydrolysis of Recovered Fibre for Ethanol Production, Bioresource Technology, Apr. 2010, vol. 101, Issue 7, pp. 2267-2272.

Sannigrahi, et al., Poplar as a Feedstock for Biofuels: A Review of Compositional Characteristics, Biofuel Bioproducts & Biorefining, 2010, vol. 4, pp. 209-226.

Santana, et al., Silica Content of 36 Brazilian Tropical Wood Species, Holzforschung, Jan. 2013, vol. 67, Issue 1 pp. 19-24.

Santos, et al., Kinetics of Eucalypt Lignosulfonate Oxidation to Aromatic Aldehydes by Oxygen in Alkaline Medium, Industrial & Engineering Chemistry Research, 2011, vol. 50, No. 1, pp. 291-298.

Sigel, et al., On the Kinetics and Mechanism of the Decomposition of Hydrogen Peroxide, Catalyzed by the $Cu^{2+}$-2,2'-Bipyridyl Complex 1,2, Journal of the American Chemical Society, Feb. 26, 1969, p. 1061-1064, vol. 91, No. 5.

Sigel, et al., Metal Ions and Hydrogen Peroxide. Xx. On the Kinetics and Mechanism of the Decomposition of Hydrogen Peroxide, Catalyzed by the $Cu^{2+}$-2,2'-Bipyridyl Complex, Journal of the American Chemical Society, 1969, vol. 91, No. 5, pp. 1061-1064.

Simoes, et al., Ozone Delignification of Pine and Eucalyptus Kraft Pulps. 1. Kinetics, Industrial & Engineering Chemistry Research, 1999, vol. 38, No. 12, pp. 4600-4607.

Simoes, et al., Ozone Delignification of Pine and Eucalyptus Kraft Pulps. 2. Selectivity, Industrial & Engineering Chemistry Research, 1999, vol. 38, No. 12, pp. 4608-4614.

Sluiter, et al., Determination of Structural Carbohydrates and Lignin in Biomass, National Renewable Energy Laboratory, Laboratory Analytical Procedure (LAP), Apr. 25, 2008, 7 pages.

Solomon, Biofuels and Sustainability, Annals of The New York Academy of Sciences, Jan. 29, 2010, vol. 1185, pp. 119-134.

Spears, Minerals in Forages, 1994, Chapter 7, pp. 281-317.

Sperry, Evolution of Water Transport and Xylem Structure, International Journal of Plant Sciences, 2003, vol. 164, pp. S115-S127.

Stoklosa, et al., Extraction, Recovery, and Characterization of Hardwood and Grass Hemicelluloses for Integration into Biorefining Processes Inustrial & Engineering Chemical Research, vol. 51, pp. 1045-1053 (Abstract only).

Stoklosa, Fractionation and Improved Enzymatic Deconstruction of Hardwoods with Alkaline Delignification, Bioenergy Research, Jan. 2015, 9 pages.

Studer, Lignin Content in Natural Populus Variants Affects Sugar Release, PNAS, Apr. 12, 2011, 108, No. 15, pp. 6300-6305.

Sun, et al., Production and Extraction of Sugars from Switchgrass Hydrolyzed in Ionic Liquids Biotechnology for Biofuels, 2013, vol. 6, No. 39, 14 pages.

Teixeira, Alkaline and Peracetic Acid Pretreatments of Biomass for Ethanol Production Applied Biochemistry and Biotechnology, Spring 1999, vol. 77, Issue 1-3, pp. 19-34.

Thomine, et al., Iron Transport and Signaling in Plants, ResearchGate, Springer, Dec. 2010, pp. 99-131.

(56) References Cited

OTHER PUBLICATIONS

Tokareva, et al., Analysis of Wood Tissues by Time-Of-Flight Secondary Ion Mass Spectrometry, Holzforschung, Nov. 2007, vol. 61, Issue 6, pp. 647-655.
Tucker, et al., Comparison of Yellow Poplar Pretreatment Between Nrel Digester and Sunds Hydrolyzer, Applied Biochemistry and Biotechnology, 1998, vol. 70-72, pp. 25-35.
Walton, Deconstructing the Cell Wall, Plant Physiology, 1994, vol. 104, pp. 1113-1118.
Wei, et al., Elucidating the Role of Ferrous Ion Cocatalyst in Enhancing Dilute Acid Pretreatment of Lignocellulosic Biomass, Biotechnology for Biofuels, 2011, vol. 4, No. 48, 16 pages.
Werhan, et al., Acidic Oxidation of Kraft Lignin into Aromatic Monomers Catalyzed by Transition Metal Salts Holzforschung, Aug. 2011, vol. 65, Issue 5, pp. 703-709 (Abstract only).
Williams, et al., Impacts of Delignification and Hot Water Pretreatment on the Water Induced Cell Wall Swelling Behavior of Grasses and its Relation to Cellulolytic Enzyme Hydrolysis and Binding, Cellulose, 2014, vol. 21, Issue 1, pp. 221-235.
Xu, et al., A Critical Reinvestigation of the TAED-Activated Peroxide System For Low-Temperature Bleaching Of Cotton, Carbohydrate Polymers, Jan. 2013, vol. 92, No. 1, pp. 249-253.
Yang, et al., Effect of Xylan and Lignin Removal by Batch and Flowthrough Pretreatment on the Enzymatic Digestibility of Corn Stover Cellulose, Biotechnology and Bioengineering, Apr. 5, 2004, vol. 86, No. 1, pp. 88-95.
Yang, et al., Epoxidation Catalyzed by Iron(III) and Manganese(III) pyridine-2-carboxamido Complexes, Journal of Molecular Catalysis, 2007, vol. 266, pp. 284-289.
Yruela, Copper in Plants, Brazilian Journal of Plant Physiology, 2005, vol. 17, No. 1, pp. 145-156.
Yu et al., Effect of Lignin Chemistry on the Enzymatic Hydrolysis of Woody Biomass, ChemSusChem, Jul. 2014, vol. 7, Issue 7, 1942-1950.
Yue, et al., Syntheses of Lignin-Derived Thioacidolysis Monomers and their Uses as Quantitation Standards Bioresources Journal of Agricultural and Food Chemistry, 2012, vol. 60, No. 4, pp. 922-928.
Zakzeski, et al., Transition Metal Catalyzed Oxidation of Alcell Lignin, Soda Lignin, and Lignin Model Compounds in Ionic Liquids, Green Chemistry, 2010, vol. 12, No. 7, pp. 1225-1236.
Zeng, et al., Lignin Plays a Negative Role in The Biochemical Process for Producing Lignocellulosic Biofuels, Current Opinion in Biotechnology, 2014, vol. 27, pp. 38-45.
Zhang, et al., Comparison of Dilute Acid and Sulfite Pretreatment for Enzymatic Saccharification of Earlywood and Latewood of Douglas fir, BioEnergy Research, 2013, vol. 7, Issue 1, pp. 362-370.
Zhang, et al., Xylans Inhibit Enzymatic Hydrolysis of Lignocellulosic Materials by Cellulases, Bioresource Technology, Oct. 2012, vol. 121, pp. 8-12.
Zhu, et al., Pretreatment of Woody Biomass for Biofuel Production: Energy Efficiency, Technologies, and Recalcitrance, Applied Microbiology and Biotechnology, Jul. 2010, vol. 87, pp. 847-857.
Zhu, et al., Woody Biomass Pretreatment for Cellulosic Ethanol Production: Technology and Energy Consumption Evaluation, Bioresource Technology, 2010, vol. 101, pp. 4992-5002.
Araujo et al., "A Model System to Study the Lignification Process in Eucalyptus Globulus", Biochemistry and Metabolism, Sep. 2014, vol. 152, Issue 1, Scandinavian Plant Physiology Society, pp. 17-31.
Chaudhuri et al., "Electricity Generation by Direct Oxidation of Glucose in Mediatorless Microbial Fuel Cells", Nature Biotechnology, Sep. 7, 2003, vol. 21, pp. 1229-1232.
Dignum et al., "Vanilla Production: Technological, Chemical, and Biosynthetic Aspects", Food Reviews International, 2001, vol. 17, Issue 2, pp. 199-219.
Donaldson, L. "Delamination of Wood at the Microscopic Scale: Current Knowledge and Methods, Delamination in Wood", Wood Products and Wood-Based Composites, 2011, pp. 123-144.
Fackler et al., "Biomimetic Pulp Bleaching with Copper Complexes and Hydroperoxides", Progress in Biotechnology, 2002, vol. 21, pp. 61-62.
Goldstein et al., "Kinetics of Oxidation of Cuprous Complexes Of Substituted Phenanthroline and 2,2'-Bipyridyl by Molecular Oxygen and by Hydrogen Peroxide in Aqueous Solution", Inorganic Chemistry, 1985, vol. 24, No. 7, pp. 1087-1092.
Hage et al.,"Applications of Transition-Metal Catalysts to Textile and Wood-Pulp Bleaching", Angewandte Chemie, Dec. 23, 2005, vol. 45, Issue 2, pp. 206-222.
Hakola et al. "Liberation of Cellulose from the Lignin Cage: A Catalytic Pretreatment Method for the Production of Cellulosic Ethanol", Chemsuschem, Oct. 25, 2010, vol. 3, Issue 10, pp. 1142-1145.
Himmel et al., "Biomass Recalcitrance: Engineering Plants and Enzymes for Biofuels Production", Science, Feb. 9, 2007, vol. 315, No. 5813, pp. 804-807.
Irvine, G. "The Significance of The Glass Transition of Lignin in Thermomechanical Pulping", Wood Science and Technology, 1985, vol. 19, Issue 2, pp. 139-149.
Jauneau et al., "Micro-Heterogeneity of Pectins And Calcium Distribution in the Epidermal and Cortical Parenchyma Cell Walls of Flax Hypocotyl", Protoplasma, 1997, vol. 198, Issue 1-2, pp. 9-19.
Kim et al., "Enzymatic Digestion of Liquid Hot Water Pretreated Hybrid Poplar", Biotechnol Progress, 2009, vol. 25, Issue 2, pp. 340-348.
Li et al., "Identification of Features Associated with Plant Cell Wall Recalcitrance to Pretreatment by Alkaline Hydrogen Peroxide in Diverse Bioenergy Feedstocks Using Glycome Profiling", RSC Advances, Mar. 2014, vol. 4, pp. 17282-17292.
Omori et al., "The Reactions of Alkaline Hydrogen Peroxide with Lignin Model Dimers: Part 1: Phenacyl a-Aryl Ethers", Wood Science and Technology, 1981, vol. 15, Issue 2, pp. 67-79.
Rodsrud et al., "History and Future of World's Most Advanced Biorefinery in Operation", Biomass and Bioenergy, Nov. 2012, vol. 46, pp. 46-59.
Rovio et al., "Catalyzed Alkaline Oxidation as A Wood Fractionation Technique", Bioresources, 2012, vol. 7, No. 1, pp. 756-776.
Solomon, B. "Biofuels and Sustainability", Annals Of The New York Academy of Sciences, Jan. 24, 2010, vol. 1185, pp. 119-134.
Stoklosa et al., "Extraction, Recovery, and Characterization of Hardwood and Grass Hemicelluloses for Integration into Biorefining Processes", Industrial & Engineering Chemical Research, Aug. 3, 2012, vol. 51, pp. 11045-11053.
Werhan et al., "Acidic Oxidation of Kraft Lignin into Aromatic Monomers Catalyzed by Transition Metal Salts", Holzforschung, Aug. 2011, vol. 65, Issue 5, pp. 703-709.

* cited by examiner (i) Cell Corner (ii) Secondary Cell Wall (iii) Metal Nanoparticle (iv) Metal Nanoparticle

S
Syringyl

S′
Syringyl

G
Guaiacyl

G′
Guaiacyl

VA
Vanillate

PB
*p*-Hydroxybenzoate

X2
Bensaldehyde end-groups

X1
Cinnamaldehyde end-groups

B
Phenylcoumaran (β-5)

C
Resinol (β-β)

A′
β-aryl ether (β-O-4)

A
β-aryl ether (β-O-4)

| Lignin Stream | |
|---|---|
| Composition | % |
| *Lignin* | 90 |
| Xylan | 3 |
| Glucan | 0 |
| Ash Content | 2 |

METHODS OF USING MULTI-LIGAND METAL COMPLEXES TO PERFORM OXIDATIVE CATALYTIC PRETREATMENT OF LIGNOCELLULOSIC BIOMASS

This application is a divisional of U.S. patent application Ser. No. 14/729,756 filed on Jun. 30, 2015, which application claims benefit under 35 U.S.C. 119 (e) of U.S. Provisional Application Ser. No. 62/007,306 filed on Jun. 3, 2014, which applications are hereby incorporated by reference in their entireties.

STATEMENT OF GOVERNMENT RIGHTS

This invention was made with government support under DE-FC02-07ER64494 awarded by the U.S. Department of Energy. The government has certain rights in the invention.

BACKGROUND

Cellulosic biofuels offer enormous potential as sustainable, low-carbon alternative liquid transportation fuels to petroleum-derived fuels. The vast majority of carbon in the terrestrial biosphere is contained in the cell walls of plants or lignocellulose. This enormous reservoir of reduced carbon is largely untapped for conversion to fuels, chemicals, and polymers as consequence of the difficulty in deconstructing the biopolymers contained in the plant cell wall matrix to suite a chemicals that are amenable to conversion processes.

SUMMARY

The various embodiments described herein provide multi-ligand metal complexes and methods of using same to perform oxidative catalytic pretreatment of lignocellulosic biomass. In one embodiment, the multi-ligand metal complex is a multi-ligand copper complex. In one embodiment, the copper complex is a copper(II) 2,2'-bipyridine complex (Cu(bpy)) modified to contain at least one additional metal-coordinating ligand. In a particular embodiment, copper(II) 2,2' bipyridine ethylenediamine (Cu(bpy)en) is used.

In various embodiments, the oxidant is added gradually, rather than in batch. In one embodiment, an integrated conversion process for lignocellulosic biomass that produces bio-based chemicals and fuels, is provided. In one embodiment, these processes depend, in part, on particular chemical structures contained in plant cell macromolecules. In one embodiment, plant biomass having more than trace amounts of one or more transition metals (e.g., Cu, Fe and/or Mn) is used.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE EMBODIMENTS

Figure 1:
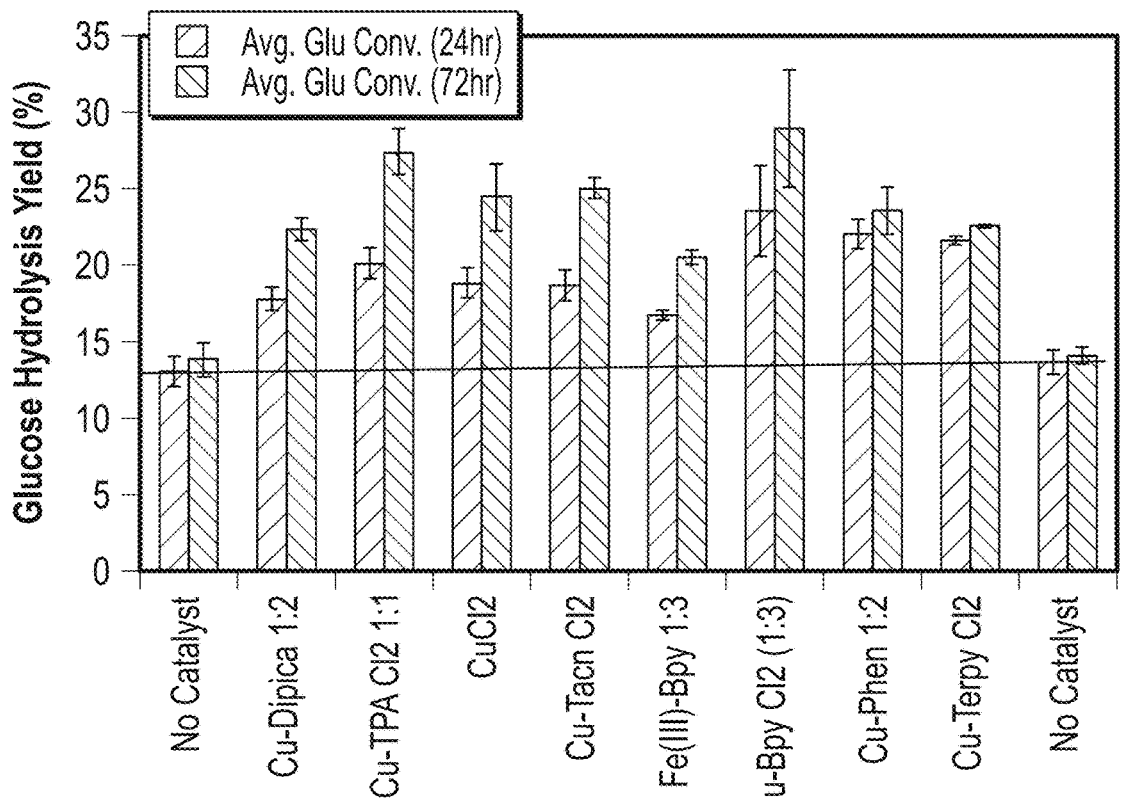
FIG. 1 is a graph showing the effect of metal catalyst addition to a 24 hr AOP pretreatment of hybrid poplar according to an embodiment.

In the following detailed description, embodiments are described in sufficient detail to enable those skilled in the art to practice them, and it is to be understood that other embodiments may be used and that chemical and procedural changes may be made without departing from the spirit and scope of the present subject matter. The following detailed description is, therefore, not to be taken in a limiting sense, and the scope of embodiments of the present invention is defined only by the appended claims.

The term "biomass" as used herein, refers in general to organic matter harvested or collected from a renewable biological resource as a source of energy and bioproducts. The renewable biological resource can include plant materials, animal materials, and/or materials produced biologically. The term "biomass" is not considered to include fossil fuels, which are not renewable.

The term "plant biomass" or "ligno-cellulosic biomass (LCB)" as used herein is intended to refer to virtually any plant-derived organic matter containing cellulose and/or hemicellulose as its primary carbohydrates (woody or non-woody) available for producing energy on a renewable basis and bioproducts. Plant biomass can include, but is not limited to, agricultural residues such as corn stover, wheat straw, rice straw, sugar cane bagasse, sorghum and the like. Plant biomass can also include agricultural residues and forest residues that are dedicated for bioenergy purposes, such as residues of grasses and trees. Plant biomass further includes, but is not limited to, "woody biomass", i.e., woody energy crops, wood wastes and residues such as trees, including fruit trees, such as fruit-bearing trees, (e.g., apple trees, orange trees, and the like), softwood forest thinnings, barky wastes, sawdust, paper and pulp industry waste streams, wood fiber, and the like. Additionally perennial grass crops, such as various prairie grasses, including prairie cord grass, switchgrass, *Miscanthus*, big bluestem, little bluestem, side oats grama, and the like, have potential to be produced large-scale as additional plant biomass sources. For urban areas, potential plant biomass feedstock includes yard waste (e.g., grass clippings, leaves, tree clippings, brush, etc.) and vegetable processing waste. Plant biomass is known to be the most prevalent form of carbohydrate available in nature and corn stover is currently the largest source of readily available plant biomass in the United States. When describing the various embodiments and used without a qualifier, the term "biomass" is intended to refer to "plant biomass," i.e., lignocellulosic biomass (LCB) containing plant cell wall polysaccharides.

The term "biofuel" as used herein, refers to any renewable solid, liquid or gaseous fuel produced biologically and/or chemically, for example, those derived from biomass. Most biofuels are originally derived from biological processes such as the photosynthesis process and can therefore be considered a solar or chemical energy source. Some types of biofuels, such as some types of biodiesel, can be derived from animal fats. Other biofuels, such as natural polymers (e.g., chitin or certain sources of microbial cellulose), are not synthesized during photosynthesis, but can nonetheless be considered a biofuel because they are biodegradable. There are generally considered to be three types of biofuels derived from biomass synthesized during photosynthesis, namely, agricultural biofuels (defined below), municipal solid waste biofuels (residential and light commercial garbage or refuse, with most of the recyclable materials such as glass and metal removed) and forestry biofuels (e.g., trees, waste or byproduct streams from wood products, wood fiber, pulp and paper industries). Biofuels produced from biomass not synthesized during photosynthesis include, but are not limited to, those derived from chitin, which is a chemically modified form of cellulose known as an N-acetyl glucosamine polymer. Chitin is a significant component of the waste produced by the aquaculture industry because it comprises the shells of seafood.

The term "agricultural biofuel", as used herein, refers to a biofuel derived from agricultural crops, lignocellulosic crop residues, grain processing facility wastes (e.g., wheat/oat hulls, corn/bean fines, out-of-specification materials, etc.), livestock production facility waste (e.g., manure, carcasses, etc.), livestock processing facility waste (e.g., undesirable parts, cleansing streams, contaminated materials, etc.), food processing facility waste (e.g., separated waste streams such as grease, fat, stems, shells, intermediate process residue, rinse/cleansing streams, etc.), value-added agricultural facility byproducts (e.g., distiller's wet grain (DWG) and syrup from ethanol production facilities, etc.), and the like. Examples of livestock industries include, but are not limited to, beef, pork, turkey, chicken, egg and dairy facilities. Examples of agricultural crops include, but are not limited to, any type of non-woody plant (e.g., cotton), grains such as corn, wheat, soybeans, sorghum, barley, oats, rye, and the like, herbs (e.g., peanuts), short rotation herbaceous crops such as switchgrass, alfalfa, and so forth.

The term "pretreatment step" as used herein, refers to any step intended to alter native biomass so it can be more efficiently and economically converted to reactive intermediate chemical compounds such as sugars, organic acids, etc., which can then be further processed to a variety of end products such as ethanol, isobutanol, long chain alkanes etc. Pretreatment can reduce the degree of crystallinity of a polymeric substrate, reduce the interference of lignin with biomass conversion, and hydrolyze some of the structural carbohydrates, thus increasing their enzymatic digestibility and accelerating the degradation of biomass to useful products. Pretreatment methods can utilize acids of varying concentrations, including dilute acid pretreatments, concentrated acid pretreatments (using, for example, sulfuric acids, hydrochloric acids, organic acids, and the like) and/or pretreatments with alkali such as ammonia and/or ammonium hydroxide and/or calcium hydroxide and/or sodium hydroxide and/or lime, and the like, and/or oxidative pretreatments using oxidants such as air, oxygen, hydrogen peroxide, organic peroxide, ozone, and the like.

Pretreatment methods can additionally or alternatively utilize hydrothermal treatments including water, heat, steam or pressurized steam pretreatments, including, but not limited to, hydro-thermolysis pretreatment and liquid hot water pretreatment, further including, for example, acid catalyzed steam explosion pretreatment (e.g., $SO_2$ catalyzed). Pretreatment can occur or be deployed in various types of containers, reactors (e.g., batch, counter-current, and the like), pipes, flow through cells and the like. Many pretreatment methods will cause the partial or full solubilization and/or destabilization of lignin and/or hydrolysis of hemicellulose to pentose sugars. Further examples of pretreatment include, but are not limited wet oxidation, organosolv pretreatment and mechanical extrusion.

The term "alkaline oxidative pretreatment" as used herein refers to a pretreatment process in which plant biomass is pretreated under alkaline conditions using oxidative chemicals, which can include, but are not limited to, hydrogen peroxide, oxygen, ozone, hydroperoxide anion, superoxide radical, hydroxyl radical, and peroxy acids (e.g., peracetic acid, peroxymonosulfuric acid, peroxyphosphoric acid, meta-chloroperoxybenzoic acid). See, for example, Liu, et al., *Coupling alkaline pre-extraction with alkaline-oxidative post-treatment of corn stover to enhance enzymatic hydrolysis and fermentability*, Biotechnology for Biofuels, 2014, 7:48, which describes example conditions for alkaline oxidative pretreatment. An alkaline oxidative pretreatment which uses hydrogen peroxide as the oxidant is to be distinguished from a conventional "alkaline hydrogen peroxide (AHP)" pretreatment which is a one-step catalytic pretreatment process which requires much higher oxidant loadings. See, for example, Biotechnol Bioeng 1984, 26:46-52; Biotechnol Bioeng 1984, 26:628-631; Biotechnol Bioeng 1985, 27:225-231; Science 1985, 230:820-822 and Biotechnol Biofuels 2011, 4:16, which describe conventional AHP with much higher oxidant loadings.

The term "metal-ligand complex" as used herein refers to a metal complex containing one or more metal-coordinating ligands and one or more metal atoms which are in a state of interaction with each other. Such interactions include various types of forces and bonds, which include, but are not limited to, ionic bonds, covalent bonds, and van der Waals forces.

The term "metal-coordinating ligand" as used herein refers to a ligand, such as an ion, a molecule, or the like, that is capable of interacting with the metal portion of a metal-ligand complex. When used without qualification, the term "ligand" is intended to refer to a "metal-coordinating ligand."

The term "copper-coordinating ligand" as used herein refers to a metal coordinating ligand capable of interacting with copper atoms or copper ions.

The term "single-ligand metal complex" as used herein refers to a metal-ligand complex containing only one ligand that coordinates with, i.e., interacts with metal atoms or metal ions.

The term "multi-ligand metal complex" as used herein refers to a metal-ligand complex containing more than one ligand that coordinates with, i.e., interacts with metal atom or metal ions.

The term "toxicity" as used herein refers to ions, molecules and metal-ligand complexes present in the process streams during biomass conversion and cellulosic biofuel production that negatively impact the yield of the products.

The term "slow add" as used herein refers to a gradual rate of addition of a reagent to a reaction vessel. The gradual rate can be continuous or discontinuous, i.e., can include intermittent periods of no reagent being added. A "slow add" is in contrast to a batch method of adding a reagent, in which all the desired reagent is added to the reactive vessel at once.

The term "state of interaction" as used herein refers to an interaction between a ligand and a metal or between a metal and multiple ligands. Such an interaction can include various types of forces and bonds, which include, but are not limited to, ionic bonds, covalent bonds, and van der Waals forces.

Nearly all forms of lignocellulosic biomass, i.e., plant biomass, such as monocots, comprise three primary chemical fractions: hemicellulose, cellulose, and lignin. Lignin, which is a polymer of phenolic molecules, provides structural integrity to plants, and is difficult to hydrolyze. As such, after sugars in the biomass have been fermented to a bioproduct, such as alcohol, lignin remains as residual material, i.e., a non-easily digestible portion.

Cellulosic biofuel production from lignocellulosic biomass has gained considerable momentum due to both environmental and social sustainability benefits. However, the technology is not yet fully commercialized. One issue impeding cellulosic biofuel production using the sugar platform is the hydrolysis-resistant nature of certain components in the lignocellulosic biomass.

Cellulose and hemicelluloses in plant cell walls exist in complex structures within the residual material. Hemicellulose is a polymer of short, highly-branched chains of mostly five-carbon pentose sugars (xylose and arabinose), and to a lesser extent six-carbon hexose sugars (galactose, glucose and mannose). Because of its branched structure, hemicellulose is amorphous and relatively easy to hydrolyze into its individual constituent sugars by enzyme or dilute acid treatment. Cellulose is a linear polymer comprising of $\beta(1\rightarrow 4)$ linked D-glucose in plant cell wall, much like starch with a linear/branched polymer comprising of $\alpha(1\rightarrow 4)$ linked D-glucose, which is the primary substrate of corn grain in dry grind and wet mill ethanol plants. However, unlike starch, the glucose sugars of cellulose are strung together by β-glycosidic linkages which allow cellulose to form closely-associated linear chains. Because of the high degree of hydrogen bonding that can occur between cellulose chains, cellulose forms a rigid crystalline structure that is highly stable and much more resistant to hydrolysis by chemical or enzymatic attack than starch or hemicellulose polymers. Although hemicellulose sugars represent the "low-hanging" fruit for conversion to a biofuel, the substantially higher content of cellulose represents the greater potential for maximizing biofuel yields, on a per ton basis of plant biomass.

Lignocellulose can also be characterized as a highly heterogeneous composite material comprised of multiple cell wall biopolymers (cellulose, heteropolysaccharides including hemicelluloses and pectins, and lignins) associated primarily by non-covalent interactions which are assembled into cell walls with composition and properties varying by cell and tissue type. These components are interconnected through a variety of covalent and noncovalent interactions, giving rise to a highly organized network which is assembled in a tightly controlled sequence during plant growth. This heterogeneous higher order structure of the cell wall impacts the cell wall's response to deconstruction and conversion.

Plant cell walls exhibit substantial heterogeneity in both content and distribution of the inorganic elements which also have implications for biomass conversion processes. This includes differences between content and distribution of inorganics in disparate plant taxa, differences between related species, within a single species as a function of its phenotype and environment, and even between tissues in a single plant.

Inorganic elements in plants are known to be responsible for diverse roles, including maintenance of ionic equilibrium in cells (e.g., K) and storage (e.g., Fe in ferritin), which, despite being localized in plastids, is water-extractable. A subset of the inorganic elements in plants is strongly associated with the cell wall. These elements are more resistant to aqueous extraction and include inorganic elements that may have structural roles, including, but not limited to, Ca and B ionic cross-links in pectic polysaccharides, calcium oxalate raphide crystals in some grasses, and Si in the cell walls of grasses which can comprise a significant fraction of the mass of a plant. Another lass of role of cell-wall associated inorganic elements are metal co-factors in enzymes (e.g., Zn, Fe, Mn, Cu).

Redox-active metals, such as Cu, Mn, Fe, can exist in multiple oxidation states in vivo and are often involved in reactions involving electron transfer. Specifically, Fe in plants is associated with Fe-heme proteins and iron-sulfur (Fe—S) clusters in proteins, such as ferredoxins, which function as electron carriers in the photosynthetic electron transport chain. Cu in plants has diverse roles as a structural element in regulatory proteins, in photosynthetic electron transport, mitochondrial respiration, and Fe mobilization, among others. Metals may also be associated with metallothioneins (MTs) and phytochelatins (PCs), which are cysteine-rich polypeptides involved in either ameliorating the toxicity or controlling homeostasis of metals such as Fe, Ni, Cd, Zn, and Cu by coordination by thiols. In addition to its involvement with enzymes associated with the shikimic acid pathway and lignin biosynthesis, Mn is contained in a metallo-oxo cluster containing 4 Mn ions at differing oxidation states in the oxygen evolving complex of photosystem II.

There are differences in the strength and nature of association of cell wall-associated metals. Specifically, Mn may be strongly associated with the cell wall and be s present in "organic chelates" or "bound to lignin." Alkali delignified hardwoods are known to have differences in the extractability of cell wall-associated Mn versus Fe using chelating compounds. Mg, which is a component of chlorophyll, is useful for photosynthesis and protein synthesis, although a portion of Mg may be bound to pectin or precipitated as salts in the vacuole, while the remainder is extractable with water. During either oxidative delignification or biomass conversion processes where oxygen may be present, cell wall-associated transition metals can catalyze the formation of reactive oxygen species through Fenton chemistry. This catalytic activation of oxygen by transition metals has been shown to contribute to the oxidative scission of polysaccharides during alkaline-oxidative bleaching or delignification using $H_2O_2$ or $O_2$. As a result, precautions are taken during these processes through chelation and washing steps to remove metals and addition Mg salts and silicates to complex transition metals during these unit operations.

Therefore, a pretreatment process is typically used to alter and open up the cell wall matrix, to hydrolyze the hemicelluloses, and to alter the hemicelluloses. Pretreatment disrupts the non-easily digestible portion of lignocellulosic biomass, e.g., cellulose and lignin, thus improving its accessibility. After pretreatment, much of the biomass becomes easily digestible, while a portion remains non-easily digestible. Ultimately, the pretreatment process makes the cellulose more accessible (during a subsequent hydrolysis process, such as with lytic enzymes) for conversion of the lignocellulose polysaccharides (e.g., cellulose and hemicellulose) to monomeric sugars, which can be transformed to target products via catalytic conversion or microbial fermentation.

However, enzymatic hydrolysis of lignocellulose polysaccharides is usually hindered by the natural resistance of plant cell wall against deconstruction. To overcome this resistance, pretreatment processes of biomass feedstock have been developed and employed. Biomass pretreatment modifies cell wall structure and renders the biomass more digestible by enzymes.

A wide range of pretreatments are known, but few pretreatment methods have been identified as effective for biomass feedstocks, such as woody biomass, which are highly resistant to enzymatic hydrolysis. For example, enzymatic hydrolysis of hybrid poplar wood usually produces sugars at only 5 to 30% of the theoretical maximum yield. As noted above, such resistance involves the structural rigidity of the plant cell wall, the crystallinity of cellulose, and the presence of lignin, which remains as a residual material.

However, in the embodiments described herein, the alkaline pretreatments not only solubilize the lignin, it is expected that the lignin produced may closely resemble native lignin, such that less than 35% of the α-carbon of the solubilized lignin is oxidized from a hydroxyl to a carbonyl.

Lignin is known to be useful in a variety of applications including, but not limited to, carbon fiber composites, bio-oil, resins, adhesive binders and coating, plastics, paints, enriching soil organic carbon, fertilizer, rubbers and elastomers, paints, antimicrobial agents and slow nitrogen release fertilizer, and the like, and can be a substitute for polymers produced using crude oil.

One current source of lignin in the market is produced from sulfite (or sulfonate) based paper/pulp mills, a kraft pulping process, and the like. Most such mills currently burn the lignin to recover energy, in an attempt to reduce the environmental impact of discharge. Very few sulfite mills currently process the lignosulfonates from sulfite spent liquors. Additionally, the quality and quantity of lignin obtained via currently known methods are inadequate for most applications. As such, methods to fractionate and convert lignin into value-added products is needed.

Known methods for pretreating plant biomass are typically performed under elevated pressures and temperatures (above room temperature). Such methods include hot water and steam treatments, ammonia treatments and sulfite treatments.

Other pretreatment methods utilize an oxidant-based pretreatment, such as the alkaline oxidative pretreatment process defined herein or a conventional alkaline hydrogen peroxide (AOP) known by those skilled in the art. Yet other methods include catalytic processes. Catalytic approaches to plant cell wall deconstruction and conversion of insoluble biomass rely on homogeneous catalysts to allow the catalyst to diffuse through nano-scale pores within the cell walls to perform the desired reactions. Heterogeneous catalysis is known to be inefficient unless the cell walls are solubilized in expensive solvents such as ionic liquids. In one embodiment, homogeneous catalysts are used in many applications, such as homogeneous copper catalysts used for atom transfer radical polymerization where catalyst removal to prevent contamination of the product adds cost to the process.

Use of a single ligand copper complex as a catalyst in combination with an alkaline oxidative pretreatment (AOP) process is known. See, for example, Li et al., *Rapid and Effective Oxidative Pretreatment of Woody Biomass at Mild Reaction Conditions and Low Oxidant Loadings* Biotechnol Biofuels 6(1), 119 (2013), and Li, et al., Catalysis with $Cu^{II}$(bpy) Improves Alkaline Hydrogen Peroxide Pretreatment. Biotechnol Bioeng. 110(4):1078-1086 (2013), each of which is incorporated by reference in its entirety. However, the amount of oxidant required in such processes is high, such as at least 10% of the weight of the biomass to be treated. Additionally, in order to achieve suitable pretreatment results, the amount of metal utilized in a single-ligand copper complex is high (e.g., more than 50 μmol of metal complexes per gram of biomass to be pretreated). Use of such high levels of a metal can pose toxicity issues in subsequent processes (e.g., fermentation). Moreover, use of such high amounts of metals and oxidants can be cost prohibitive.

As such, the various embodiments described herein provide a multi-ligand metal complex for use in an oxidative pretreatment process, such as an alkaline oxidative (AOP) process, which not only allows for a reduction in the amount of metals used in the process, but also a reduction in the amount of oxidant. In one embodiment, the multi-ligand metal complex is used with a conventional alkaline hydrogen peroxide (AOP) process. In one embodiment, the multi-ligand metal complex is a multi-ligand copper complex. In one embodiment, the copper complex is a copper(II) 2,2'-bipyridine complex (Cu(bpy)) modified to contain at least one additional metal-coordinating ligand, such as pyridine; 1,10-phenanthroline; ethylenediamene; histidine; and/or glycine.

While not wishing to be bound by this proposed theory, both the single- and multi-ligand metal complexes are thought to function as suitable catalysts for lignocellulosic biomass (i.e., cause sufficient catalyst sorption into the biomass) due to the ability of the cationic metal, such as copper, to interact with (e.g., bond with) charged anionic groups, such as deprotonated phenolic hydroxyls in lignin, carboxylate groups in lignin, and/or uronic acids in pectins and hemicelluloses.

In one embodiment, the pH of the plant biomass being pretreated is adjusted to increase the number of deprotonated groups. In one embodiment, the pH of the pretreated biomass is, or the biomass is pH adjusted to achieve, a neutral pH during the pretreatment process. In one embodiment, the pH is adjusted to achieve an alkaline pH to deprotonate the phenolic groups in lignin and to increase lignin solubility. In one embodiment, the pH is adjust to at least 11, such as at least 11.5, including any value in between. In some embodiments, elevation of the pH is achieved with bases such as ammonia and/or ammonia derivatives, such as amines, in which copper is stabilized in solution in the form of a complex ion. In one embodiment, the pH is adjusted via addition of a base, which can react with lignin and cause depolymerization and/or solubilization, i.e., helps the plant cell wall to become degraded and/or destroyed, thus reducing resistance to subsequent hydrolysis.

In one embodiment, oxidants useful in an oxidative pretreatment process include, but are not limited to, air, oxygen, hydrogen peroxide, ozone, persulfate, percarbonate and sodium peroxide. In one embodiment, the metal-coordinating ligands include 2,2'-bipyridine and at least one of another metal-coordinating ligand, including, but not limited to nitrogen-donating ligands such as pyridine, 1,10-phenanthroline, and ethylenediamine, and ligands containing both a nitrogen donor and a carboxylate group such as the amino acids including histidine or glycine. In one embodiment, the catalytic metal element(s) (i.e., metal or metals) in the catalyst can include, but are not limited to, aluminum, zinc, nickel, magnesium, manganese, iron, copper cobalt and/or vanadium in various oxidation states. In one embodiment, the elements include, but are not limited to, iron (e.g., Fe(II), Fe(III)), copper (e.g., Cu(I), Cu(II)), cobalt (e.g., Co(III), Co(VI)), and/or vanadium (e.g., V(II), V(III), V(IV), V(V)).

By substituting an amount of the 2,2'-bipyridine (bpy) with other, lower costs ligands, substantial savings can be achieved. In one embodiment, about 1 weight/weight (w/w) % up to about 99% or higher, such as 100% of bpy is substituted, such as about 10 to about 90%, such as about 20 to about 80%, such as about 35% to about 60%, including any range there between. In the various embodiments described herein, the multi-ligand metal complexes have low production costs. In one embodiment, substitution of bpy with other metal coordinating ligands provides a savings on the order of 10-fold or more, such as a savings of about 20 to 30 times the cost of using bpy alone.

An additional benefit relates to reduced microbial toxicity. Microbial toxicity is characterized by the final growth of yeast cells during yeast fermentation, and/or the growth rate of yeast during fermentation, and/or the length of the lag phase during fermentation. Such toxicity is caused by metal ions and other chemicals present in the processing stream, including the metals present in the multi-ligand catalyst and metal elements present in the plant biomass itself. Since the various embodiments allow for a reduced amount of metal as compared to conventional processes, the yeast used downstream is less adversely affected down to minimally adversely affected. As such, in one embodiment, the multi-ligand complexes have minimal microbial toxicity towards yeast fermentation (i.e., less than 50% reduction in final growth of yeast cells, as quantified with optical density).

In one embodiment, the final growth of yeast cells during yeast fermentation is decreased by 50% or less as the result of the presence of multi-ligand metal complexes, which indicates the low toxicity of the multi-ligand metal complexes. In one embodiment, the final growth of yeast cells is decreased by less than 40 to 50%, less than 30 to 50%, less than 20 to 50%, less than 10 to 50%, less than 5 to 50%, including any range or value there between. Additionally, the various embodiments provide for a pretreatment method which produces pretreated biomass which is easily digestible by commercial cellulase cocktails into fermentable sugars (glucose, xylose, etc.)

Use of the multi-ligand metal complexes described herein also reduces the amount of metal, such as copper, used in the process as compared to a single ligand metal complex, such as a single ligand copper complex, by at least 50%, or at least 40%, or at least 30% or at least 20% or at least 10% or at least 5% or lower, including any range therein. Use of a reduced amount of metal not only reduces toxicity levels, but further reduces costs.

Use of the multi-ligand metal complex may reduce the amount of oxidant, such as hydrogen peroxide, used in the oxidative pretreatment by at least 90%, by at least 80%, by at least 70%, by at least 60%, by at least 50%, or at least 40%, or at least 30% or at least 20% or at least 10% or at least 5% or lower, including any range therein. Use of a reduced amount of oxidant further reduces costs.

In one embodiment, one or more oxidants are combined with the other reactants at a low weight percent (%) loading on biomass (w/w), i.e., loading of no more than 15%. In one embodiment, the oxidant loading is less than 10%, such as less than 5%. In one embodiment, the oxidant loading ranges from about 1% to about 15%, such as about 1% to about 10%, such as about 1% to 5% or less, including any range there between. Such loadings are lower than conventional loadings which can be as high as 200%. In one embodiment, at least 0.1% to about 50 (w/w) %, such as greater than 31.5% oxidant is added, such as from about 31.51% to about 50 (w/w) %. In one embodiment, at least 2.5% to about 50 (w/w) %, such as greater than 31.5% hydrogen peroxide is added, such as from about 31.51% to about 50 (w/w) %.

In one embodiment, use of the multi-ligand metal complex as a catalyst during an oxidative pretreatment may allow the pretreatment process to proceed significantly faster (e.g., at least two times as fast) as compared with an oxidative pretreatment performed using a conventional single ligand metal complex as a catalyst.

In one embodiment, the oxidant is added at a "slow add" rate. In one embodiment, the "slow add" rate is equal to or less than a rate of consumption of the oxidant by the other reactants. Use of a slow rate, surprisingly, results in increased effectiveness of the pretreatment, as evidenced by increased downstream yields of various sugars.

Any suitable plant biomass can be used. In one embodiment, the plant biomass contains transition metals. Use of a plant biomass containing more than trace amounts of one or more transition metals results in further cost savings, as a reduced amount of catalyst is needed to affect the same or substantially the same results. Examples of plant biomass containing more than trace amounts of transition metals include, but are not limited to, hardwoods of the genus *Populus* (e.g., various types of poplar including hybrid poplar, hybrid aspen, western balsam poplar, and the like), birch (including silver birch and the like), maple (including sugar maple and the like), further including grasses (including, but not limited to, corn, switchgrass, sorghum, *miscanthus*) and gymnosperms, which are also referred to as conifers and softwoods (including, but not limited to, the genus of *Pinus*, such as *Pinus resinosa*, i.e., red pine).

In one embodiment, the plant biomass contains one or more transition metals that a redox-active, including, but not limited to, Fe, Mn, Cr, Co, Ni, Cu, Mo, Pd, Ru, Re, Pt, Pd, Os, Ir and combinations thereof.

In one embodiment, prior to being subjected to a catalyzed pretreatment process the plant biomass is first subjected to an extraction step designed to facilitate oxidative pretreatment and biomass hydrolysis.

In various embodiments, the biomass may be subjected to a cycle of hydrolysis (e.g., enzymatic, acid, etc.) using any conventional methods known in the art. In one embodiment, a reduced amount of enzymes is used, as compared to hydrolysis of conventionally catalyzed pretreated biomass.

In various embodiments, hydrolysis may optionally be followed by or integrated with either fermentation or sugar catalytic conversion of sugars to bioproducts, such as biofuels, biochemicals and biopolymers. Use of the multi-ligand metal complex as described herein provides improved downstream bioproduct yields, such as sugar yields, as compared to yields obtained with a single-ligand metal complexes, such as single-ligand copper complexes. In one embodiment, such yields may be improved by at least 5% or higher, such as at least 10%, at least 20%, at least 30%, at least 40% at least 50% or higher, up to two or three times higher, including any range there between.

In one embodiment, the process can further include recovery and reuse of the multi-ligand metal complex, including recovery of the metal itself. Conventional technologies for metal removal (e.g., copper) from wastewater streams are based on ion exchange, precipitation/co-precipitation plus filtration, and membrane separation. Additionally, lignocellulose such as waste biomass or biomass fractions, such as lignin, have been proposed as biosorbant materials in the treatment of wastewater to remove heavy metals, including copper. Cationic metals can sorb to charged anionic groups such as deprotonated phenolic hydroxyls in lignin or carboxylate groups in lignin or uronic acids in pectins and hemicellulose and are known to be strongly affected by pH with more deprotonated groups at elevated pH.

In one embodiment, catalyst sorption to biomass is strongly pH-dependent with near-complete catalyst adsorption to biomass at alkaline pH and substantial desorption at neutral to acidic pH. In one embodiment, pH is adjusted to recover the multi ligand metal complex. In one embodiment, untreated plant biomass is used as an adsorbent to both recover the catalyst and impregnate the catalyst into the untreated plant biomass (such as woody biomass, including, but not limited to, poplar, hybrid polar, and other trees).

In one embodiment, any conventional method is used to recover the catalyst from either the unhydrolyzed pretreated biomass (often referred to as "pretreatment liquor") and/or the clarified (cell-free) stillage following fermentation and distillation. Such methods include, but are not limited to flocculation, precipitation, and filtration using a polyanionic flocculant (e.g., Betz-Dearborn MR2405 or Ondeo-Nalco 8702) which is commercially employed to remove heavy metals during wastewater treatment. Such methods can further include recovery by adsorption to a commercial ion exchange resin (e.g., Amberlyst™ 40Wet) which is used industrially to recover and recycle copper catalyst used in the production of adipic acid. In one embodiment, the catalyst is recovered and recycled.

In embodiments which include a sugar conversion step, recovery and reuse of the multi-ligand metal complex provides the additional benefit of further reducing toxicity during subsequent sugar conversion steps. Recovering and recycling the multi-ligand metal complex further helps to reduce costs.

In one embodiment, the process may produce monomeric aromatic compounds, such as, syringic acid, vanillin, syringaldehyde acid, vanillic acid. Such aromatic compounds are useful in a number of applications, such as food additives, polymer precursors, and various types of chemicals.

In one embodiment, the process may produce aliphatic acids, including, but not limited to formic acid, oxalic acid, acetic acid, lactic acid, succinic acid, azaleic acid. Such aromatic compounds are useful in a number of applications, such as food additives, polymer precursors, and fine chemicals.

The various embodiments will be further described by reference to the following examples, which are offered to further illustrate various embodiments. It should be understood, however, that many variations and modifications may be made while remaining within the scope of the various embodiments.

Example 1

Screening with Metal Ligand Complexes

Screening of various metal ligand complexes (hereinafter "catalysts") was performed via catalytic alkaline oxidative pretreatment (AOP) of alkali-extracted switchgrass (AESG). To prepare AESG, 80 grams of untreated switchgrass (*Panicum virgatum*, cv. Cave-In-Rock, hammer milled to pass a 5-mm screen, and stored at a moisture content of approximately 5%) was soaked in an aqueous solution of 5 g/L NaOH at 80° C. for 2 hrs. The weight-to-volume (w/v) solids loading of switchgrass during alkaline extraction was 10% (e.g., 10 g of biomass in 100 mL NaOH solution). After the alkaline extraction, the residual solid biomass was recovered via filtration through a 200-mesh steel cloth and washed with deionized water until the washing effluent had a neutral pH. The washed solids was recovered as AESG and air-dried for over 7 days.

Fe(III)-phthalocyanine (95%), Fe(III)-tetraphenylporphyrin (≥97%) and Fe(III)-tetrakis-pentafluorophenyl)-porphyrin (≥9%) catalysts were purchased from Sigma-Aldrich and used without further purification. [Al(III)(3,5-$^t$Bu$_2$-salophen)Cl] [3,5-$^t$Bu$_2$-salophen=N,N'-bis(3,5-di-tert-butylsalicylidene)-1,2-phenylenediamine], [Zn(II)(BPPA)Cl]Cl [BPPA=N,N-bis(6-pivaloylamido-2-pyridylmethyl)-N-(2-pyridylmethyl)amine], and [NEt$_4$][Fe(III)(bpb)Cl$_2$] [H$_2$(bpb)=N,N-bis(2-pyridinecarboxamide)-1,2-benzene] catalysts were synthesized according to the methods described in (Górski et al. *Analytica Chimica Acta* 2010, 665, 39; Harata et al. *Journal of Coordination Chemistry* 1998, 44, 311; Barnes et al. *Journal of Chemical & Engineering Data* 1978, 23, 349; Afshar et al. *Inorganic Chemistry* 2006, 45, 10347; Yang et al. *Journal of Molecular Catalysis A: Chemical* 2007, 266, 284), which are hereby incorporated by reference in their entireties, and verified by NMR (Agilent Direct Drive 2, 500 MHz) and/or UV-Vis spectral analysis (Hewlett Packard 8453 UV/Vis spectrophotometer). The Cu(bpy) catalyst was prepared in an aqueous solution by mixing cupric sulfate pentahydrate (Mallinckrodt, 99.8%) and 2,2'-bipyridine at a ligand:metal molar ratio (L/M) of 3:1.

To study the effect of catalytic AOP pretreatment on AESG, pretreatment was performed in a 100 g/L aqueous suspension of AESG in the presence of each catalyst. The loading of hydrogen peroxide (J. T. Baker, ACS reagent, as in an about 30 to about 32% w/v aqueous solution) on biomass is approximately 10% by weight. The concentration of each catalyst in the aqueous suspension of AESG is shown in Table 1. The reaction mixture contained 0.04 M Na$_2$HPO$_4$—NaOH buffer (prepared using disodium phosphate and sodium hydroxide) to maintain the pH at 11.5 during pretreatment. After 24 hrs of incubation at 30° C. without mixing, the pretreated switchgrass slurry was washed using deionized water to remove the alkaline phosphate buffer.

The enzymatic digestibility of AOP-pretreated switchgrass was estimated by the yield of glucose during the enzymatic hydrolysis of AOP pretreated AESG. The percentage yield was calculated on the basis of the glucan content in AESG prior to catalytic AOP pretreatment. The theoretical maximum hydrolysis yield was lower than 100% due to the loss of sugars in the washing step between catalytic AOP pretreatment and enzymatic hydrolysis.

For enzymatic hydrolysis, 500 μL of 1 M Na-citrate buffer (pH 5) and 40 μL of 10 mM tetracycline (Sigma-Aldrich) were added to AOP-AESG that was not dried after catalytic AOP pretreatment. Accellerase 1500 (42 FPU/mL; Danisco-Genencor, Palo Alto, Calif.) was added at 50 mg protein per gram of glucan in AESG. The total volume of the mixture (solid and liquid) was adjusted with deionized water to reach a 5% (w/v) solids concentration, and the samples were incubated at 50° C. during hydrolysis.

The efficacy of catalysts on AOP pretreatment of AESG is shown in Table 1. AOP pretreatment of AESG at pH 11.5 was not improved via addition of metal catalysts, except for the case of Cu (bpy) catalyst, which gave a very moderate improvement in the enzymatic digestibility of AOP pretreated AESG. See Table 1 below.

TABLE 1

Efficacy of ligand-metal catalyst addition to a 24 hour (hr) AOP Pretreatment of AESG

| Catalyst | Catalyst concentration (mM) | pH | Glucose yield of enzymatic hydrolysis (% of theoretical maximum) | |
|---|---|---|---|---|
| | | | 24 hrs | 72 hrs |
| No catalyst | — | 3 | 30.06 ± 1.96 | 36.12 ± 2.33 |
| | | 9 | 32.37 ± 1.2 | 37.97 ± 0.57 |
| | | 10 | 31.25 ± 0.16 | 38.77 ± 0.28 |
| | | 11 | 37.74 ± 0.33 | 42.70 ± 0.59 |
| | | 13 | 36.82 ± 1.23 | N.D. |
| Fe(III)-phthalocyanine | 0.05 | 3 | 30.91 ± 0.24 | 36.80 ± 2.84 |
| | | 11 | 34.21 ± 0.23 | 38.75 ± 1.52 |
| Fe(III)-tetraphenylporphyrin | 0.05 | 3 | 31.55 ± 1.6 | 42.13 ± 1.89 |
| | | 11 | 36.98 ± 1.3 | 42.14 ± 0.63 |
| Fe(III)-tetrakis-pentafluorophenyl)-porphyrin | 0.05 | 3 | 29.18 ± 0.33 | 35.38 ± 0.43 |
| | | 11 | 35.37 ± 0.45 | 40.25 ± 0.19 |
| [NEt$_4$][Fe(III)(bpb)Cl$_2$] | 2 | 9 | 27.07 ± 0.6 | 34.27 ± 0.21 |
| | | 10 | 25.54 ± 0.21 | 31.97 ± 0.13 |
| | | 11 | 27.44 ± 1.54 | 31.54 ± 0.23 |
| [Al(III)(3,5-$^t$Bu$_2$-salophen)Cl] | 2 | 10 | 28.90 ± 0.17 | N.D. |
| | | 11 | 29.80 ± 0.25 | N.D. |
| | | 13 | 34.19 ± 0.41 | N.D. |
| [Zn$^{II}$(BPPA)Cl]Cl | 2 | 10 | 26.43 ± 0.31 | N.D. |
| | | 11 | 27.33 ± 0.62 | N.D. |
| | | 13 | 33.36 ± 0.3 | N.D. |
| Cu(bpy), L/M = 3:1 | 5 | 10 | 38.67 ± 0.3 | 42.98 ± 0.88 |
| | | 11 | 41.65 ± 0.14 | 44.97 ± 0.42 |
| | | 13 | 41.56 ± 0.06 | 43.95 ± 0.17 |

(N.D.: not determined)

Example 2

Catalyst Screening with Multi-Ligand Metal Complexes

Metal complexes (hereinafter "metal catalysts") containing multiple or single metal coordinating ligands were tested. The metal catalysts tested included copper catalysts having a second metal coordinating ligand substituted for at least a portion of the 2,2'-bipyridine. These catalysts were evaluated for their performance in further enhancing the efficacy of AOP pretreatment of hybrid poplar. Ligands involved in the screening included histidine, glycine, di(2-picolyl)amine (dipica, 97%), 1,4,7-triazacyclononane (TACN, 95%), 2,2';6',2"-terpyridine (Terpy, 98%), 1,10-phenanthroline (phen, ≥99%), and tris(2-pyridylmethyl) amine (TPA, 98%, obtained from Sigma-Aldrich and Acros Organics/0). An iron 2,2'-bipyridine complex was prepared by mixing ferrous sulfate heptahydrate with 2,2'-bipyridine in an aqueous solution, and this iron complex was also tested.

The hybrid poplar (Populus nigra var. charkoviensis× caudina cv. NE-19) used in this testing was grown at the University of Wisconsin Arlington Agricultural Research Station. The hybrid poplar was harvested in 2011 and debarked using methods known in the art at the University of Wisconsin, Madison to produce heartwood and sap wood (different parts of the wood stem which can be differentiated via chemical testing).

The enzymatic digestibility of hybrid poplar after pretreatment with AOP and metal complexes involving above mentioned ligands was used to evaluate the performance of various multi-ligand metal complexes (See FIG. 1). As these results show, various types of multi-ligand metal complexes, as well as a single-ligand iron complex are capable of enhancing oxidative pretreatment of hybrid poplar. However, Cu(bpy) complexes demonstrated superior performance among all candidates, and was selected for further testing.

Example 3

Alkaline Extraction, Catalytic Pretreatment and Enzymatic Hydrolysis of Hybrid Poplar About 0.5 g of hybrid poplar, i.e., poplar (from the same source as described in Example 2) was extracted in a temperature controlled rotary shaker (New Brunswick Scientific Classic Series C24KC, 210 rpm) at 30° C. in a 5 mL aqueous solution containing 270 mM NaOH (J. T. Baker, ACS reagent, 98.8%) for approximately 1 hr to produce extracted wet poplar. The extracted wet poplar was washed with 5 mL deionized water and centrifuged (Thermo Scientific Sorvall ST-16R) at 1000 rpm for 1 min to separate the solid and liquid phases. (The alkaline liquid from the washing was used in later examples for the extraction step).

The separated solid phase of the extracted wet poplar was then subjected to a catalytic AOP pretreatment in a 5 mL aqueous solution containing 10.8 g/L NaOH, 10 g/L hydrogen peroxide and a conventional single-ligand copper diimine catalyst at varying concentrations of copper (0.5, 1, 2, 3, 4, and 5 mM) and varying concentrations of 2,2'-bipyridine (1, 2, 4, 6, 8, 10, 15 and 20 mM) to produce incubated catalyzed pretreated (solid phase) poplar (hereinafter "solid poplar slurry"). The results presented herein are for concentrations of 2 mM of copper and 4 mM of 2,2'-bipyridine.

Enzymatic hydrolysis was performed on the solid poplar slurry at 50° C. in the same rotary shaker used for the extraction step. In preparation for hydrolysis, 20 µL of 72% (w/w) $H_2SO_4$ and 500 µL of 1 M sodium citrate buffer (pH 5) (prepared from sodium citrate and citric acid) were added to the solid poplar slurry to adjust the pH to 5 (optimum pH for the enzymes being used herein). Thereafter, 40 µL of 10 mM tetracycline (Sigma-Aldrich) stock solution was added to the solid poplar slurry to inhibit microbial growth. This step was followed by addition of a Cellic CTec2 and HTec2 (Novozymes A/S, Bagsværd, DK) enzyme cocktail at a loading of 30 mg protein/g glucan in the biomass prior to extraction and catalytic pretreatment, unless otherwise noted. The enzymatic reaction (50° C., 210 rpm, 72 hrs) was carried out at 5% solids concentration by adjusting the volume of the poplar slurry to 10 mL via the addition of deionized water.

Following enzymatic hydrolysis, the resulting solid and liquid phases were separated by centrifugation in same manner as in Example 2, to produce separated hydrolyzed solid and liquid phases. The amount of glucose and xylose released into the aqueous phase was quantified by High Performance Liquid Chromatography (HPLC) (Agilent 1260 Series equipped with an Aminex® HPX-87H column operating at 65° C., a mobile phase of 0.05 M $H_2SO_4$, and a flow rate of 0.6 mL per minute, and detection by refractive index). The yield of glucose and xylose released was defined as the amount of solubilized monosaccharide divided by the total sugar content of the poplar biomass prior to incubation and catalytic pretreatment as determined by chemical composition analysis.

After the enzymatic hydrolysis of the solid poplar slurry, over 80% of the polysaccharides (by weight) in the poplar biomass were converted to fermentable sugars. This sugar yield was significantly higher than the sugar yield produced using untreated raw hybrid poplar. (See FIG. 2).

Example 4

Recovery of Copper Catalyst, and Catalyst Impregnation During Alkaline Extraction About 40 g hybrid poplar (same source as Example 2) was catalytically pretreated with 400 mL of aqueous solution containing 2 mM copper sulfate, 4 mM 2,2'-bipyridine, 270 mM NaOH and 10% (w/w) hydrogen peroxide loading on biomass at 30° C. for 24 hrs to produce catalytically pretreated poplar slurry (hereinafter "poplar slurry"). Following the pretreatment, a copper removal step was performed to remove part or all of the copper present in the poplar slurry for use again in the process.

The copper removal step used in this testing was a desorption step in which the pH of the poplar slurry was adjusted to 5 with 1.6 mL of 72% sulfuric acid (prepared via dilution of 98% sulfuric acid, J. T. Baker) to produce a pH-adjusted poplar slurry. The pH-adjusted poplar slurry was then incubated for approximately 1 hr in the same rotary shaker as Example 2 at 30° C., with 120 rpm shaking speed to produce pH-adjusted poplar slurry. After incubation, the residual solid poplar was separated from the aqueous phase via centrifugation in the same manner as described in Example 3. The separated solids were then converted to sugars via enzymatic hydrolysis following the procedures described in Example 3.

The separated aqueous phase or pretreatment liquor (PTL) produced following centrifugation containing the copper catalyst (containing about 0.9 mM of coordinated copper complexes) was collected and used again in another catalytic AOP pretreatment. In this testing, about 0.5 g of hybrid poplar (same source as in Example 2) was incubated in the rotary shaker (120 rpm) with a mixture of 4.73 mL of the previously collected aqueous phase and 270 µL of 5 M NaOH (J. T. Baker, ACS reagent, 98.8%) at 30° C. for about 1 hr to produce a catalyst-impregnated wet poplar slurry. The catalyst-impregnated wet poplar slurry was thereafter washed with 5 mL deionized water and centrifuged in the same manner as Example 2 to separate the solid and liquid phases.

Figure 3:
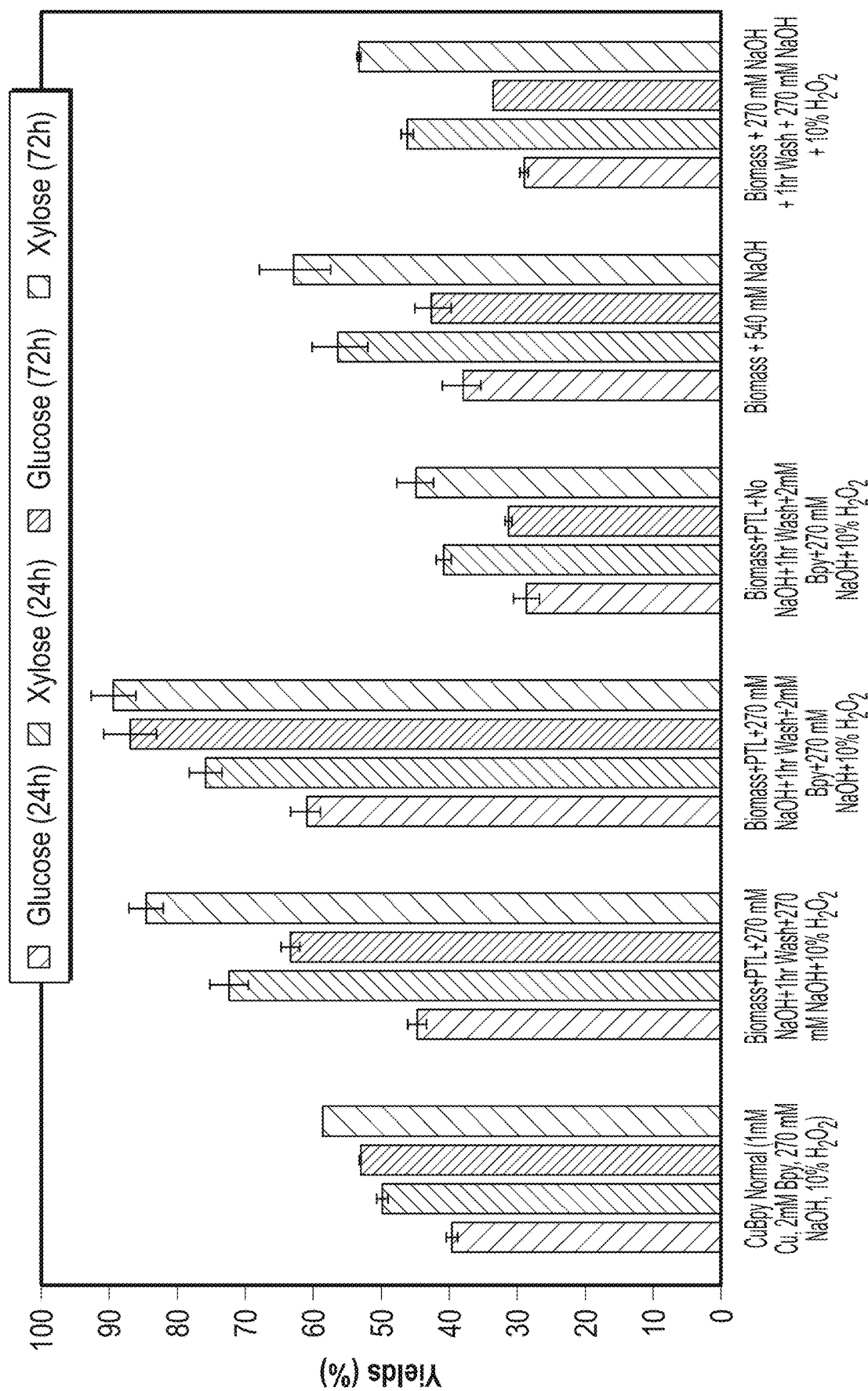
FIG. 3 is a graph showing use of recovered catalyst in catalytic AOP according to an embodiment.

After another centrifugal solid-liquid separation (performed in same manner as described in Example 3), the separated solid phase of the incubated wet poplar biomass was catalytically pretreated with 5 mL aqueous solution containing 2 mM 2,2'-bipyridine, 270 mM NaOH and hydrogen peroxide (sources of chemicals used are as described in Example 3) at 30° C. for approximately 24 hrs. After the catalytic pretreatment, the biomass slurry was hydrolyzed by enzymes to obtain fermentable sugars at high yields (≥80% of the theoretical maximum). See FIG. 3.

Example 5

Production of Aromatic Chemicals Via Catalytic Oxidative Pretreatment

About 0.5 g hybrid poplar (same source as Example 2) was catalytically pretreated with 5 mL of an aqueous solution containing 2 mM copper sulfate, 4 mM 2,2'-bipyridine, 270 mM NaOH and 10% (w/w) hydrogen peroxide loading on biomass at 30° C. for approximately 24 hrs to produce a catalytically pretreated poplar slurry (sources of chemicals used are as described in Example 3). The solid and liquid phases were separated as described in the above examples.

For LC-MS analysis of the monomeric aromatic compound content, 10 µL of undiluted pretreatment liquor sample were injected into a XEVO G2SQTOF mass spectrometer in combination with a Waters Acquity® Ultra Performance Liquid Chromatograph (UPLC) system, which was equipped with an ESI interface capable of operating in both positive- and negative-ion modes. Chromatographic separation was carried out on a Thermo BetaBasic 100×2.1 mm C18 column (Thermo Fisher Scientific, Waltham, Mass., USA) maintained at 40° C. The binary solvent gradient comprised 0.1% formic acid in water (solvent A) and 100% methanol (solvent B) in the following gradient: 95% solvent A for the first 3 min, 50% solvent A over the next 1 min, 30% solvent A over next 2 min, and 5% solvent A over the final 2 min. The column was then returned to 95% solvent A, and equilibrated for 2 min prior to the next injection. A solvent delay of 2 min was used to prevent saturation of the detector with the sample solvent. The negative-ion mode mass spectrometry conditions were constant during all experiments with a voltage of −2.25 kV and a desolvation temperature of 350° C.

MassLynx™ software (Waters) version 4.1 was used for system control and data acquisition. The raw data was processed using the TargetLynx™ application. Pure standards for vanillin, vanillic acid, acetovanillone, syringaldehyde, syringic acid, acetosyringone, and p-hydroxybenzoate (Sigma-Aldrich, St. Louis, Mo., USA) were used to validate peak compound identification and for quantitation.

Figure 4A:
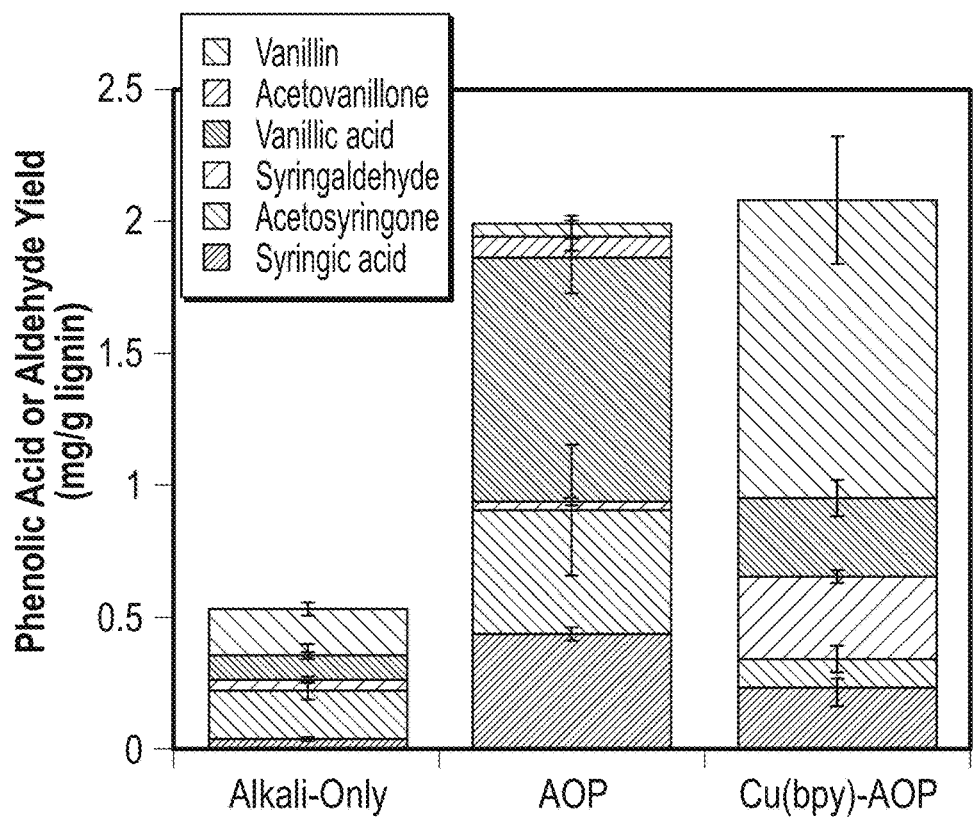
FIG. 4A is a graph showing phenolic acid and aldehyde yields during various pretreatments of hybrid poplar according to an embodiment.
Figure 4B:
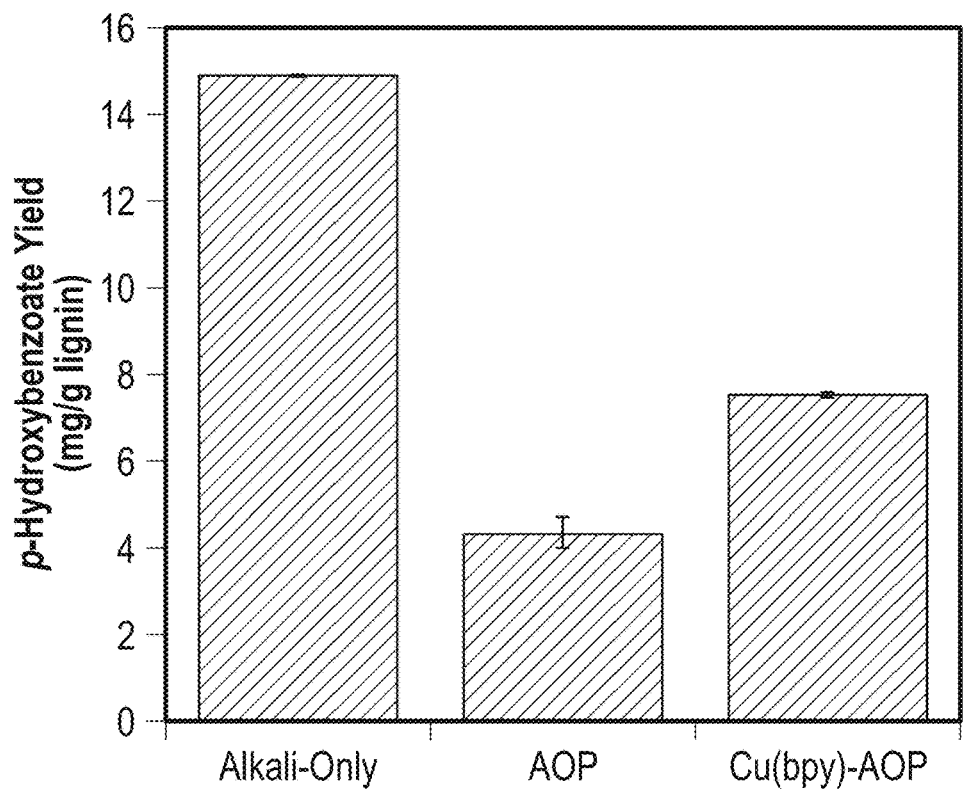
FIG. 4B is a graph showing p-hydroxybenzoate yield during various pretreatments of hybrid poplar according to an embodiment.

For quantitation of p-hydroxybenzoate, samples were prepared following the same procedure used for the LC-MS analysis, with the samples instead analyzed via high-performance liquid chromatography (HPLC) (Agilent 1260 LC equipped with an Agilent Poroshell 120 EC-C18 column (4.6×50 mm) and a diode array detector (DAD). Integration of the p-hydroxybenzoate peak at 280 nm and comparison to a standard curve was used for quantitation. A binary isocratic solvent system was utilized consisting of 80:20 solvent C to solvent D, where solvent C is acetonitrile with 0.1% water, and solvent D is acetonitrile with 0.1% trifluoroacetic acid. The results are shown in FIGS. 4A and 4B.

Example 6

Catalytic Pretreatment of Hybrid Poplar Biomass Using Copper (II) 2,2'-Bipyridine Ethylenediamine (Cu(Bpy)En)

Hybrid poplar (0.5 g) (same source as Example 2) was catalytically pretreated using 1 mM of a stock solution of multi-ligand copper complex, namely copper (II) 2,2' bipyridine ethylenediamine (Cu(bpy)en) containing 40 mM copper sulphate pentahydrate, 40 mM bipyridine and 40 mM ethylenediamine in deionized water, together with 270 mM NaOH and 10% $H_2O_2$ loading (w/w) on biomass in a total 5 mL volume made with deionized water. Other components of the pretreatment catalyst include tetraacetylethylenediamine (TAED), ethylenediaminetetraacetic acid (EDTA), manganese sulfate, and magnesium sulfate. The catalytic pretreatment was allowed to proceed for approximately 24 hrs at 30° C.

Thereafter, the resulting poplar slurry was pH adjusted to 5 and hydrolyzed according to the process described in Example 3. Following enzymatic hydrolysis, the solid and liquid phases were separated by centrifugation as described in Example 3.

Among all catalyst systems tested, Cu (bpy)en yielded higher glucose yields compared to other catalyst systems tested. Also, by utilizing ½ the concentration of copper and ¼ the concentration of (bpy), as compared with a conventional Cu(bpy) catalyst, the overall cost is reduced. See Table 2 below.

TABLE 2

Catalyst and Glucose Conversions

| Catalyst | Glucose |
| --- | --- |
| $Cu(bpy)_2$ | 55.76 |
| Cu(bpy)TAED | 55.01 |
| Cu(bpy)en (1 mM) | 55.00 |
| Cu(bpy)en (2 mM) | 48.15 |
| $Cu(bpy)MnSO_4$ | 46.78 |
| $CuSO_4$ | 40.62 |
| $Mn(TAED)_2$ | 38.65 |
| $Cu(en)_2$ | 34.22 |
| $Cu(TAED)_2$ | 30.72 |
| $MgSO_4$ | 25.17 |
| Mg(bpy) | 25.09 |
| $Mn(en)_2$ | 24.08 |
| $Mn(EDTA)_2$ | 22.28 |
| $Mn(bpy)_2$ | 21.21 |
| Control | 11.34 |

Example 7

Copper Recovery, Recycling and Extractives Removal Following Catalytic AOP Pretreatment Catalytic AOP Pretreatment In one set of tests, 40 g hybrid poplar was catalytically pretreated at 10% biomass solids content (w/vol or "solids loading") with a reaction mixture containing 2 mM copper sulfate pentahydrate, 4 mM 2,2'-bipyridine, 270 mM NaOH and 10% (w/w) $H_2O_2$ loading on biomass at 30° C., pH 11.5 for 24 hrs to produce pretreated poplar. Desorption of adsorbed copper from pre-treated poplar was carried out by reducing the pH of the pretreated poplar biomass to a pH of 5 by adding 1.6 mL of 72% $H_2SO_4$. The reaction mixture was catalytically pretreated in the same rotary shaker described above at 30° C., 120 rpm for 1 hr. After catalytic pretreatment, the resulting pretreated poplar slurry was centrifuged to separate the pretreated poplar from the aqueous pretreatment liquor (PTL), i.e., the aqueous phase collected following catalytic pretreatment. The PTL was collected to use for subsequent pretreatment step. One (1) mL of sample was analyzed with inductively coupled plasma mass spectrometry (ICP-MS; Thermoscientific iCAP 6500 ICP) to determine the concentration of copper in the PTL, which was found to be about 0.9 mM.

Pretreatment Using the PTL

PTL (4.33 mL) was mixed with 0.5 g hybrid poplar (10% solids loading) with copper catalyst (Copper:bipyridine) of varying ratios. NaOH (270 mM) and $H_2O_2$ (10% loading on biomass) were added to the reaction mixture and the pretreatment lasts for 24 hrs at 30° C. After incubation, the biomass slurry was enzymatically hydrolyzed to yield monomeric sugars.

Due to the presence of 50% of originally added copper in the PTL, the slurry was loaded with different copper (≤1 mM) and bipyridine 2 mM) concentrations to match the concentrations with conventional AHP pretreatment (Copper 2 mM and bipyridine 4 mM). Results demonstrated that there were 50% less yields as compared to an AOP pretreatment in which a single ligand was used. The same yields were also obtained for different extra loadings of Cu and Bpy as obtained with just PTL (FIGS. 4A and 4B).

These results suggest that inhibition is occurring, which could be due to the presence of extra free copper during enzymatic hydrolysis.

Figure 5:
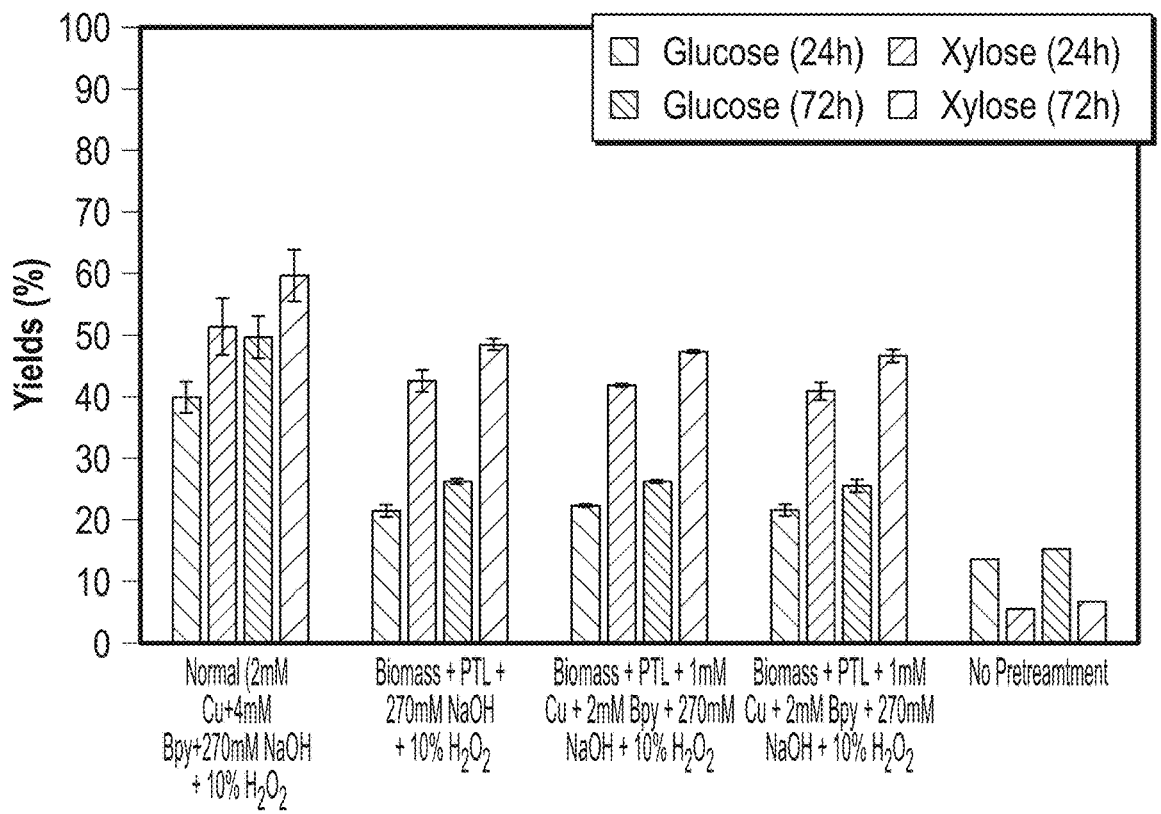
FIG. 5 is a graph showing the effect of a catalyst in PTL for oxidative pretreatment on enzymatic digestibility of pretreated biomass according to an embodiment.

This testing shows that using the catalyst in PTL for oxidative pretreatment improves the enzymatic digestibility of pretreated biomass by about 5% (FIG. 5). As demonstrated in other testing described in Example 8, supplementing more catalyst in addition to PTL does not improve the efficacy of the catalytic oxidative pretreatment.

Example 8

Other approaches beyond the approach described in the above examples were also used to pretreat the poplar biomass utilizing PTL, with the preferred approach determined on the basis of higher sugar yields after enzymatic hydrolysis.

In a second approach, PTL was added to the 0.5 g hybrid poplar biomass (10% solids loading on biomass by weight) with or without 2 mM bipyridine. NaOH (270 mM) and $H_2O_2$ (10% loading on biomass by weight) were added to the reaction mixture to carry out a catalytic pretreatment for 24 hrs at 30° C. to produce a pretreated poplar slurry which was washed using 5 mL distilled water. The washed pretreated poplar slurry was centrifuged in same manner as described in earlier Examples to separate the solid and liquid phases. The solid phase was enzymatically hydrolyzed to obtain the sugar yields.

In a third approach, 0.5 g of hybrid poplar (10% solids loading on biomass by weight) was catalytically pretreated with 4.73 mL of PTL and 270 mM NaOH at 30° C., 120 rpm for 1 hr to produce pretreated poplar slurry. The pretreated poplar slurry was washed with 5 mL of distilled water and centrifuged to separate the copper-containing aqueous phase from the solid phase. The solid phase (containing an amount of adsorbed copper) was subject to an additional incubation with 2 mM bipyridine, 270 mM NaOH and 10% $H_2O_2$ at 30° C., pH-11.5 for 24 hrs. Thereafter, the incubated pretreated poplar slurry was enzymatically hydrolyzed to yield monomeric sugars.

No additional copper was added in the pretreatment utilizing these different approaches. Control experiments were run to ensure the recovery and adsorption of copper into the new biomass.

Extractives Removal and Alkali Recovery Experiment

On the basis of results obtained from above defined approaches, a two-step pre-treatment process was designed. As such, 0.5 g of hybrid poplar biomass (10% w/v insoluble solids concentration) was pre-incubated with 270 mM NaOH at 30° C. for 1 hr. After incubation, contents of the reaction were washed with 5 mL water and centrifuged to separate solid and liquid phases. Solid phase, i.e., alkali pre-extracted biomass was subjected to catalytic AOP pretreatment, while the liquid phase was recovered in the same manner as described in previous examples. The pH of all the pretreatment reactions were carefully monitored and documented.

Enzymatic Hydrolysis

Enzymatic hydrolysis was performed at 50° C. in a temperature controlled incubator shaker at 210 rpm for 72 hrs. After pretreatment, 20 μL of 72% (w/w) $H_2SO_4$ and 500 μL of 1 M sodium citrate buffer (pH 5.0) were added to the pretreated slurry to adjust the pH to 5 (optimum pH for enzymes). Next, 40 μL of 10 mM tetracycline(Sigma-Aldrich) stock solution was added to inhibit microbial growth, followed by addition of the enzyme cocktail consisting of Cellic CTec2 and HTec2(Novozymes A/S, Bagsværd, DK) at a loading of 30 mg protein/g glucan each on the untreated biomass unless otherwise noted.

The enzymatic reaction was carried out at 5% solids loading by adjusting the volume to 10 mL by the addition of deionized water. Following enzymatic hydrolysis, the solid and liquid phases were separated by centrifugation, and the amount of glucose and xylose released into the aqueous phase was quantified by HPLC (Agilent 1100 Series equipped with an Aminex® HPX-87H column operating at 65° C., a mobile phase of 0.05 M $H_2SO_4$, a flow rate of 0.6 mL/min, and detection by refractive index). The yield of glucose and xylose released was defined as the amount of solubilized monosaccharide divided by the total sugar content of the biomass prior to pretreatment as determined by chemical composition analysis.

ICP-MS metal analysis results showed that PTL contained 0.9 mM copper which was approximately 50% of copper concentration (2 mM) originally added during the pretreatment.

Results

Results of the second approach demonstrated that there was an increase in the glucose yields compared to the yields obtained from the first approach described in the other examples. Addition of extra bipyridine further increased the yields. There was 6 to 8% increase in the glucose yield whereas lower xylose yield was obtained. Low xylose yields could be explained as due to washing step after pretreatment, hemicellulose was also removed from the reaction mixture.

No extra copper was added in these experiments. Yields obtained were purely from recycled copper.

These yields matched the yields achieved with conventional AOP pretreatment, i.e., one-step catalytic AOP with no extraction, incubation or impregnation beforehand. Increased yields were obtained with addition of bipyridine in the form of a bipyridine-copper complex.

The third approach (described above) produced the highest sugar yields as compared to the other approaches. The glucose yields obtained from this approach were approximately 28% higher compared to conventional catalytic AOP.

Addition of only PTL to biomass without any addition of bipyridine yielded 7% higher glucose yields compared to conventional catalytic AOP.

No extra copper was added in these experiments. Yields obtained were purely from recycled copper.

These results show that extractives from PTL can inhibit the performance of catalytic AOP by affecting the pH of the reaction and/or by interfering with useful reactions. It is also possible that enzymatic hydrolysis was inhibited due to the presence of extractives.

Overall results demonstrated the ability to recycle the copper and increase the glucose yields by about 82% to about 85% and xylose yields by about 55% to about 58%.

Modification of Catalytic AOP

On the basis of results obtained from copper recycling and extractives removal, a two-step process was developed, with the first step removing extractives and alkali-extractable lignin and xylan with NaOH and the second step consisting of catalytic AOP.

Figure 6:
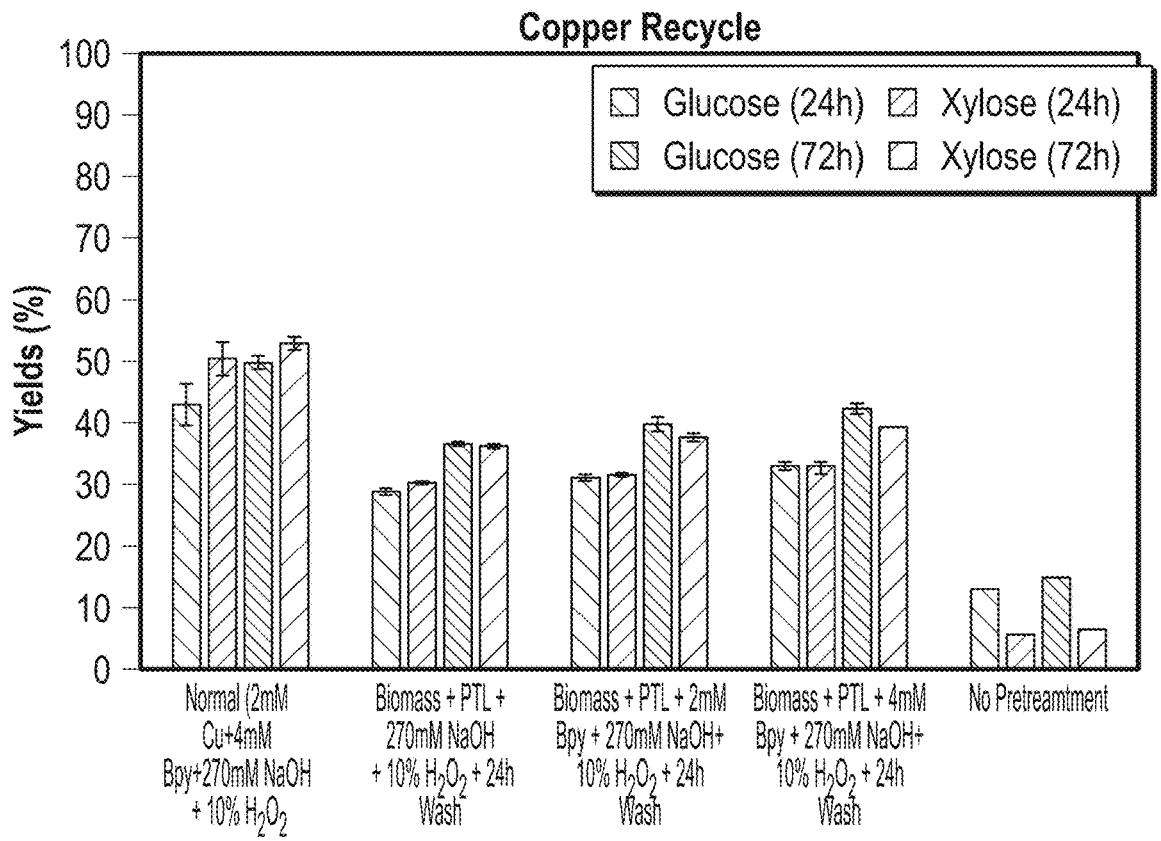
FIG. 6 is a graph showing yields of glucose and xylose (with copper recycling) under varying pretreatment conditions according to various embodiments.

Sugar yields obtained from modified catalytic AOP were about 28 to about 30% higher than sugar yields obtained using conventional single-ligand catalytic AOP. Different control experiments were also carried out to ensure that the yields obtained are due to extractives removal, see FIG. 6.

Figure 7:
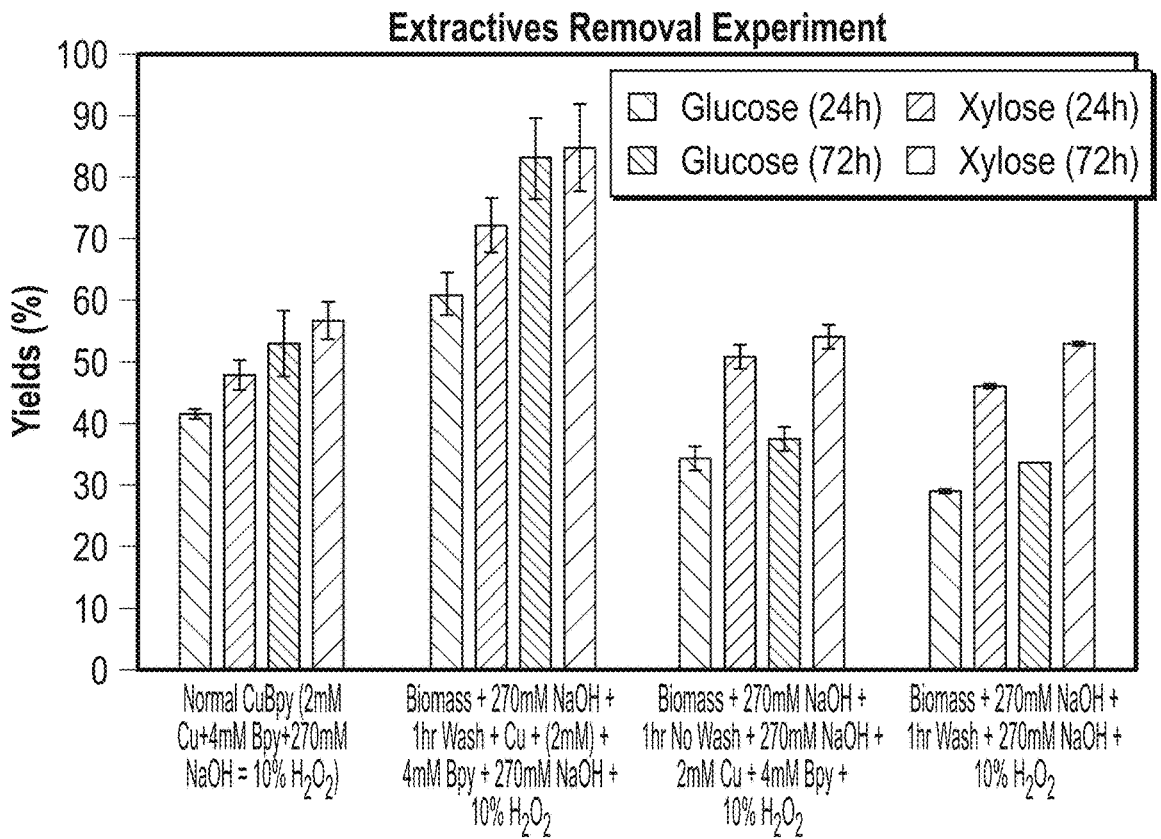
FIG. 7 is a graph showing glucose and xylose yield (with extractives removal) under varying conditions according to various embodiments.

See also improved sugar yields with pre-extraction step shown in FIG. 7.

Example 9

Recycling of Base for Alkaline Extraction

Alkaline extraction was performed following the procedure described in Example 3. Hybrid poplar (from the same source as in previous examples) was extracted with 135 mM or 270 mM aqueous solution of NaOH, and the extracted biomass was then washed with deionized water. The liquid from washing was recovered. The washed solids were pretreated with 10.8 g/L NaOH, 10 g/L $H_2O_2$, 2 mM $CuSO_4$ and 4 mM 2,2'-bipyridine. The pretreated solids were enzymatically hydrolyzed following the procedure described in Example 3. Over 80% of the glucose was recovered after enzymatic hydrolysis (FIG. 7).

Figure 8:
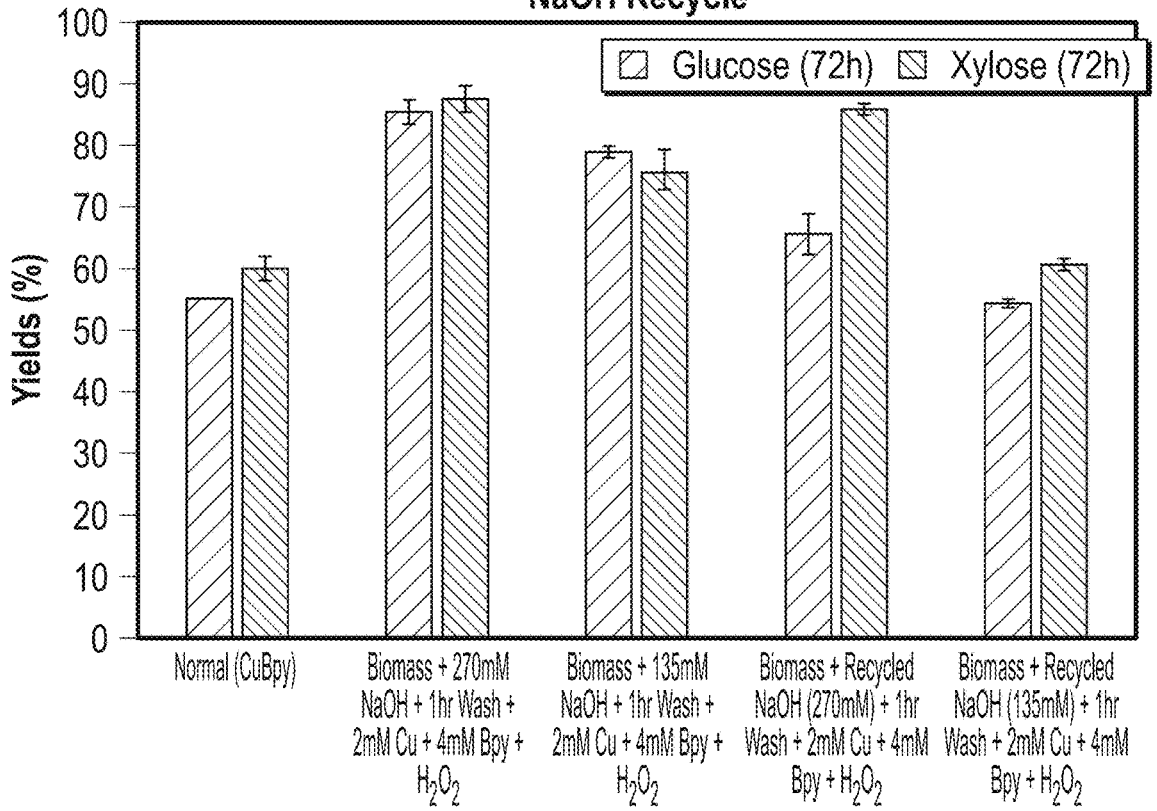
FIG. 8 is a graph showing glucose and xylose yield (with NaOH recycle) under varying conditions according to various embodiments.

The liquid from washing ("Recycled NaOH") was used for alkaline extraction of hybrid poplar, following the procedure described in Example 3. After 1 hour of extraction at 30° C., the mixture was washed with deionized water, and the remaining solids was pretreated with 10.8 g/L NaOH, 10 g/L $H_2O_2$, 2 mM $CuSO_4$ and 4 mM 2,2'-bipyridine. The pretreated solids were enzymatically hydrolyzed following the procedure described in Example 3. More than 60% of the glucose was recovered after enzymatic hydrolysis (FIG. 8).

Compared to conventional single-ligand catalytic AOP, consumption of alkali was doubled in this modified catalytic AOP. To be more cost effective, experiments were performed to recycle the alkali from pre-extraction step or use less alkali in the respective step.

Results

Sugar yields obtained using less alkali, i.e., 135 mM NaOH, were comparable to the yields obtained from the 270 mM NaOH pre-extraction step. The NaOH was also partially recycled. Yields obtained from the recycled 270 mM NaOH reaction were about 66% glucose and 85% xylose. These yields are higher than yields obtained with the conventional single-ligand catalytic AOP process (FIG. 8).

Example 10

Biomass, Pretreatment, and Hydrolysis

Hybrid poplar (*Populus nigra* var. charkoviensis×caudina cv. NE-19) was grown at the University of Wisconsin Arlington Agricultural Research Station. Prior to pretreatment, a mixture of heartwood and sapwood of the 18-year-old poplar was hammer-milled to pass a 5 mm screen. See, for example, Li Z, Chen C H, Liu T, Mathrubootham V, Hegg E L, Hodge D B: Catalysis with $Cu^{II}$(bpy) improves alkaline hydrogen peroxide pretreatment. Biotechnol Bioeng 2013, 110:1078-1086.37 and Li Z, Chen C, Hegg E, Hodge D: Rapid and effective oxidative pretreatment of woody biomass at mild reaction conditions and low oxidant loadings. Biotechnol Biofuel 2013, 6:119, for additional details as to compositional analysis and pretreatment specifics. For AOP-only pretreatment, hybrid poplar (0.5 g) was pretreated in 5 mL aqueous aliquots of 10 g/L $H_2O_2$ (10% w/w loading on biomass) and 10.8 g/L NaOH (final pH of approximately 11.7) at 30° C. for 1 hr unless otherwise noted. During the pretreatment, the samples were agitated at 180 rpm in an orbital shaker. For Cu-catalyzed AOP pretreatments, 5 mM $CuSO_4$ and 25 mM 2,2'-bipyridine were included in the 5 mL aliquot during pretreatment. For alkali-only (AOP-only) pretreatment, 0.5 g of hybrid poplar was pretreated in 5 mL aqueous aliquots of 10.8 g/L NaOH.

TEM Imaging and Elemental Profiling of Pretreated Cell Walls

Structural modification of hybrid poplar cell wall by pretreatment was studied using transmission electron microscope (TEM) combined with energy-dispersive X-ray spectroscopy (EDS) and electron energy-loss spectroscopy (EELS). The conditions used for pretreatment were identical to those used to prepare size exclusion chromatography (SEC) samples. Cell wall samples of untreated hybrid poplar and hybrid poplar treated with AOP and Cu-catalyzed AOP for 24 hr were air dried and fixed (i.e., embedded) in a resin comprising 0.1 M pH 7 phosphate buffer containing 2.5% (w/w) glutaraldehyde and 2.5% (w/w) paraformaldehyde. The fixed cell wall samples were embedded in Spurr epoxy resin (Poly/Bed 812, Polysciences) and sectioned to 100 nm thickness using a PowerTome XL ultramicrotome (Boeckeler Instruments, Tucson, Ariz., USA). Thin sections were placed on 150 mesh gold grids with Formvar/carbon support film (Electron Microscopy Sciences, PA) and stained in 1% aqueous solution of $KMnO_4$ for 60 sec. Samples were then rinsed with deionized water to remove excess stain. Bright field TEM micrographs and EELS spectra were acquired under a JEOL 2200FS 200 kV field emission TEM (Peabody, Mass., USA) fitted with a Gatan (Warrendale, Pa., USA) digital multi-scan camera. EDS spectra were acquired using an Oxford *INCA* system (Oxford Instruments, Abington, UK) coupled with the TEM.

Analysis or Pretreatment Liquors

For analysis by SEC or LC-MS, pretreatment liquors at alkaline pH were filtered through a 0.22 μm mixed cellulose ester membrane filter (EMD Millipore, Billerica, Mass.). SEC analysis was performed using an Agilent 1100 HPLC equipped with an Ultrahydrogel 250 column (Waters, Milford, Mass., USA) as described in Stoklosa R J, Hodge D B: Extraction, recovery, and characterization of hardwood and grass hemicelluloses for integration into biorefining processes. *Ind Eng Chem Res* 2012, 51:11045-11053. Aqueous solutions of monodisperse sodium polystyrene sulfonate (Sigma-Aldrich, St. Louis, Mo., USA) of known molar mass (2000, 4300, 6800, 10000, 32000, and 77000 Da) were used as calibration standards.

Samples for Liquid Chromatography-Mass Spectrometry (LC-MS) analysis were prepared as described above for SEC analysis, except that the concentrations of CuSO4 and 2,2'-bipyridine during pretreatment were 2 mM and 4 mM, respectively. For LC-MS analysis, 10 μL of undiluted pretreatment liquor sample were injected into a XEVO G2SQTOF mass spectrometer in combination with a Waters Acquity® UPLC system and equipped with an Electrospray Ionization (ESI) interface capable of operating in both positive- and negative-ion modes. Chromatographic separation was carried out on a Thermo Beta Basic 100×2.1 mm C18 column (Thermo Fisher Scientific, Waltham, Mass., USA) maintained at 40° C. The binary solvent gradient consisted of 0.1% formic acid in water (solvent A) and 100% methanol (solvent B) in the following gradient: 95% solvent A for the first 3 min, 50% solvent A over the next 1 min, 30% solvent A over next 2 min, and 5% solvent A over the final 2 min. The column was then returned to 95% solvent A, and equilibrated for 2 min prior to the next injection. A solvent delay of 2 min was used to prevent saturation of the detector with the sample solvent.

The negative-ion mode mass spectrometry conditions were constant during all experiments with a voltage of −2.25 kV and a desolvation temperature of 350° C. Mass Lynx software (Waters) version 4.1 was used for system control and data acquisition. The raw data acquired were processed using the Target Lynx application. Pure standards for vanillin, vanillic acid, acetovanillone, syringaldehyde, syringic acid, acetosyringone, and p-hydroxybenzoate (Sigma-Aldrich, St. Louis, Mo., USA) were used to validate peak compound identification and for quantitation.

For quantitation of p-hydroxybenzoate, samples were prepared following the same procedure as that for the LC-MS analysis, but the samples were then analyzed via high-performance liquid chromatography (Agilent 1260 LC equipped with an Agilent Poroshell 120 EC-C18 column (4.6×50 mm) and a diode array detector (DAD). Integration of the p-hydroxybenzoate peak at 280 nm and comparison to a standard curve was used for quantitation. A binary isocratic solvent system was utilized consisting of 80:20 solvent C to solvent D, where solvent C is acetonitrile with 0.1% water, and solvent D is acetonitrile with 0.1% trifluoroacetic acid.

NMR Analysis of Whole Cell Walls and Pretreatment-Solubilized Lignin

Following the pretreatment, the aqueous phase was separated from the solid phase (i.e., the insoluble portion of pretreated poplar) via filtration, and the filtrate was acidified to pH 2.0 with 72% (w/w) sulfuric acid. The precipitate from the acidified filtrate was recovered via centrifugation and washed with a large volume of aqueous sulfuric acid (pH 2.0) followed by a final washing step of re-suspending and decanting the lignin sample in pH-neutral deionized water. The washed lignin precipitate was lyophilized prior to NMR analyses. The 2D HSQC NMR spectra of three types of samples (untreated hybrid poplar, recovered solubilized lignins and the insoluble portion of pretreated poplar) were acquired and analyzed according to the methods described in Kim H, Ralph J, Akiyama T: Solution-state 2D NMR of ball-milled plant cell wall gels in DMSO-$d_6$. *Bioenerg Res* 2008, 1:56-66 (hereinafter "Kim 2008") Untreated and pretreated samples were prepared for gel-state NMR as y described in Kim (2008).

In brief, the dried sample was pre-ground for 1 min in a Retsch MM400 mixer mill at 30 Hz, using zirconium dioxide (ZrO2) vessels (10 mL) containing $ZrO_2$ ball bearings (2×10 mm). The ground material was extracted with distilled water (1 hr, 3 times) and 80% of ethanol (1 hr, 3 times) with ultrasonication. The cell walls were dried and finely ball-milled using a PULVERISETTE 7 (Fritsch, Idar-Oberstein, Germany) mill at 600 rpm with $ZrO_2$ vessels (50 mL) containing with $ZrO_2$ ball bearings (10×10 mm). Each sample (200 mg) was milled for 1 hr, 40 min in 10 min intervals with 5 min interval breaks. The ball-milled samples (50 mg of each) were transferred into 5-mm NMR tubes and gels formed using DMSO-$d_6$/pyridine-$d_5$ (4:1, v/v, 0.5 mL) with sonication (30 min). NMR spectra were acquired on a Bruker BioSpin (Billerica, Mass., USA) AVANCE 700 MHz spectrometer equipped with a cryogenically-cooled 5-mm triple-resonance 1H/13C/15N TXI gradient probe with inverse geometry (1H coils closest to the sample).

The central DMSO solvent peak was used as an internal reference ($\delta_C$ 39.5, $\delta_H$ 2.49 ppm). The $^1$H-$^{13}$C correlation experiment was an adiabatic HSQC experiment (Bruker standard pulse sequence 'hsqcetgpsisp.2'; phase-sensitive gradient-edited 2D HSQC using adiabatic pulses for inversion and refocusing). HSQC experiments were carried out using the following parameters: acquired from 9 to 1 ppm in F2 (1H) with 1,200 data points (acquisition time 200 ms), 160 to 10 ppm in F1 (13C) with 512 increments (F1 acquisition time 13.6 ms) of 32 scans with a one-second interscan delay; the d24 delay was set to 0.86 ms (⅛J, J=145 Hz).

Figure 9A:
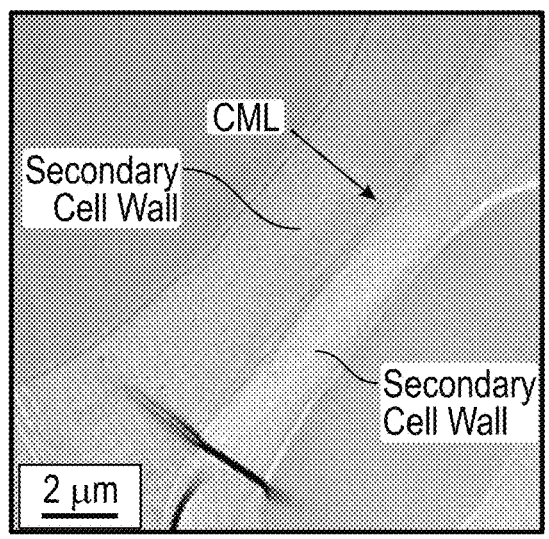
FIGS. 9A-9C are Transmission Electron Microscopy (TEM) micrographs of cross sections of an untreated (A) and Alkaline Oxidative Peroxide (AOP)-only pretreated (B,C) hybrid poplar cell wall according to various embodiments.

Volume integration of contours in HSQC plots used Bruker's TopSpin 3.1 (Mac) software. Assignments of peaks from NMR spectra were based on Kim 2008 and Kim H, Ralph J: Solution-state 2D NMR of ball-milled plant cell wall gels in DMSO-d6/pyridine-d5. Org Biomol Chem 2010, 8:576-591. TEM imaging was used to characterize corn stover cell wall structural changes associated with pretreatments by dilute acid, and anhydrous ammonia, as well as acid chlorite delignification. The TEM micrographs of untreated hybrid poplar (FIG. 9A) and AOP-only pretreated hybrid poplar (FIGS. 9B and 9C) showed identifiable features of the cell walls comprising wall layers that include secondary cell wall layers (FIGS. 13A-13F and FIG. 15) and the compound middle lamella (CIVIL), as well as cell corners (CC) and individual lumens. Following AOP-only pretreatment (FIGS. 9A and 9B), the cell walls retained much of their structural integrity, as seen by the similarities to those of untreated cell walls. The only notable changes were dislocations which formed between the middle lamellae and the primary cell walls, possibly due to removal of some lignin and pectic polysaccharides during pretreatment. The dark black stripes observed in the micrographs are artifacts introduced during ultramicrotome sectioning and $KMnO_4$ staining.

Figure 10A:
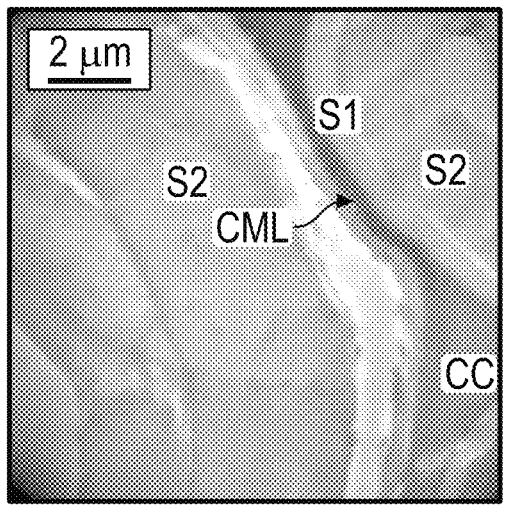
FIGS. 10A-10D are TEM micrographs of a hybrid poplar cell wall after copper(II) 2,2'-bipyridine complex (Cu(bpy))-catalyzed AOP pretreatment showing delamination (A) and dislocations of cell wall layers (B), together with accumulation of nanoparticles in disrupted regions (C,D) according to various embodiments.
Figure 10B:
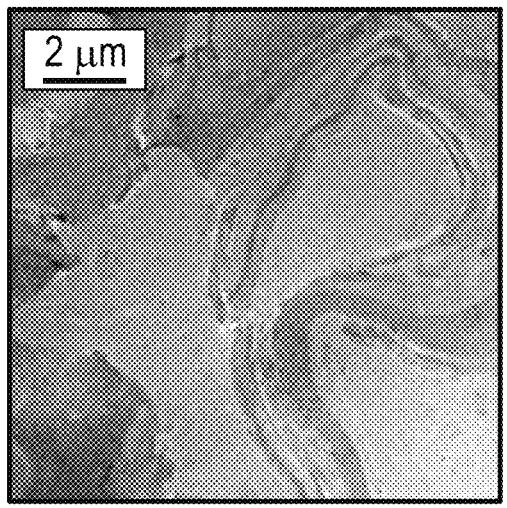
Figure 10C:
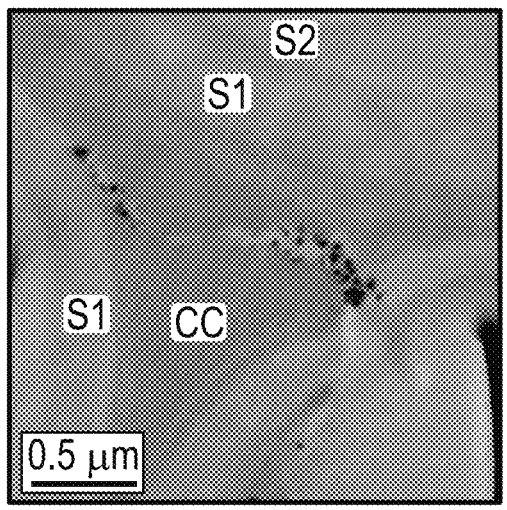
Figure 10D:
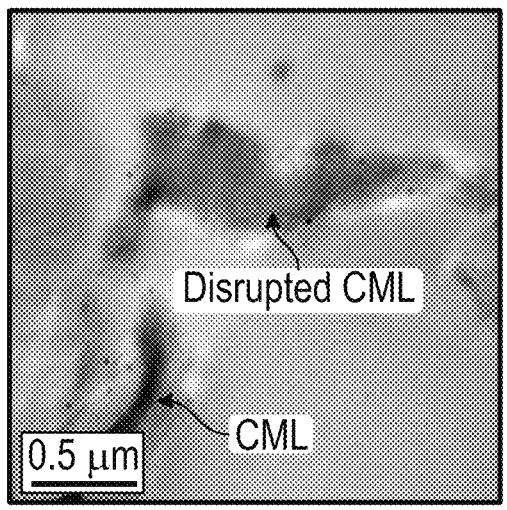

Addition of Cu(bpy) complexes during AOP pretreatment of hybrid poplar improved delignification and enzymatic hydrolysis yields. TEM characterizations of hybrid poplar cell wall after Cu-catalyzed AOP pretreatment are shown in FIGS. 10A-10D, with FIG. 10A showing delamination, FIG. 10B showing dislocations of cell wall layers along, and FIGS. 10C and 10D showing the accumulation of nanoparticles in disrupted regions. "S1" and "S2" indicate different layers of the secondary cell wall; "CC" refers to a cell corner and "CIVIL" refers to the compound middle lamella. As FIGS. 10A-10D show, significant cell wall structural changes occurred as a result of Cu(bpy)-catalyzed AOP pretreatment. See, for example, the major dislocations in the cell wall in FIG. 10A, together with formation of fractures in which the secondary cell wall layers were perturbed. Fractures and disruptions were also observed in other lignin-rich regions, including cell corners (FIG. 10A) and compound middle lamellae (FIG. 10B), suggesting that the structural changes may be caused by lignin modification and/or removal.

Figure 9B:
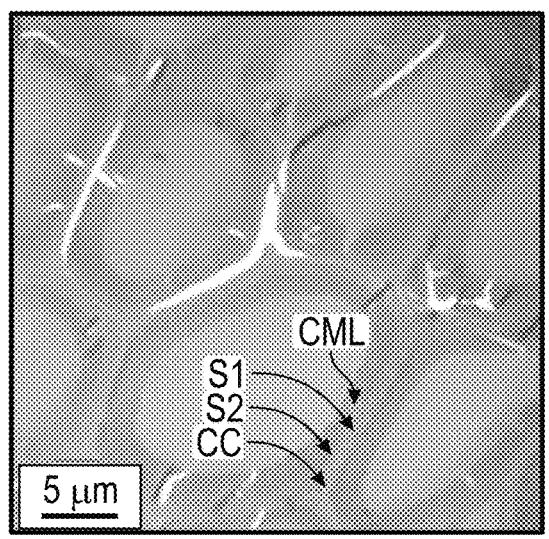
Figure 9C:
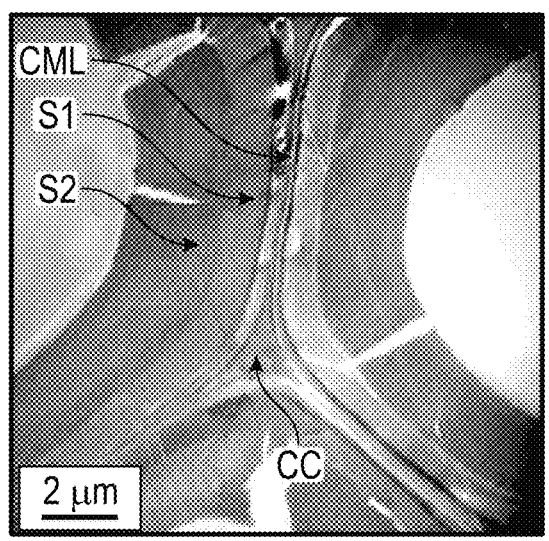

The testing described in this example was performed at temperatures ranging from about 25 to about 30° C., which is well below the lignin glass transition (which is about 100 to about 170° C.). As a consequence, the lignin removal which occurred is primarily due to chemical modification and/or solvent effects rather than thermal effects. Additionally, and as shown in FIGS. 10C and 10D, X-ray-opaque particles with diameters in the range of about 20 to about 100 nm were often co-localized with the modified regions of cell walls. Interestingly, such particles were not found in untreated hybrid poplar (FIG. 9A) or AOP-only pretreated poplar (FIGS. 9B and 9C). As such, the development of such particles can be hypothesized to originate from the copper catalyst, rather than as artifacts introduced during the TEM sample preparation. This suggests that copper is involved in the observed cell wall modification (e.g., via lignin oxidation).

Elemental Profiling of Pretreated Cell Walls

Figure 11A:
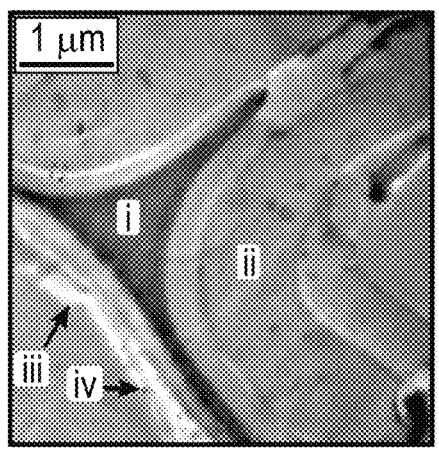
FIGS. 11A-11F are TEM micrographs of hybrid poplar cell wall (A) and high resolution image of an electron-opaque aggregate (B) together with acquired Energy Dispersive X-ray Spectroscopy (EDS) spectra of select regions within this sample (C—F) according to various embodiments.

When combined with electron microscopy, in situ elemental profiling using energy-dispersive X-ray spectroscopy (EDS) and electron energy-loss spectroscopy (EELS) can provide chemical characterization at a spatial resolution on the order of 100 nm. To characterize the elemental composition of the nano-scale particles observed in the TEM images, EDS spectra were acquired at different locations in a TEM sample (FIG. 11A), including at a cell corner (identified as area "i" in FIG. 11A), within a secondary cell wall (area "ii"), and over the previously described particles (areas "iii" and "iv").

Figure 11B:
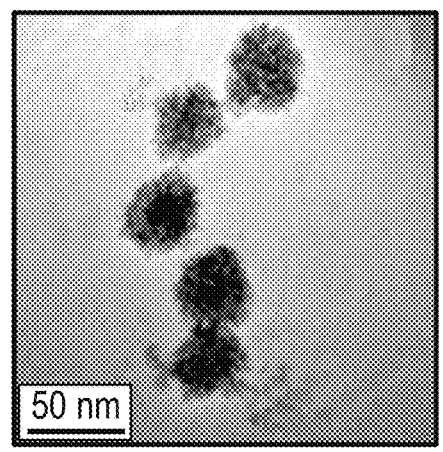
Figure 11C:
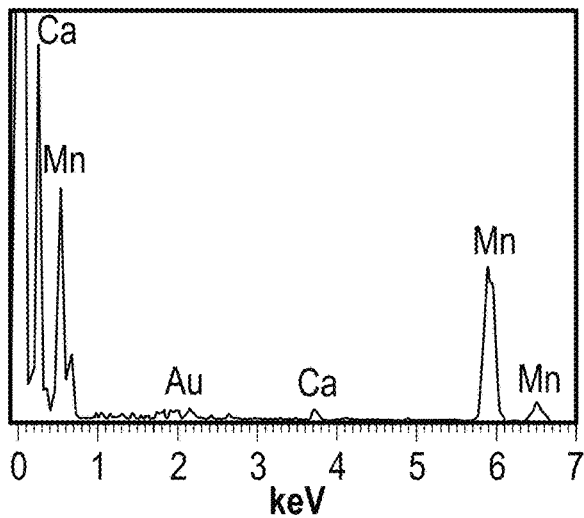
Figure 11D:
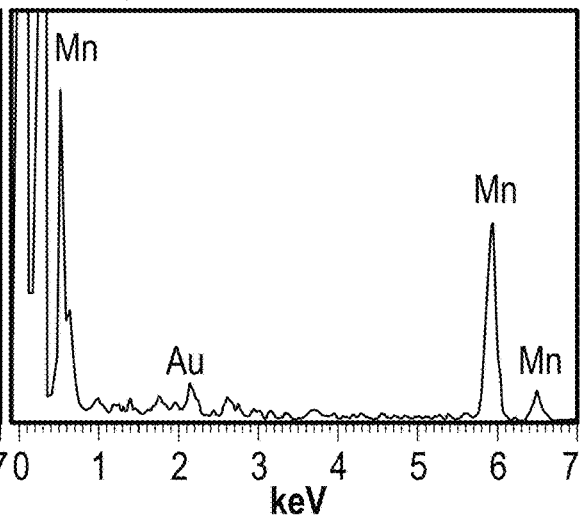
Figure 11E:
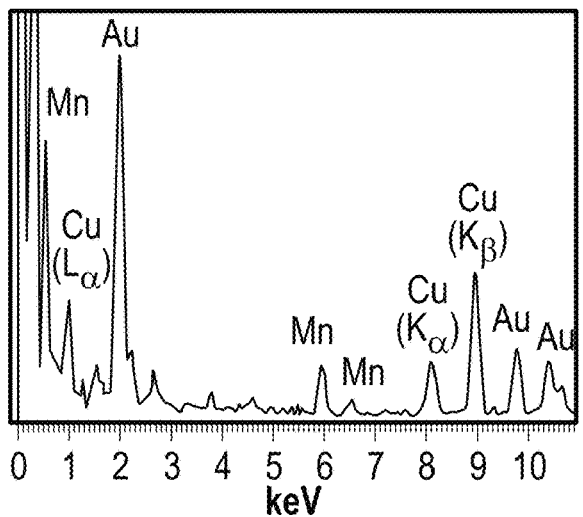
Figure 11F:
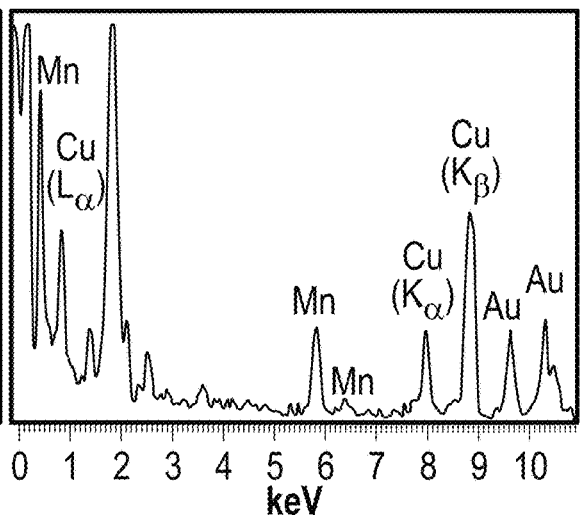

TEM images at high magnification show that these particles are aggregates with dendritic structures and diameters on the order of 50 nm (FIG. 11B). A comparison of the EDS spectra reveals both similarities and differences in elemental composition of the cell wall regions (FIGS. 11C-11F). Mn peaks are apparent in all four spectra and are a consequence of the permanganate staining, whereas the Au peaks correspond to the X-ray emissions from the grid that supports the TEM sample. The EDS spectrum from the cell corner (area "i") shows a strong Ca L-edge peak indicating the presence of Ca ions, which are known to complex with pectin. Ca K-edge peaks (3.7 keV) are also present at a lower relative abundance in the spectra of the other cell areas. In the areas of "ii" and "iii" where X-ray-opaque particles were analyzed, the EDS spectra feature characteristic peaks for Cu. The Cu L-edge and K-edge peaks are not seen in the EDS spectra of either the cell corner (area "i") or the secondary cell wall (area "ii"). EELS was used to identify the oxidation state of the Cu-containing particles (FIG. 15), which shows the spectrum of a Cu-containing particle with the pre-edge background subtracted. The white-line intensity (i.e., the sharp threshold peaks) of the Cu L2,3 edge indicates that the majority of the Cu is in the Cu(I) oxidation state, while the relatively low white-line intensity of L3 implies that Cu(0) is also present.

The identification of Cu-containing particles suggests that the Cu catalyst is localized in the cell wall matrix at sites corresponding to those with significant structural modification. This result suggests that the soluble Cu catalysts diffuse into the porous cell wall matrix during pretreatment and subsequently catalyze the formation of localized reactive oxygen species that may be involved in the oxidative delignification and structural modification of the cell wall in their vicinity. Although the active catalytic complexes have not yet been identified, one possibility is that the oxidation reactions were accelerated by Cu complexes that catalyzed the decomposition of $H_2O_2$ and/or activated $H_2O_2$ via the formation of Cu-peroxide complexes.

With respect to the timing of the formation of the Cu-containing particles, it is possible that the solubility and speciation of the Cu(bpy) complexes are a function of pH, concentration, and ligand to metal ratio, with the Cu(bpy) complexes being substantially more soluble at the alkaline pH where pretreatment occurs. As a consequence, Cu-containing particles may be precipitating at the neutral pH where sample fixation is performed. Another possibility is that the observed Cu-containing particles are providing indirect evidence of catalytic activity as the soluble Cu(bpy) complexes are reduced from Cu(II) to the observed Cu(I) and Cu(0) oxidation states during the pretreatment process and are subsequently deposited as insoluble aggregate particles. It is not yet known whether or not these particles are catalytically active or inactive. Furthermore, the reduction of Cu(II) by the incident electrons during TEM imaging also cannot yet be ruled out.

Characterization of Solubilized Cell Wall Biopolymers and Phenolic Monomers

Cell wall biopolymer structural changes associated with this pretreatment were assessed using multiple analytical approaches. In the first approach, the relative abundance and molecular weight distributions of the lignin solubilized during pretreatment were determined by size-exclusion chromatography (SEC) as a function of pretreatment time (FIG. 12).

Figure 12:
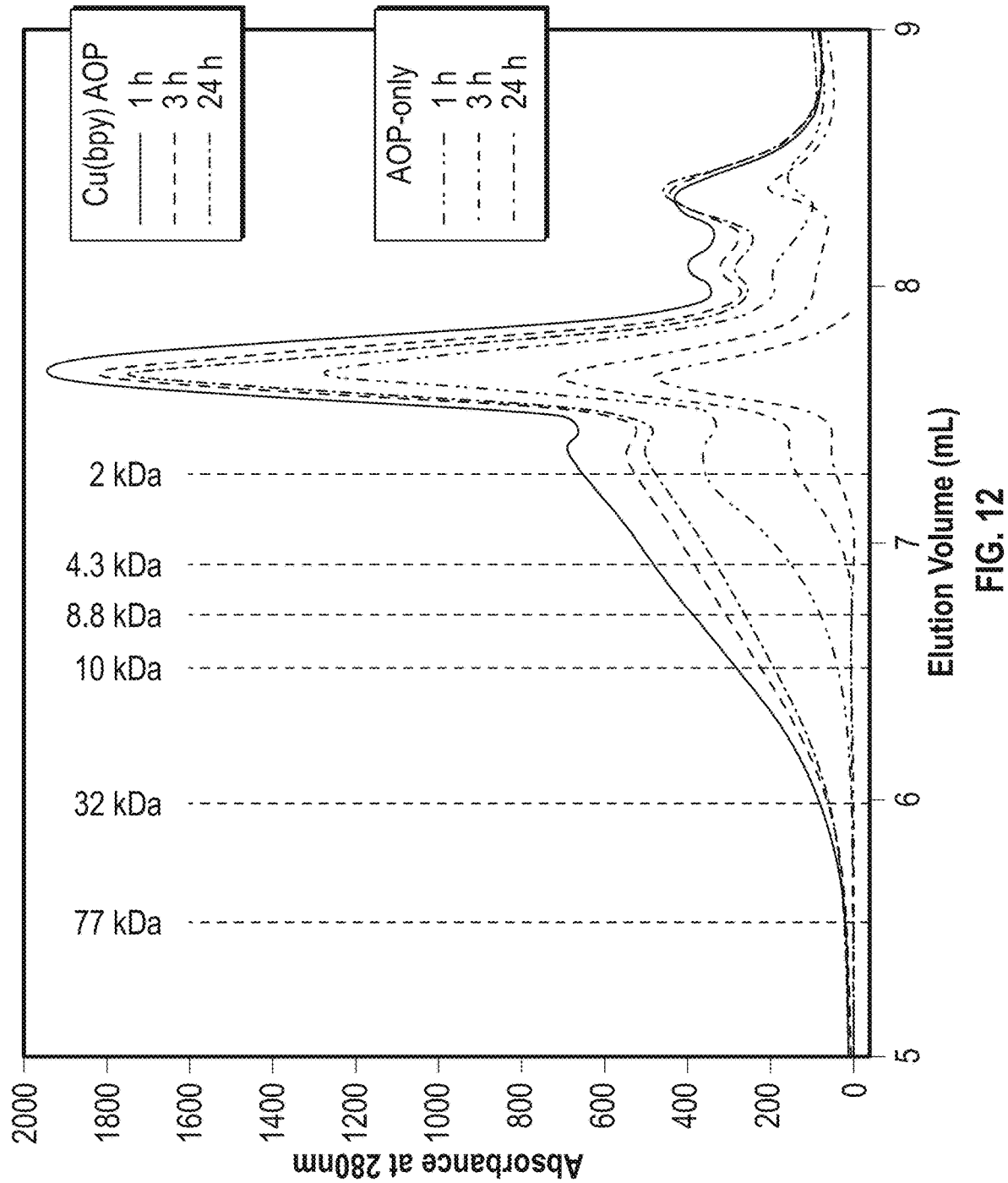
FIG. 12 shows SEC elution profiles for plant cell wall polymers solubilized during pretreatments referenced to elution times for polystyrene standards according to various embodiments.

As can be seen in FIG. 12, a single large peak representing phenolic monomers and oligomers eluted below an apparent molecular weight of 1000 Da. As these elution profiles show, Cu-catalyzed AOP released significantly more soluble lignin fragments than AOP-only pretreatment. Additionally, as FIG. 12 shows, the molecular weight distributions of the solubilized lignins were not noticeably altered for either of the pretreatments over time, indicating that the soluble lignins were neither undergoing substantial depolymerization, nor repolymerization through condensation reactions.

The distribution and abundance of the phenolic monomers solubilized following pretreatment were quantitated by LC-MS and HPLC. These monomers arise primarily through the cleavage of ether bonds or by saponification of phenolic acids that acylate the lignin polymer. The distribution of phenolic monomers was found to be substantially different when the Cu catalyst was present, with aldehyde products favored over acids as shown in FIG. 4A.

This quantitative difference between the release of phenolic acids and aldehydes suggests that the Cu-catalyzed reaction may utilize a different reaction mechanism that results in less oxidation of the lignin polymer, yet yields more intra-lignin bond cleavage and lignin solubilization than AOP-only treatment.

Additionally, phenolic monomer yields reached only 2 mg/g lignin (i.e., mass of monomer to mass of cell wall lignin) for both AOP-only and Cu-catalyzed AOP pretreatment (FIG. 4), and only 0.5 mg/g lignin by alkali-only pretreatment (FIG. 4A). T Such low phenolic monomer yields suggest that the cleavage of β-O-4-bonds is not complete.

Plants within the family Salicaceae, including the genus *Populus*, are known to have lignins with p-hydroxybenzoate groups acylating the γ-OH of syringyl subunits. As expected, the most abundant phenolic monomer in all of the pretreatment liquors was p-hydroxybenzoate (FIG. 44B), as these esters are easily saponified during alkaline pretreatments. The results show that alkali-only treatment results in the highest yields (14.8 mg/g lignin) with AOP-only and Cu(bpy)-AOP, releasing roughly one third or one half of this quantity. The lower yields following the oxidative treatments are presumably due to the lower pHs during these treatments (due to the acidic contribution of $H_2O_2$) that may result in incomplete saponification of the p-hydroxybenzoate, although oxidative degradation/modification may also contribute to this difference.

2D HSQC NMR of Whole Cell Walls and Solubilized Lignins

Figure 13A:
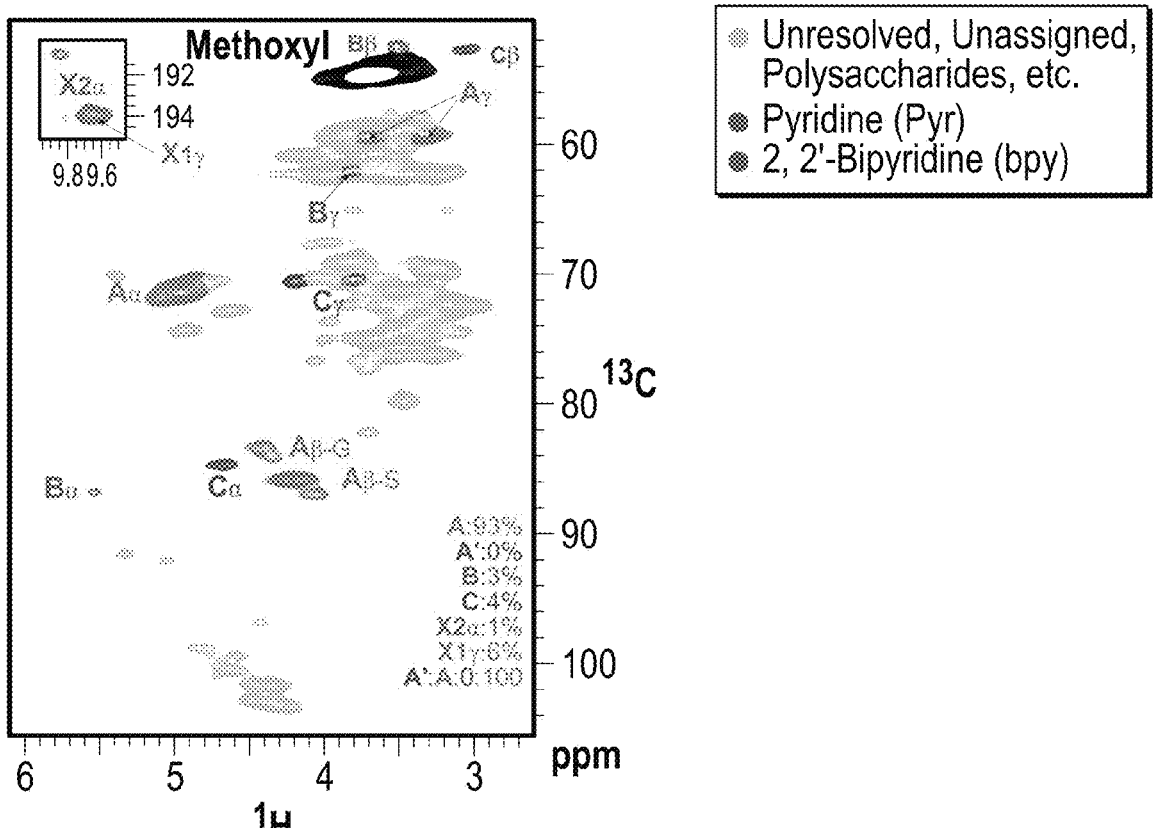
FIGS. 13A-13F are partial 2D Heteronuclear Single-Quantum Coherence (HSQC) Nuclear Magnetic Resonance (NMR) spectra of (A,B) whole cell wall untreated poplar, (C,D) solubilized lignin, and (E,F) residual poplar cell walls following Cu-catalyzed AOP pretreatment showing polysaccharide correlations and colored contours to match structures for aromatic components according to various embodiments.
Figure 13B:
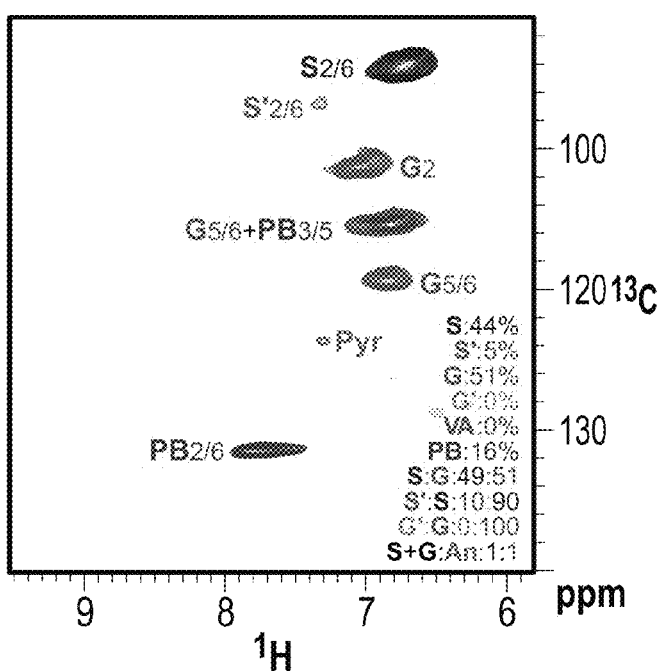
Figure 13C:
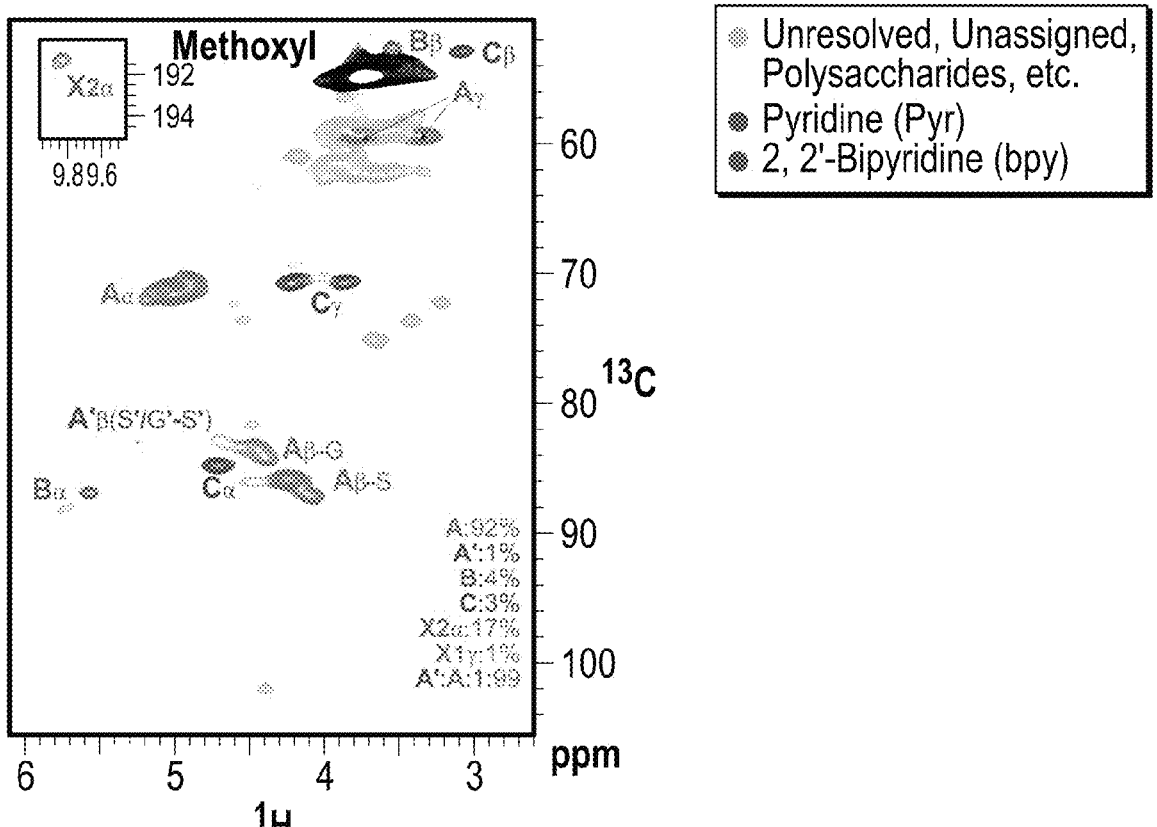
Figure 13D:
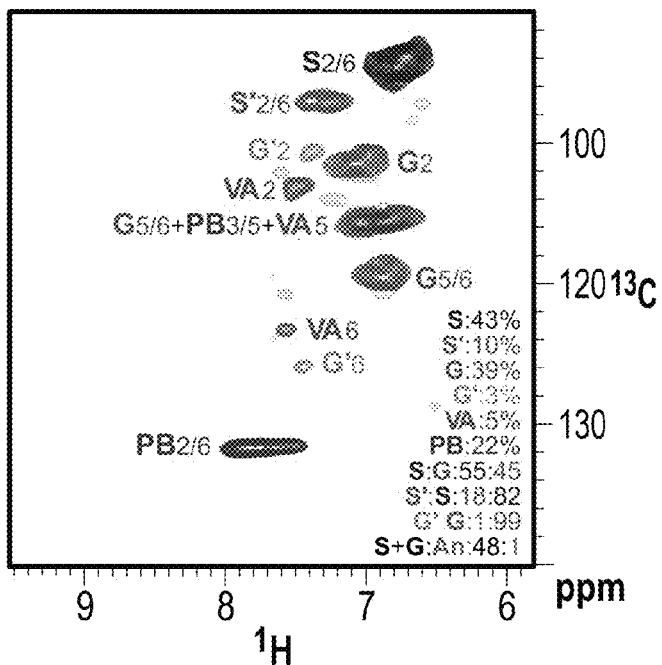
Figure 13E:
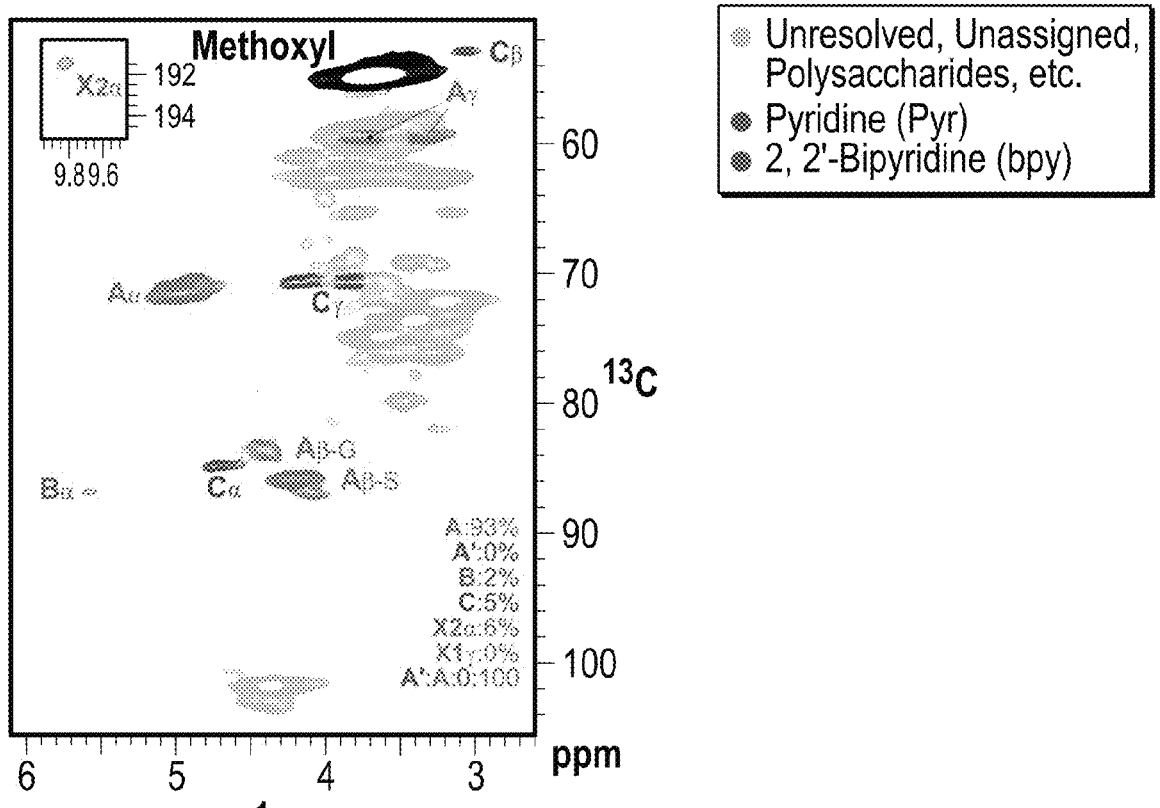
Figure 13F:
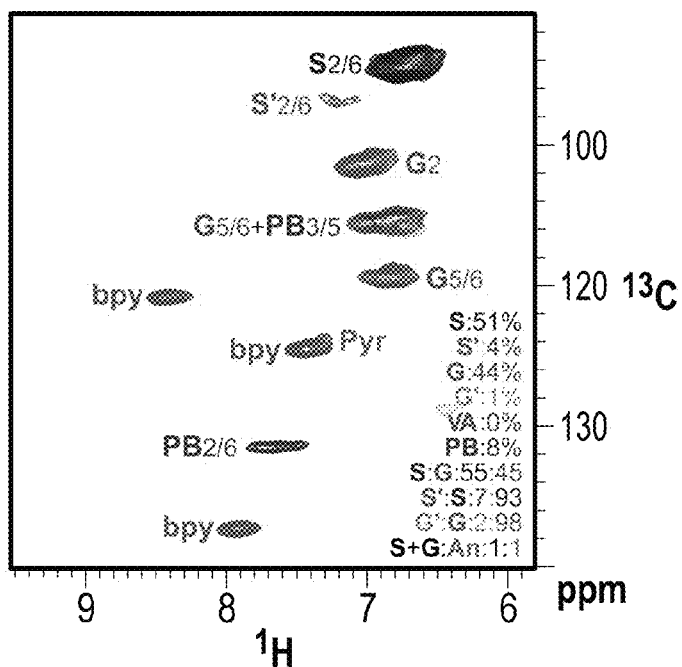

2D HSQC (heteronuclear single-quantum coherence) NMR spectroscopy was used to analyze lignin after Cu-catalyzed AOP pretreatment. NMR characterization was performed on various components, including untreated whole cell wall material from hybrid poplar (FIGS. 13A and 13B), the lignin that was solubilized following one hour of catalytic pretreatment and recovered via acid precipitation (FIGS. 13C and 13D), and the residual insoluble cell wall material following pretreatment (FIGS. 13E and 13F). Several important insights can be gained from these experiments. First, the NMR data provide evidence for lignin oxidation. The aromatic region (FIG. 13D) revealed a substantial increase in oxidized S and G units to their benzylic ketone analogues S' and G' plus new vanillate units (VA). The aliphatic region (FIG. 13C) further supports these chemical changes. Contours are colored to match the structures for aromatic components.

Figure 14A:
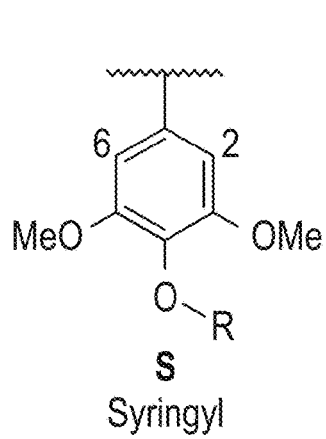
FIG. 14A-14L are representations of various known chemical structures.
Figure 14B:
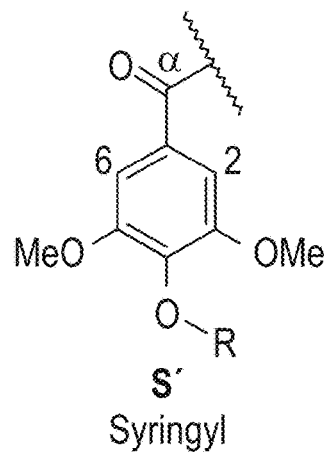
Figure 14C:
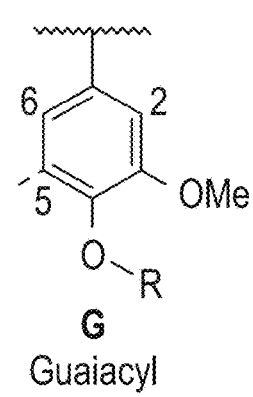
Figure 14D:
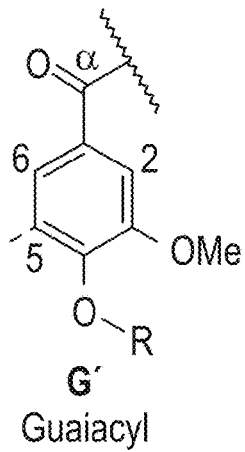
Figure 14E:
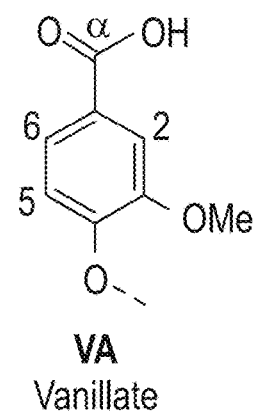
Figure 14F:
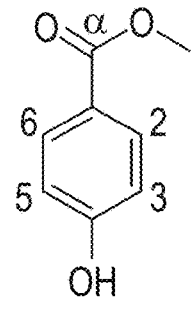
Figure 14G:
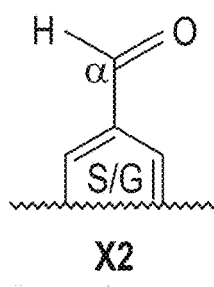
Figure 14H:
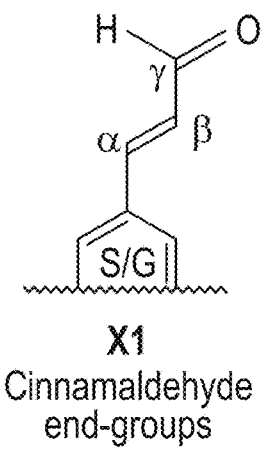
Figure 14I:
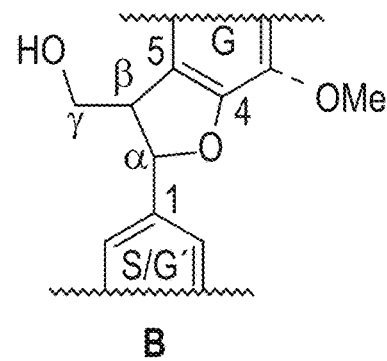
Figure 14J:
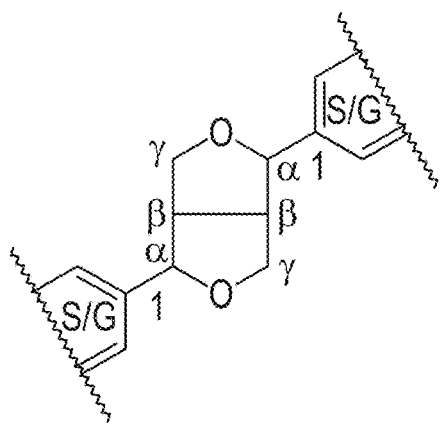
Figure 14K:
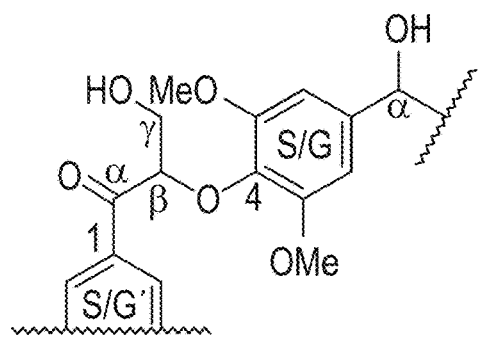
Figure 14L:
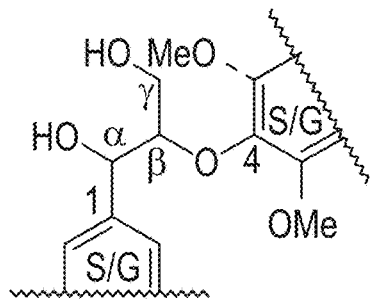
Figure 15:
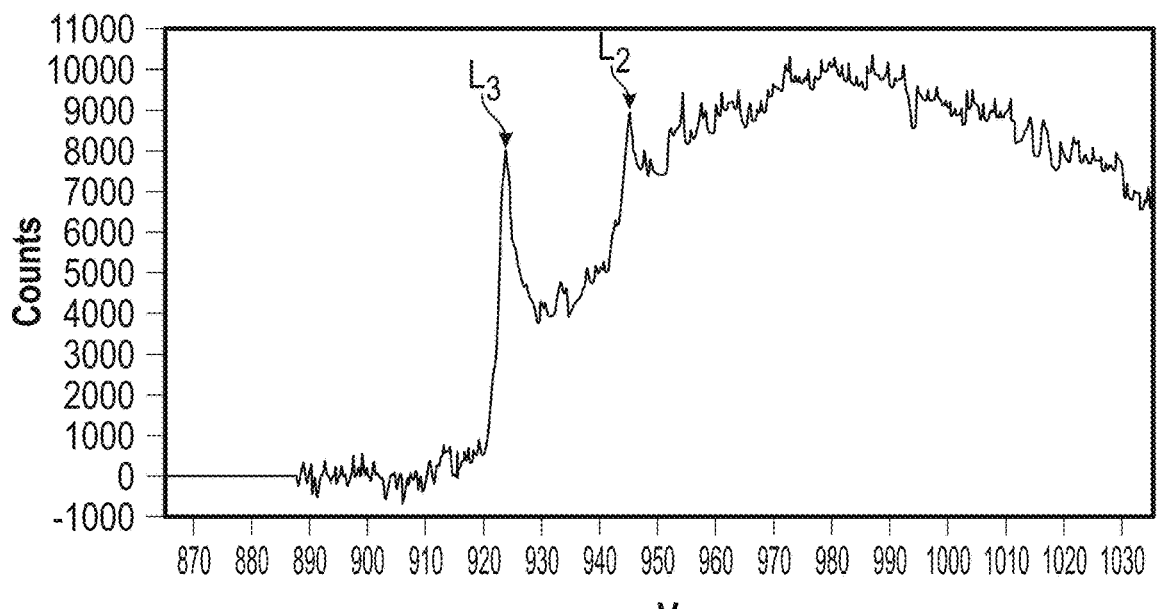
FIG. 15 is an Electron Energy Loss Spectroscopy (EELS) spectrum of the Cu-containing nanoparticles showing the Cu $L_{2,3}$ edge providing evidence that the Cu in these particles is primarily in the Cu(I) oxidation state with contributions by Cu(0) according to various embodiments.

Although most of the correlations corresponding to β-ether units in the aliphatic region remained intact, correlations for the corresponding oxidized analogues A' provide further evidence of benzylic oxidation. It is not fully understood how other lignin structures, such as β-5-linked units (phenylcoumarin), and β-β-linked (resinol) units (See FIGS. 14I and 14J), react. However, such structures remained intact in this fraction. It was also observed that cinnamaldehyde end groups (X1) were completely absent from the oxidized lignin samples, whereas benzaldehyde end groups (X2) remained. Monomeric and oligomeric fragments with aryl-aldehyde and aryl-acid structures are known to be present in milled wood lignins following catalytic oxidation, and also in lignosulfonates (i.e., lignins derived from acid sulfite pulping of wood). Although the aromatic ring is inactivated toward oxidation due to carbonyl conjugation, the aryl α-carbonyl is susceptible to nucleophilic attack by hydroxyl groups followed by cleavage of the side-chain $C_\alpha$-$C_\beta$ bond. Such cleavage decreases the molecular weight of polymeric lignin and creates hydrophilic lignin fragments with benzoate and benzaldehyde end-groups, consistent with the MS data (FIG. 4A).

It was also observed that lignin depolymerization was not extensive for pretreatment by Cu-catalyzed AOP. Using known peak integration methods, it was observed that the β-O-4, β-5 and β-β linkages were still present in both the solubilized lignin (FIG. 13C) and in the residual pretreatment-insoluble lignin (FIG. 13E) in approximately the same ratio as in the native lignin. Together with the low yields of aromatic monomers observed in LC-MS (FIG. 4A) and the SEC studies performed in this example that revealed an increase in solubilized lignins without a noticeable shift in the molecular weight distributions (FIG. 12), these NMR results strongly support a pathway in which Cu-catalyzed AOP pretreatment solubilizes and removes a fraction of the cell wall-bound lignin with minimal depolymerization and minimal oxidation of the residual lignin.

The solubilized lignins (FIGS. 13C and 13D) showed minimal depolymerization, exhibited minor oxidative modification, and contain soluble xylan oligosaccharides (not shown) unless these are further hydrolyzed and converted. The residual, pretreatment-insoluble lignin (FIGS. 13E and 13F) exhibited minimal modification as a consequence of the pretreatment with structures closely resembling native lignins (albeit requiring recovery of bipyridine). Furthermore, by controlling the pretreatment time and the oxidation stoichiometry, it might be possible to control the molecular weight and chemical properties of solubilized lignins, customizing them for the production of functional materials and fine chemicals with targeted properties.

Conclusions

These results provide insights into the structural changes that occur to the cell wall and cell wall biopolymers following Cu-catalyzed AOP pretreatment of hybrid poplar. Specifically, the catalyzed pretreatment resulted in disrupted cell walls manifested by dislocations between individual cell walls, as well as delaminations within cell walls. Additionally, copper-containing nanoparticles are co-localized within these zones of disruption.

It is hypothesized that sorption of catalyst into the cell wall during pretreatment results in oxidation, solubilization, and removal of lignin causing observable cell wall disruptions and enhanced susceptibility to enzymatic hydrolysis. Consistent with this hypothesis, both LC-MS and NMR characterization of the solubilized lignins and the residual material following Cu-catalyzed AOP pretreatment revealed the presence of oxidized lignin fragments. Specifically, a fraction of the hydroxyl groups at the α-carbon in β-O-4 units were oxidized to carbonyls, and end-groups characteristic of hydrolytic cleavage of oxidized lignin side-chains were created, suggesting that depolymerization results in lignin solubilization and removal during the pretreatment. Whereas the pretreatment-solubilized lignins exhibited a more than three-fold increase in the oxidation of the benzylic alcohol relative to native lignin (with correlation peak integrals increasing from 5% to 18%), the extent of lignin oxidation was limited in the pretreatment-insoluble lignin, which resembled native lignins.

Formation of the Cu-containing nanoparticles with oxidation states of Cu(I) and Cu(0) lower may be attributed to reduction of soluble Cu(bpy) complexes during pretreatment, although it is possible that these particles were formed during sample preparation. Additionally, relative to the lignins generated during other pretreatments and/or delignification processes that were performed at elevated temperatures, substantial lignin modification was often the result. Furthermore, the mildly oxidized lignins generated retained features closely resembling native lignins, which may provide added value to an integrated biorefining process.

Example 11

Biomass and Compositional Analysis

Hybrid poplar (*Populus nigra* var. charkoviensis×caudina cv. NE-19) grown at the University of Wisconsin Arlington Agricultural Research Station was milled to pass through a 1 mm screen (Circ-U-Flow model 18-7-300, Schutte-Buffalo Hammermill, LLC). The initial composition of structural carbohydrates and acid-insoluble lignin (Klason lignin) of biomass were determined using the NREL two-stage acidolysis method (Sluiter et al. 2011).

Catalytic Copper-Catalyzed AOP Pretreatment (Cu-AOP)

Biomass 0.51 g (about 0.5 g dry basis; from about 3 to about 5% moisture content) was pretreated in a total of 5 mL aqueous solution (10% solids loading). The standard Cu-AOP pretreatment reaction was carried out by adding 4330 μL of distilled water followed by 270 μL 5 M NaOH (100 mg/g biomass), 125 μL of a 40 mM $CuSO_4$ solution, and 125 μL of a solution containing both 40 mM $CuSO_4$ and 160 mM 2,2-bipyridine (bpy) (2 mM $Cu^{2+}$ and 4 mM bpy final concentration) and finally 150 µL of 30% $H_2O_2$ (w/w) (100 mg/g biomass) to the biomass. Reactants were briefly vortexed and the slurry was incubated with orbital shaking at 180 rpm and 30° C. for 24 hrs. The initial pH for the Cu-AOP pretreatment reaction was approximately 11.5.
"Slow Addition of Hydrogen Peroxide" (SH) with Cu-AOP Pretreatment (SH/Cu-AOP)

SH/Cu-AOP pretreatment was performed as described above for standard Cu-AOP except that the 150 µL 30% $H_2O_2$ (w/w) (100 mg/g biomass) was added to the reaction mixture slowly over a 10 hour period. Specifically, each hour 15 µL of 30% $H_2O_2$ was added to the reaction mixture, followed by brief mixing in a vortex mixer to ensure an even distribution. Following the final addition of $H_2O_2$, the mixture was incubated as described for an additional 14 hrs (24 hrs total reaction time).
Alkali Pre-Extraction (AP) with Cu-AOP Pretreatment (AP/Cu-AOP)

Alkali pre-extracted hybrid poplar was prepared by incubating 0.51 g (approximately 0.5 g dry basis) of biomass in 270 µL of 5 M NaOH (100 mg/g biomass) at 30° C. for 1 hr, (10% solids loading). After 1 hour of incubation, the remaining insoluble biomass was washed with one volume of deionized water and subjected to 23 hrs of Cu-AOP pretreatment (24 hrs total reaction time including the 1 hour pretreatment) as described above.
Combined AP and SH with Cu-AOP Pretreatment (AP-SH/Cu-AOP)

Alkali pre-extraction and slow $H_2O_2$ addition strategies were combined in the modified Cu-AOP (AP-SH/Cu-AOP) pretreatment. Alkali pre-extracted biomass (0.51 g or 0.5 g dry weight) was subjected to SH/Cu-AOP as described above except that the concentration of the Cu(bpy) complexes was reduced by 50% (i.e. 1 mM Cu and 2 mM bpy total final concentrations). Whenever a different concentration of any of the reactants was used to probe the effect on the pretreatment process, an appropriate amount of distilled water was added to the reaction mixture to maintain a final solid biomass loading of 10%.
Enzymatic Hydrolysis Following pretreatment, 0.5 mL of 1 M citric acid buffer (pH 5) was added to the pretreatment mixture, and the slurry was slowly titrated with 72% (w/w) $H_2SO_4$ to adjust the pH to 5 prior to enzymatic hydrolysis. An enzyme cocktail consisting of Cellic CTec3 and HTec3 (kindly provided by Novozymes A/S, Bagsværd, DK) at a loading of 30 mg protein/g glucan each unless otherwise noted was added to the hydrolysis reaction. The protein concentrations of the stock enzyme cocktails were quantified by determining the total protein concentration (and subtracting the non-protein nitrogen contribution) using the Kjeldahl nitrogen analysis method (AOAC Method 2001.11, Dairy One Cooperative Inc., Ithaca, N.Y., USA). The total volume of the enzymatic hydrolysis reaction was then adjusted to 10 mL by the addition of deionized water, and the samples were incubated at 50° C. for 72 hrs with orbital shaking at 210 rpm. Following enzymatic hydrolysis, the solid and liquid phases were separated by centrifugation, and the amount of glucose and xylose released into the aqueous phase was quantified by HPLC (Agilent 1260 Series equipped with a Agilent 1260 infinity refractive index detector) using an Aminex® HPX-87H column operating at 65° C., a mobile phase of 0.05 M $H_2SO_4$, and a flow rate of 0.6 mL/min. Standard curves using pure glucose and xylose were prepared prior to each analysis to convert peak area to concentration of monomeric sugar. The yield of glucose and xylose released was defined as the amount of solubilized monosaccharide divided by the total sugar content of the biomass prior to pretreatment as determined by chemical composition analysis. The error bars in the figures represent the standard deviation from three or more biological replicates.

Results and Discussion

Slow Addition of $H_2O_2$ (SH/Cu-AOP)

It was hypothesized that by lowering the effective $H_2O_2$ concentration during AOP treatment, a decrease in non-productive reactions would occur, thus enabling more of the reactive oxygen species to react with the biomass. To test this hypothesis, the

TABLE 3

Sugar yields obtained from different pretreatment strategies

| Method | Glucose yields (%) | Xylose yields (%) |
|---|---|---|
| Cu-AOP | 62 | 75 |
| AP/Cu-AOP | 86 | 95 |
| SH/Cu-AOP | 77 | 93 |
| AP-SH/Cu-AOP | 97 | 94 |

Figure 16:
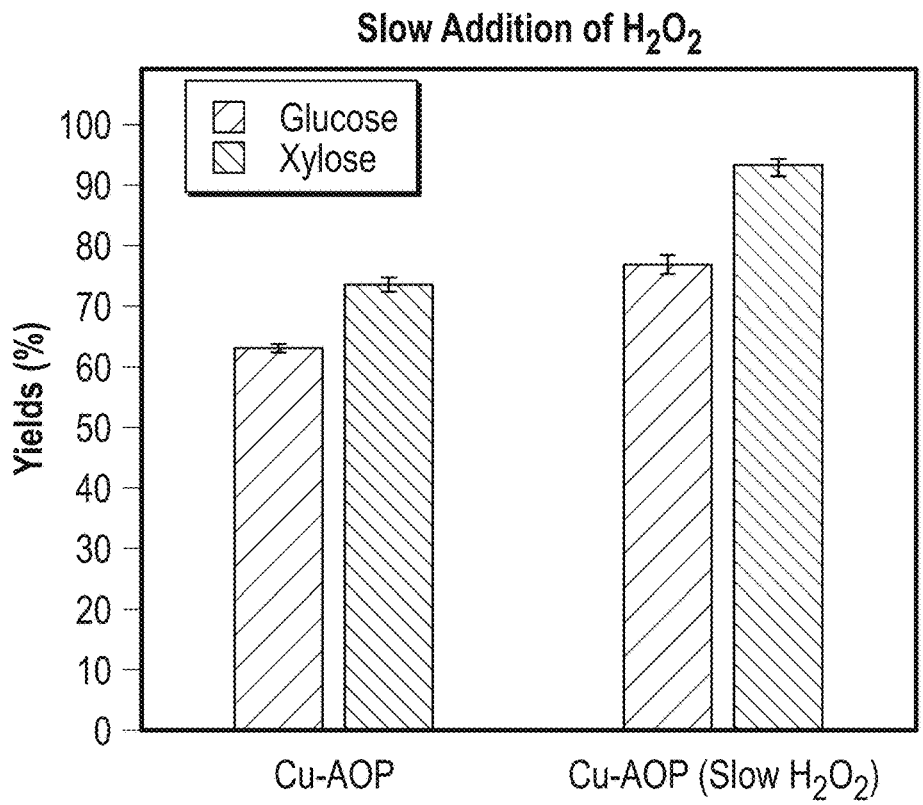
FIG. 16 is a graph comparing yields of xylose and glucose when using catalytic AOP with a batch addition of hydrogen peroxide versus a slow addition of hydrogen peroxide according to an embodiment.

$H_2O_2$ was added in a "slow add" manner. Specifically, the $H_2O_2$ was added over the course of 10 hrs, without changing either the total amount of peroxide utilized or the pretreatment time (SH/Cu-AOP). Relative to Cu-AOP conditions, this modification of the rate of addition of oxidant resulted in a greater than 1 fold increase in sugar yields, namely an approximately 1.2 fold increase (77% glucose and 93% xylose) following enzymatic hydrolysis (See FIG. 16 and Table 3 below).

Figure 17:
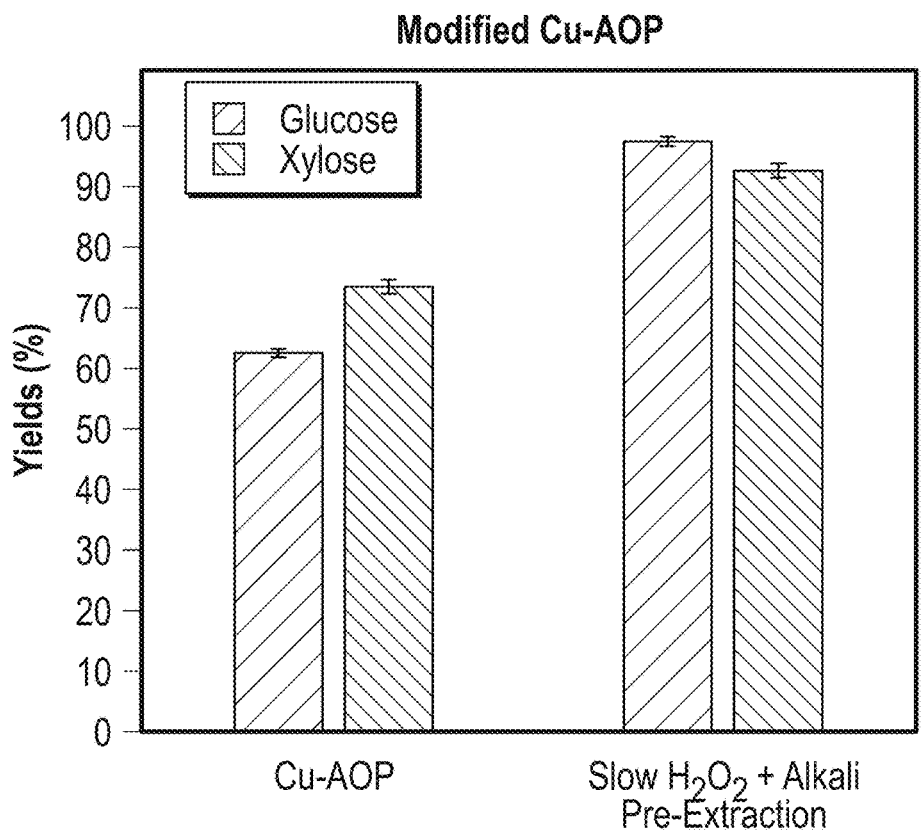
FIG. 17 is a graph comparing yields of xylose and glucose yields when using catalytic AOP with a batch addition of hydrogen peroxide versus a slow addition of hydrogen peroxide in combination with alkali pre-extraction in a modified Cu-AOP pretreatment according to an embodiment.

To ascertain how SH/Cu-AOP alters the cell wall of hybrid poplar relative to standard Cu-AOP, compositional analysis of the biomass was performed both before and after pretreatment. These results showed that the major impact of slow addition of $H_2O_2$ was an increase in the extent of lignin removal, with approximately 44% of the original lignin being solubilized during SH/Cu-AOP compared to 28% during Cu-AOP (FIG. 17 showing an increase in the yields of glucose and xylose to 96% and 93%, respectively, (Table 4). As discussed herein, lignin removal is a significant factor in overcoming biomass recalcitrance and improving sugar yields, by improving access to the cellulose. This aspect of lignin removal may help explain why the more efficient utilization of $H_2O_2$ in SH/Cu-AOP significantly increased the efficacy of pretreatment and subsequently the final sugar yields.

TABLE 4

Percent mass loss obtained different pretreatments

| Pretreatments of hybrid poplar | Glucan loss (%) | Xylan loss (%) | Lignin loss (%) |
|---|---|---|---|
| Untreated | N/A | N/A | N/A |
| Normal Cu-AOP | 3 ± 0.03 | 23 ± 0.01 | 28 ± 0.4 |
| AP | 1 ± 0.9 | 5 ± 0.3 | 5 ± 0.4 |
| AP/Cu-AOP | 5 ± 1.2 | 32 ± 0.3 | 40 ± 1.4 |
| SH/Cu-AOP | 6 ± 0.8 | 23 ± 0.5 | 44 ± 0.00 |
| AP-SH/Cu-AOP | 6 ± 1.5 | 39 ± 0.4 | 56 ± 0.3 |

Lignin: Acid insoluble Klason lignin
Untreated: Untreated hybrid poplar
AP: Alkali pre-extraction only
AP/Cu-AOP: Cu-AOP followed by alkali pre-extraction
SH/Cu-AOP: Cu-AOP pretreatment with slow addition of $H_2O_2$
AP-SH/Cu-AOP: Combining alkali pre-extraction and slow addition of $H_2O_2$ with Cu-AOP Alkali Pre-Extraction Followed by Cu-AOP (AP/Cu-AOP)

Seeking to increase further the efficiency of the pretreatment and to improve the accessibility of the cellulases and hemicellulases to the polymeric sugars, an alkali pre-extraction step was incorporated prior to Cu-AOP (AP/Cu-AOP). By removing easily extracted hemicellulose and lignin, it was thought that the porosity of the biomass would increase, resulting in improved penetration of the Cu(bpy) complexes into the plant cell wall. This, in turn, may lead to efficient activation and utilization of active radical species. In addition, such a step may also remove extractives and lignin to reduce inhibition of enzymes during enzymatic hydrolysis step.

Figure 2:
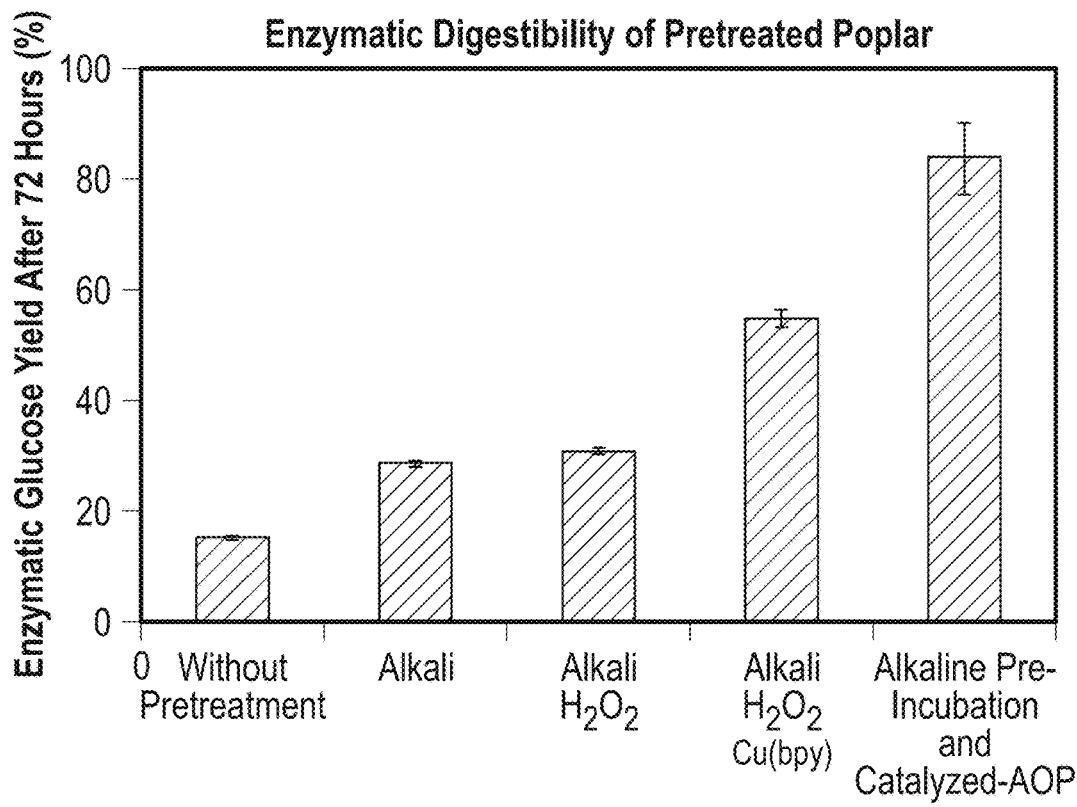
FIG. 2 is a graph showing enzymatic digestibility of pretreated poplar according to an embodiment.

Based on the final sugar yields, the alkaline pre-extraction step had a large positive impact on enzymatic digestibility. Compared to standard Cu-AOP pretreatment of hybrid poplar, AP/Cu-AOP pretreatment resulted in improved glucose yields from 62% to 86% (an approximately 1.4 fold increase), while xylose yields also improved from 75% to 93% (an approximately 1.2 fold increase) (Table 3). Compositional analysis following alkali pre-extraction of hybrid poplar indicated that while approximately 5% by weight of both the lignin and xylan was solubilized during pre-extraction (FIG. 17, Table 4), substantially none or only trace amounts of the glucose was released. Cu-AOP pretreatment of this alkali pre-extracted poplar (AP/Cu-AOP) resulted in loss of an additional approximately 35% lignin, which is about 1.4 times higher than Cu-AOP alone. The removal of lignin is synergistic with AP/Cu-AOP, removing nearly 10% more than the sum of AP and Cu-AOP alone, consistent with the significant increase in sugar yields following enzymatic hydrolysis of AP/Cu-AOP poplar (FIG. 2).

Hypothesizing that alkaline pre-extraction aids pretreatment, in part, by preparing the biomass for pretreatment i.e., swelling the biomass and increasing the surface area for enzyme accessibility, the water retention value (WRV) was measured both before and after pre-extraction. Results showed that the WRV of hybrid poplar increased from 1.15 g water/g biomass (untreated) to 1.5 g water/g biomass following alkali pre-extraction step, consistent with the importance of WRV to the pretreatment process.

To ascertain if alkali pre-extraction reduced enzyme inhibition by removing extractives and lignin, the effect of pre-extraction liquor on the hydrolysis of Avicel® was evaluated. These results demonstrated that enzymatic hydrolysis of Avicel® in the presence of alkali pre-extraction liquor resulted in 6% lower glucose yields compared to hydrolysis reactions that did not contain the pre-extraction liquor. Hydrolysis reactions were also performed in the presence of pretreatment liquors obtained from normal Cu-AHPAOP and AP/Cu-AHPAOP. Interestingly, the inhibitory effect of the Cu-AHPAOP pretreatment liquor was approximately equal to additive inhibitory effect of the AP pre-extraction liquor plus the AP/Cu-AHPAOP pretreatment liquor. Together, these results suggest that pre-extraction of the hybrid poplar with NaOH increases sugar yields by removing alkali extractable compounds that inhibit enzymatic hydrolysis.

In summary, alkali pre-extraction prior to Cu-AHPAOP pretreatment (AP/Cu-AHPAOP) results in increased glucose and xylose yields relative to our standard Cu-AHPAOP process, presumably by These data are consistent with results from Yuan et al. [30] demonstrating efficient and synergistic lignin and hemicellulose removal from poplar using a two-step alkali and ionic liquid pretreatment. In addition, Liu et al. [26] recently reported enhanced enzymatic hydrolysis of corn stover by coupling alkaline pre-extraction with alkaline-oxidative post-treatment.

Combining Alkali Pre-Extraction and Slow Addition (AP-SH/Cu-AOP)

Having demonstrated that the efficacy of Cu-AOP could be improved dramatically by slowly adding the $H_2O_2$ over the course of 10 hrs (SH/Cu-AOP), as well as by pre-extracting the poplar with alkali prior to Cu-AOP (AP/Cu-AOP), a combination of the two strategies (AP-SH/Cu-AOP). As shown in Table 3, these two modifications to the Cu-AOP pretreatment of hybrid poplar procedure resulted in the removal of nearly 40% of the xylan and over 55% of the lignin during pretreatment. As expected, this increase in lignin and xylan (hemicellulose) removal resulted in a significant improvement in enzymatic digestibility (FIG. 17). In fact, enzymatic hydrolysis resulted in high sugar yields of 97% and 94% of the theoretical maximum for glucose and xylose, respectively.

This AP-SH/Cu-AOP pretreatment strategy was performed at atmospheric pressure near room temperature. As a result, the AP-SH/Cu-AOP pretreatment can be performed using relatively simple and inexpensive equipment.

Optimization of AP-SH/Cu-AOP Pretreatment

Figure 18:
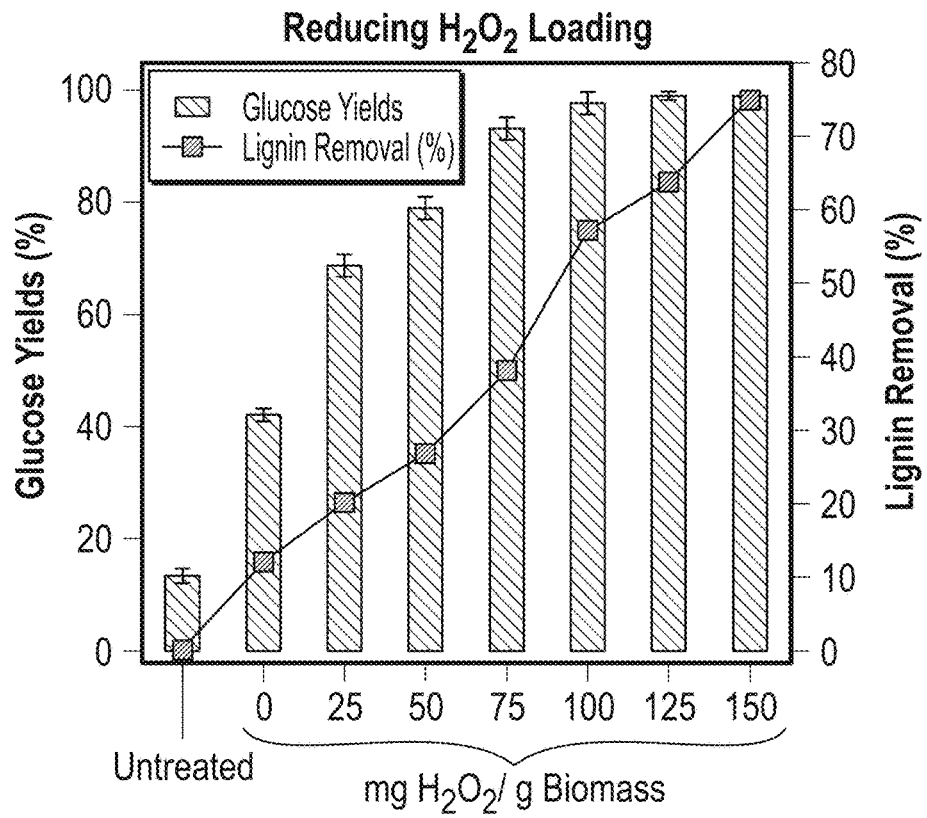
FIG. 18 is a graph showing the correlation between lignin removal and glucose yields with different concentrations of slowly added $H_2O_2$ in combination with alkali pre-extraction in a modified Cu-AOP pretreatment according to an embodiment.

Hypothesizing that these two modifications to the Cu-AOP pretreatment process might allow a reduction in delignification costs by lowering oxidant loadings, a series of experiments were performed with varying $H_2O_2$ loadings (FIG. 18). The results demonstrated that the $H_2O_2$ loading can be reduced by 25% to 75 mg/g poplar while still maintaining sugar yields of over 90%. Even at $H_2O_2$ loadings as low as 50 mg $H_2O_2$/g biomass, the sugar yields following enzymatic hydrolysis were higher (78%) than those obtained with normal Cu-AOP which utilizes 100 mg/g biomass (62%).

As expected, compositional analysis of the biomass treated with different $H_2O_2$ loadings revealed a clear relationship between the extent of lignin removal during AP-SH/Cu-AOP and the sugar yields following enzymatic hydrolysis (FIG. 18). Sugar yields increased rapidly with lignin removal until approximately 40% of the lignin had been removed, at which point additional lignin removal had only a modest effect on sugar yields. This digestibility "threshold" value in between a Klason lignin content of 10-15% may be the point where cell wall loses its enough recalcitrance to allow enzyme accessibility.

Figure 19:
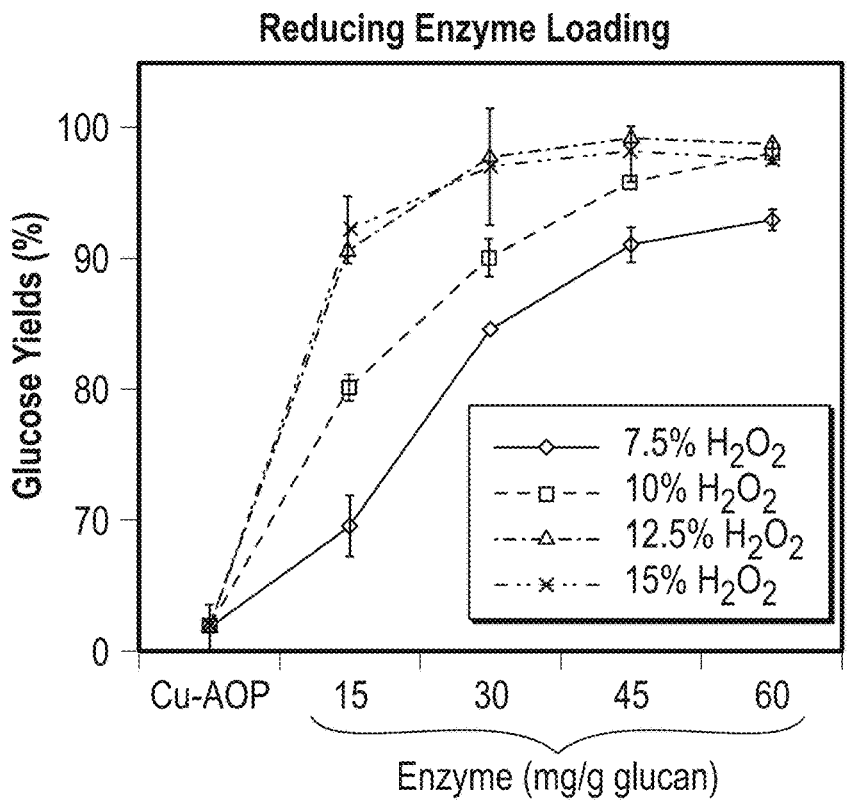
FIG. 19 is a graph showing glucose yields obtained with different concentrations of enzymes at different loadings of $H_2O_2$ on biomass utilizing a modified Cu-AOP pretreatment according to an embodiment.

The experiments described above were performed utilizing 60 mg protein (enzyme) per g glucan. Hypothesizing that the alkali pre-extraction and the more efficient utilization of $H_2O_2$ may allow for a reduction in enzyme loading, a series of studies were performed to correlate glucose yields following enzymatic hydrolysis of pretreated hybrid poplar using different enzyme loadings (FIG. 19). Not surprisingly, there was a strong correlation between enzyme loading and sugar yield. As predicted, however, AP-SH/Cu-AOP method resulted in improved sugar yields even at much lower enzyme concentrations. For instance, at 100 mg $H_2O_2$ per gram poplar (10% $H_2O_2$), enzyme loadings were reduced to 15 mg/g glucan (a four-fold decrease) with higher glucose yields following enzymatic hydrolysis (approximately 80% versus 60% for our "standard" Cu-AOP conditions). In addition, when the peroxide loadings were increased during pretreatment to 125 mg $H_2O_2$/g biomass, glucose yields increased to >90% while still utilizing only 15 mg enzyme/mg glucan. This improved saccharification of poplar wood with such low enzyme loadings can be attributed to the relatively high lignin removal during the AP-SH/Cu-AOP pretreatment process.

Figure 20:
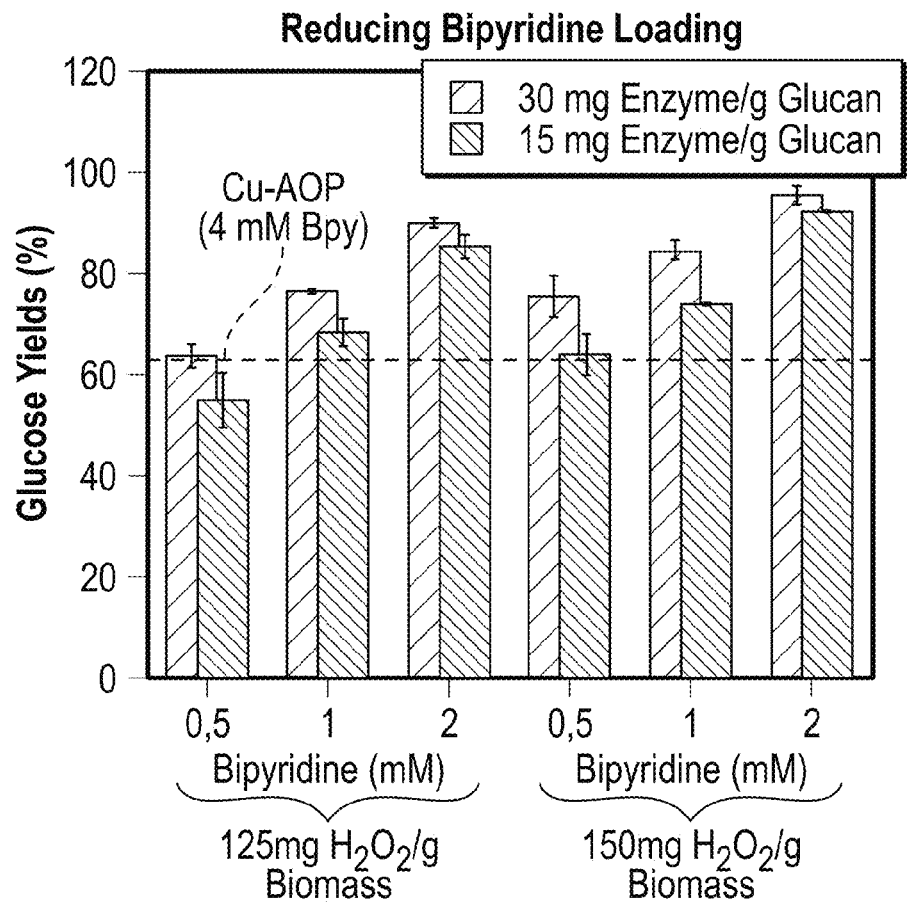
FIG. 20 is a graph showing glucose yields obtained with different concentrations of bipyridine at different loadings of $H_2O_2$ and enzymes on biomass utilizing modified Cu-AOP pretreatment according to an embodiment.

As demonstrated in FIG. 19, AP-SH/Cu-AOP at $H_2O_2$ loadings of 100-150 mg/g biomass removed a substantial amount of lignin from the biomass. This provided an insight of possibility to decrease the concentrations of other costly components involved in Cu-AOP pretreatment, such as bpy Above discussed strategies for improving pretreatment were performed using 2 mM concentration of bpy. Trials were carried out to select minimum concentration of bpy but still having relatively high sugar yields. FIG. 20 shows sugar yields obtained at different concentrations of bpy, utilizing 125 and 150 mg $H_2O_2$. Results revealed the potential of low concentrations of bpy at low enzyme loadings of 15 and 30 mg/g glucan. A high glucose yields of 75% were obtained at 0.5 mM concentration of bpy with 30 mg/g glucan enzyme and 150 mg $H_2O_2$. An increase in the yields to 85% was obtained by increasing the bpy to 1 mM with 30 mg/g glucan enzyme and 150 mg $H_2O_2$. These results shows the potential of AP-SH/Cu-AOP at low bpy loadings. By performing cost analysis of the data, we could figure out the best combinations of the component concentration to lower the cost and maintaining high sugar yields.

Lignin Stream

Figure 21:
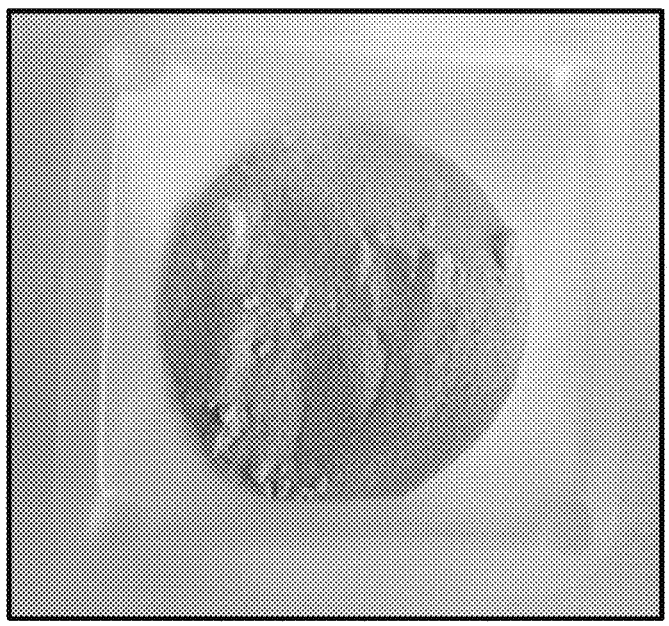
FIG. 21 is an image of lignin after the biomass in which it was located was subject to a Cu-AOP pretreatment according to an embodiment.

As shown in FIG. 19, AP-SH/Cu-AOP pretreatment solubilized a significant fraction of the total lignin present in hybrid poplar. Recognizing that this delignification process not only improves the enzymatic digestibility of the biomass, but also provides a lignin stream for potential valorization to chemicals and/or fuels, we sought to characterize the solubilized lignin. The solubilized lignin was precipitated at pH 2, washed with deionized water, and lyophilized to dryness. The recovered product contained ≥90% Klason lignin, with only 3% xylan and 2% ash content. (See FIG. 21).

Example 12

Study on Cell Wall Properties of Natural *Populus* Variants for Enhanced Digestibility with Alkaline Hydrogen Peroxide Pretreatment In this study, the effect of cell wall redox metal ions, lignin content and S/G ratio on the efficacy of alkaline pretreatments was studied. The results obtained were correlated to digestibility i.e., sugar release from biomass followed by enzymatic hydrolysis.

Materials and Method

Biomass

Thirty-six *Populus trichocarpa* genotypes were provided by Oak Ridge National Laboratory, Oak Ridge, Tenn., USA. Biomass was milled (Wiley, MiniMill, Thomas Scientific, Swedesboro, N.J.) to pass through 20 mesh size screen, air dried, and stored in airtight bags prior to pretreatment studies.

Biomass Analysis

The initial composition of structural carbohydrates and acid-insoluble lignin (Klason lignin) were determined using the NREL two-stage acidolysis method (Sluiter et al. 2011) with modifications as described in Li M Y, Foster C, Kelkar S, Pu Y Q, Holmes D, Ragauskas A, Saffron C M, Hodge D B: Structural characterization of alkaline hydrogen peroxide pretreated grasses exhibiting diverse lignin phenotypes. *Biotechnol Biofuels* 2012, 5:38. The S/G ratio for all samples were determined by thioacidolysis as described in Li et al., 2012.

Quantification of redox-active metals in different popular species were determined by inductively coupled plasma mass spectrometry (ICP-MS) performed at A & L Great Lakes Laboratories.

Pretreatment

Each biomass 0.51 g (approximately 0.5 g dry basis; about 3 to about 5% moisture content) was pretreated with three pretreatments viz alkali, alkaline hydrogen peroxide (AOP) and AOP pretreatment aided with Cu (bpy) catalyst (Cu-AOP) in a total of 5 mL aqueous solution (10% solids loading). For alkali-only pretreatment, the solution contained 50 mg NaOH (100 mg NaOH/g biomass), while AOP pretreatment also contained 150 μL of 30% $H_2O_2$ (100 mg $H_2O_2$/g biomass). The Cu-AOP pretreatment solution was prepared as described above for AOP except that 125 μL of a solution containing 40 mM $CuSO_4$ as well as 125 μL of a solution containing both 40 mM $CuSO_4$ and 80 mM 2,2-bipyridine (bpy) were added to the biomass slurry after the addition of NaOH (2 mM $Cu^{2+}$ and 4 mM bpy final concentration) but prior to the addition of $H_2O_2$. The final pH for the alkali-only pretreatment was 13.2, while it was approximately 11.5 for AOP and Cu-AOP due to the addition of $H_2O_2$. For all three pretreatments, the reactants were vortexed and the slurry incubated with orbital shaking at 180 rpm at 30° C. Solutions containing only biomass and deionized water acted as the control.

Enzymatic Hydrolysis

After pretreatment, 0.5 mL of 1 M citric acid buffer (pH 4.8) was added to the pretreated slurry, and the slurry was slowly titrated with 72% (w/w) $H_2SO_4$ to adjust the pH to 5.0 prior to enzymatic hydrolysis. An enzyme cocktail consisting of Cellic CTec3 and HTec3 (gift from Novozymes A/S, Bagsværd, DK) at a loading of 30 mg protein/g glucan each was added to the hydrolysis reaction. (The protein concentrations of the stock enzyme cocktails were quantified using the Bradford Assay (Sigma-Aldrich)). The total volume was adjusted to 10 mL by the addition of deionized water, and the samples were incubated at 50° C. with orbital shaking at 210 rpm. Following enzymatic hydrolysis, the solid and liquid phases were separated by centrifugation, and the amount of glucose and xylose released into the aqueous phase was quantified by HPLC (Agilent 1260 Series equipped with an Aminex® HPX-87H column operating at 65° C., a mobile phase of 0.05 M $H_2SO_4$, a flow rate of 0.6 mL/min, and detection by refractive index). The yield of glucose and xylose released was defined as the amount of solubilized monosaccharide divided by the total sugar content of the biomass prior to pretreatment as determined by chemical composition analysis. Although xylan is solubilized during pretreatment, no monomeric sugars were detected in the pretreatment liquor. The error bars in the figures represent the standard deviation from ≥three biological replicates.

Chelation of Inorganic Ions from Native Biomass

Biomass (3 g) was mixed with 30 mL of 0.2% (w/v) of the chelator diethylenetriaminepentaacetic acid (DTPA). The pH of the slurry was adjusted to 7.0 with 5M NaOH, and the solution was incubated for 24 hr at 30° C. The biomass was then washed thoroughly with 10 volumes of distilled $H_2O$ to remove the DTPA, dried at room temperature for 2 days, and stored in airtight bags. Biomass incubated for 24 hr at 30° C. with only distilled water was used as a control.

Pretreatment reactions were performed either in the presence of bpy plus $Cu^{2+}$, $Mn^{2+}$, or $Fe^{2+}$ ([metal]:[bpy]=2 mM: 4 mM) or in the absence of added metal to ascertain the effect these ions had on the pretreatment of chelated woody biomass.

Twenty (20) samples of a natural population of *Populus trichocarpa* trees were obtained from Oak Ridge National Laboratory, out of which 16 were separated into two fractions individually on the basis of growth, i.e. early growth (EGW) and late growth (LGW) wood samples, which made total number of samples to 32. Lignin content, S/G ratio and cell wall redox metal ions content were quantified to perform correlation studies. Correlations were established between final sugar release after enzymatic hydrolysis and different pretreatments among different poplar samples.

Results

Sixteen (16) samples out of 20 samples were separated into two fractions on the basis of their growth i.e. early growth wood and late growth wood to study how cell wall properties of different ages of wood relates with wood digestibility. In total, 36 biomass samples were individually pretreated utilizing alkali, alkaline hydrogen peroxide (AOP), and copper catalyzed alkaline hydrogen peroxide pretreatment (Cu-AOP). To establish digestibility correlation among cell wall properties and different pretreatments, pretreated samples were enzymatically hydrolyzed using commercially available optimized cocktail of cellulases and xylanases. Samples without any pretreatment were also enzymatically hydrolyzed and analyzed.

Figure 23A:
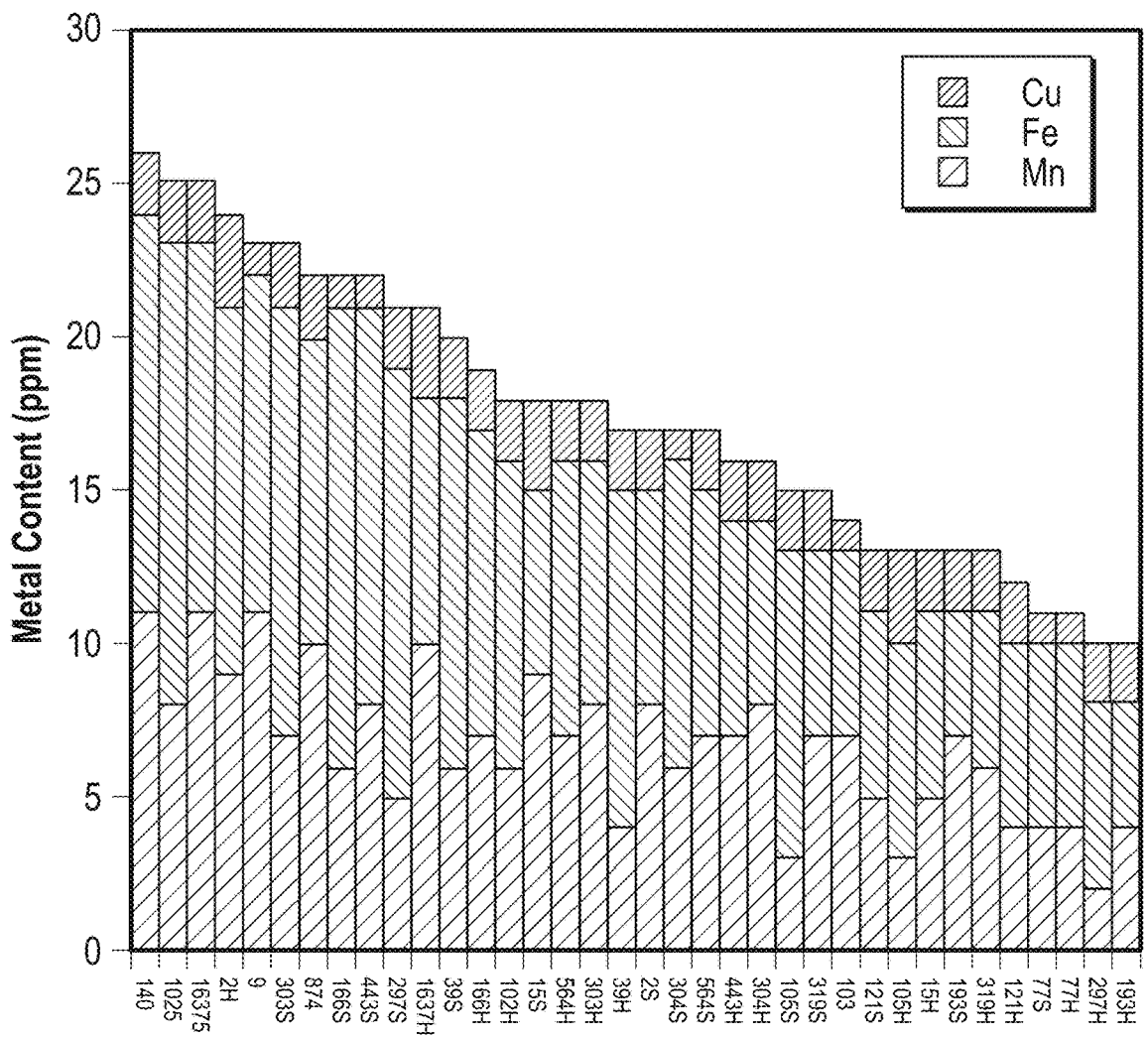
FIG. 23A is a graph showing metal content of various genotypes of *Populus trichocarpa* species according to an embodiment.
Figure 23B:
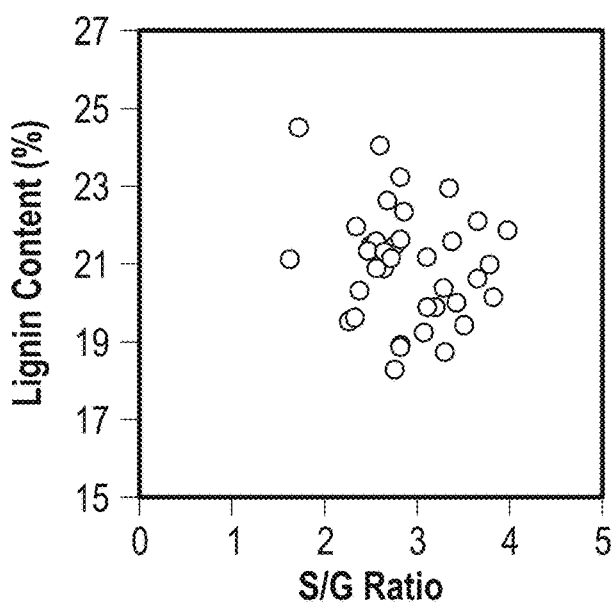
FIG. 23B is a graph showing lignin content vs guaiacyl and syringyl (S/G) ratio according to an embodiment.

To establish significant correlations, samples were analyzed to determine their lignin content, S/G ratio and total cell wall redox metal ions content. Estimated lignin content was in the range of 18.74 to 24.55%, S/G ratio was 1.62 to 3.98 (FIG. 23B) and metal content was in the range of 10 to 26 ppm (FIG. 23A).

Results demonstrated that for all 36 samples, Cu-AOP pretreatment yielded maximum sugars, followed by yields obtained with AOP, and untreated samples. Sugar yields with untreated samples were in the range from 13 to 38%, 61 to 85% with alkali pretreatment, about 53 to about 81% with AOP pretreatment and 74 to 94% for Cu-AOP pretreatment (FIG. 22).

Figure 22A:
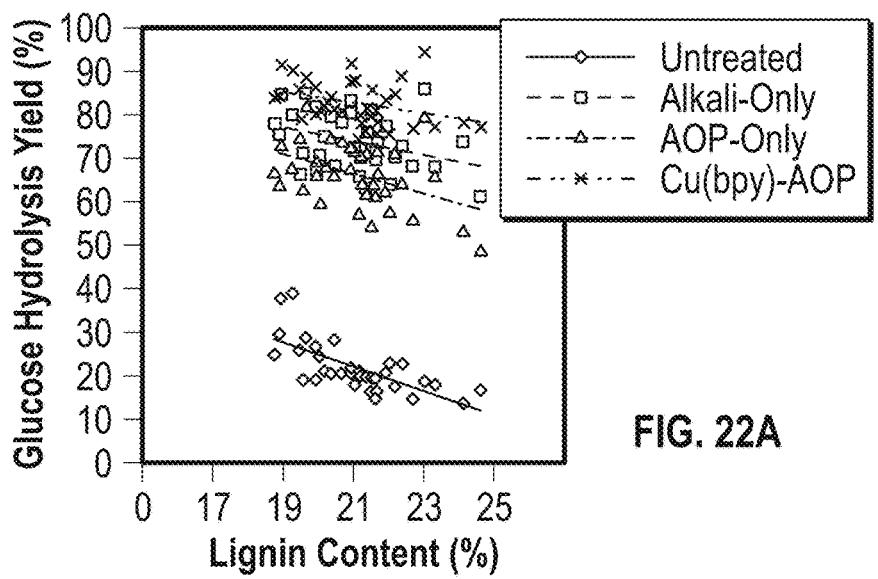
FIGS. 22A-22C are graphs correlating sugar yields with different cell wall properties according to an embodiment.
Figure 22B:
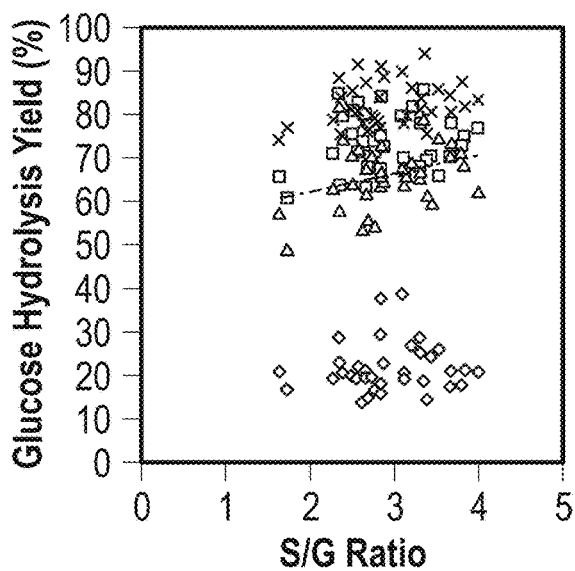
Figure 22C:
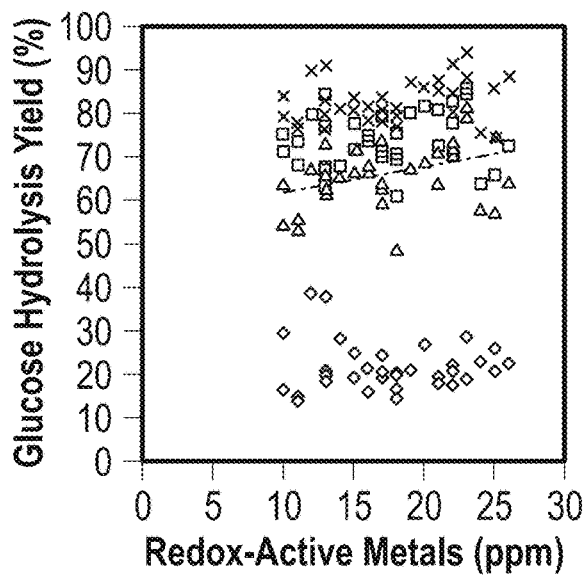

Specifically, as FIG. 22 shows, there is a negative correlation for lignin content in all pretreatments. Additionally, the S/G ratio correlation strongest for AOP-only treatment (p-value=0.055). The redox-active metal content was only significant for AOP-only treatment.

As demonstrated by the results, addition of copper catalyst led to substantial increase in the sugar yields, these surprising results provided an insight into the role of cell wall redox active metal ions in improving effectiveness of AOP only pretreatment.

A positive correlation was discovered between cell wall redox metal ions and sugar yields when biomass was treated with AOP only. Correlations were insignificant for cell wall metal ions when the biomass was pretreated with alkali and Cu-AOP. The results clearly demonstrated the importance of cell wall redox metal ions in AOP only method. While not wishing to be bound by this proposed hypothesis, it is thought that cell wall metal ions efficiently activated the hydrogen peroxide which catalyzed the formation of highly reactive radical species that aided in the pretreatment process. Correlation between S/G ratio and sugar yields was found to be strongest for AOP pretreated samples compared to alkali and Cu-AOP.

Chelation of the Biomass

Figure 24:
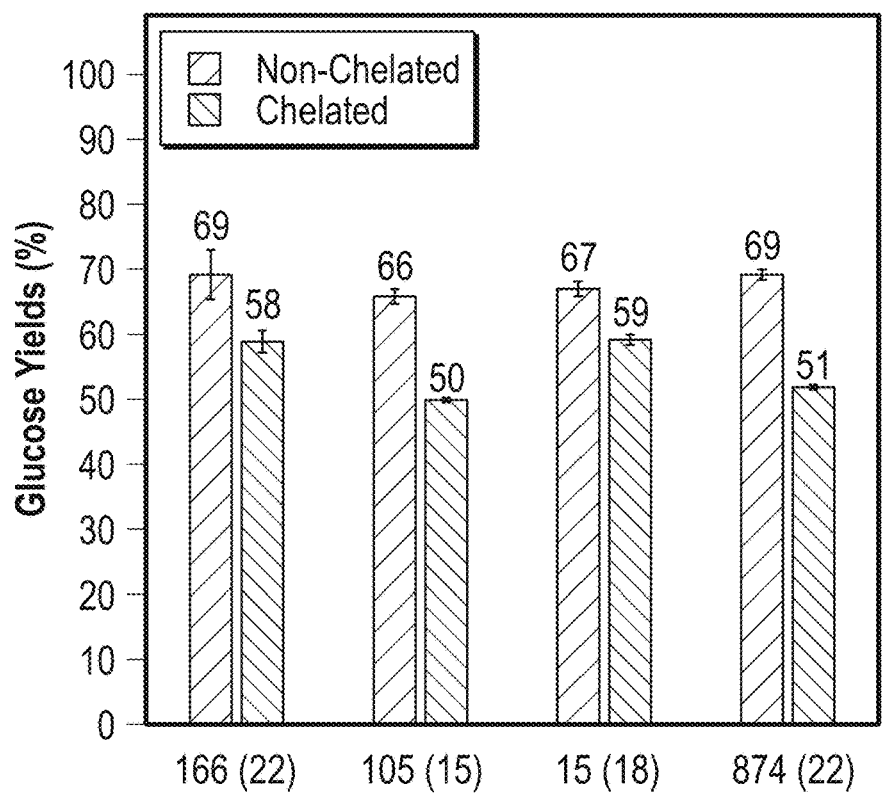
FIG. 24 is a graph showing glucose yields for various chelated and non-chelated for four different genotypes of *Populus trichocarpa* according to an embodiment.
Figure 25:
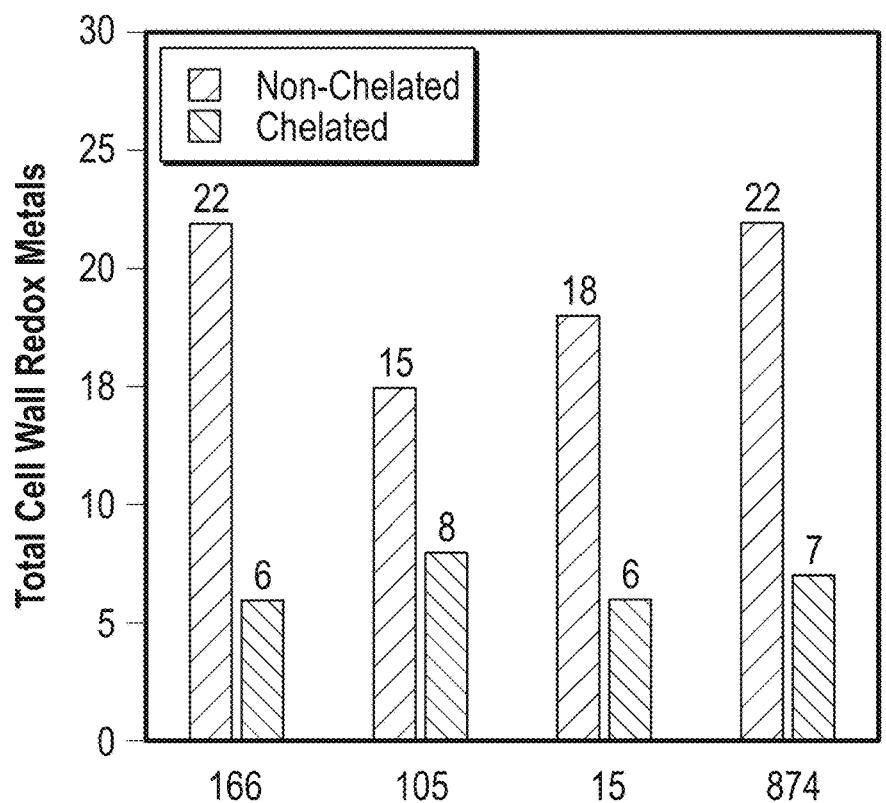
FIG. 25 is a graph showing total number of cell wall redox metal ions in various chelated and non-chelated for four different genotypes of *Populus trichocarpa* according to an embodiment.

To validate the relationship between intracellular metal content and efficacy of AOP pretreatment, each of the selected four samples was incubated with the metal chelator DTPA to remove the cell wall redox metal ions prior to pretreatment. Results revealed decreased sugar yields with chelated biomass compared to non-chelated biomass (FIG. 24). For example, glucose yields were reduced from 66% to 50% for sample 105. Similar trend was observed for the other biomass samples. To confirm the efficiency of chelation, ICP-MS analysis of the chelated biomass was performed. Results demonstrated reduced cell wall redox metal content compared to non-chelated biomass (FIG. 25).

Discussion

To further understand the mechanism of AOP pretreatment on woody biomass components, additional studies were carried out.

A total of 36 woody biomass samples were studied to determine the correlation between cell wall properties and fermentable sugar release. Analysis of results revealed that sugar release was negatively correlated to lignin content of the biomass. Lignin serves as a physical blockage on the surface of the biomass and chemical blockage through lignin carbohydrate complex. Adsorption of enzymes on lignin occurs through hydrophobic interactions, electrostatic interactions, and/or hydrogen-bonding interactions, which leads to non-productive binding making cellulose inaccessible to enzymes.

In addition to lignin, lignin composition, i.e., the S/G ratio, was also analyzed, with results confirming the absence of any correlation of S/G rations with the sugar yields. This is in contrast to other reported results, which may be explained by use of a different pretreatment processes.

The effect of total cell wall redox metal ions (Cu, Mn, and Fe) on the digestibility of biomass treated with AOP only. Interestingly, positive correlation was observed between glucose yields and number of metal ions for biomass treated with AOP only pretreatment whereas no correlations were established for alkali, Cu-AOP and untreated samples.

Example 13

Biomass

Hybrid poplar (*Populus nigra* var. charkoviensis×caudina cv. NE-19) was provided by the Great Lakes Bioenergy Research Center (GLBRC), sugar maple (*Acer saccharum*) was obtained from Todd Smith (Devereur sawmill, Pewamo, Mich.), silver birch (*Betula pendula*) was acquired from Curt Lindstrom (Smurfit-Kappa Kraftlina A B, Pitea, Sweden) and aspen (*Populus tremula×Populous tremuloides*) was obtained from Dr. Raymond Miller (Michigan state University Extensions). Biomass was milled using a Wiley MiniMill (Thomas Scientific, Swedesboro, N.J.) to pass through a 20-mesh size screen, air dried, and stored in airtight bags prior to pretreatment studies.

Compositional Analysis and S/G Ratios

Quantification of structural carbohydrates, acid-insoluble lignin (Klason lignin), cell wall metal content, and S/G ratio were performed as described in Example 12.

Pretreatment

Three different pretreatment strategies were tested on each of the biomass samples: alkali only, alkaline hydrogen peroxide (AOP), and copper-catalyzed AOP (Cu-AOP). In all cases, 0.51 g of biomass (approximately 0.5 g dry basis; about 3 to about 5% moisture content) was pretreated in a total of 5.0 mL aqueous solution (10% solids loading). For alkali-only pretreatment, the solution contained 50 mg NaOH (100 mg NaOH/g biomass), while AOP pretreatment also contained 150 µL of 30% $H_2O_2$ (100 mg $H_2O_2$/g biomass). The Cu-AOP pretreatment solution was prepared as described above for AOP except that 125 µL of a solution containing 40 mM $CuSO_4$ as well as 125 µL of a solution containing both 40 mM $CuSO_4$ and 160 mM 2,2-bipyridine (bpy) were added to the biomass slurry after the addition of NaOH (2 mM $Cu^{2+}$ and 4 mM bpy final concentration) but prior to the addition of $H_2O_2$. The final pH for the alkali-only pretreatment was 13.2, while it was approximately 11.5 for AOP and Cu-AOP due to the addition of $H_2O_2$. For all three pretreatments, the reactants were mixed in a vortex mixer and the slurry incubated with orbital shaking at 180 rpm and 30° C. for 24 hrs. Solutions containing only biomass and deionized water acted as controls.

Enzymatic Hydrolysis

Following pretreatment, 0.5 mL of 1 M citric acid buffer (pH 4.8) was added to the pretreated slurry, and the slurry was slowly titrated with 72% (w/w) $H_2SO_4$ to adjust the pH to 5.0 prior to enzymatic hydrolysis. An enzyme cocktail consisting of Cellic CTec3 and HTec3 (gift from Novozymes A/S, Bagsværd, DK) at a loading of 30 mg protein/g glucan for both Ctec3 and HTec3 was added to the hydrolysis reaction. The protein concentrations of the stock enzyme cocktails were quantified as y described in X. Gao, R. Kumar, S. Singh, B. A. Simmons, V. Balan, B. E. Dale and C. E. Wyman, *Biotechnol Biofuels*, 2014, 7, 71, using the Kjeldahl nitrogen analysis method, as described in, for example, R. Kumar and C. E. Wyman, Enzyme Microb Tech, 2008, 42, 426-433. The total volume of the pretreated biomass slurry was adjusted to 10 mL by the addition of deionized water, and the samples were incubated at 50° C. for 72 hrs with orbital shaking at 210 rpm.

Following enzymatic hydrolysis, the solid and liquid phases were separated by centrifugation, and the amount of glucose and xylose released into the aqueous phase was quantified by HPLC (Agilent 1260 Series equipped with an Aminex® HPX-87H column operating at 65° C., a mobile phase of 0.05 M $H_2SO_4$, a flow rate of 0.6 mL/min, and detection using an Agilent 1260 infinity refractive index detector).

The yield of glucose and xylose released was defined as the amount of solubilized monosaccharide divided by the total sugar content of the biomass prior to pretreatment as determined by chemical composition analysis. Prior to each analysis, standard curves were generated using pure solutions of glucose and xylose to convert peak area to concentration of monomeric sugar. The error bars in the figures represent the standard deviation from three or more biological replicates.

Chelating Inorganic Ions from Native Biomass

Biomass (3 g) was mixed with 30 mL of 0.2% (w/v) of the chelator diethylenetriaminepentaacetic acid (DTPA). The pH of the slurry was adjusted to 7.0 with 5 M NaOH, and the solution was incubated for 24 hr at 30° C. The biomass was then washed thoroughly with 10 volumes of distilled $H_2O$ to remove the DTPA, dried at room temperature for 2 days, and stored in airtight bags. Biomass incubated for 24 hr at 30° C. with only distilled water was used as a control.

Pretreatment reactions as described above were performed either in the presence of 2,2'-bipyridine (bpy) plus $Cu^{2+}$, $Mn^{2+}$, or $Fe^{2+}$ ([metal]:[bpy]=2 mM:4 mM) or in the absence of added bpy and metal to ascertain the effect these metal complexes had on the pretreatment of chelated woody biomass. The error bars represent the standard deviation from three or more biological replicates.

Results and Discussion

Different woods are known to respond differently to oxidative pretreatment.[32] To ascertain the key factors that lead to these variations, we analyzed the enzymatic digestibility of four hardwood samples (hybrid poplar, silver birch, aspen, and sugar maple) following alkali-only, AOP, or Cu-AOP pretreatment. Each of these biomass samples had differences in glucan and xylan composition, lignin content and composition, and redox active metal content, and these characteristics were compared with their enzymatic digestibilities following pretreatment.

Cell Wall Composition Analysis

Cell wall composition is an important determinant in the enzymatic digestibility of lignocellulosic biomass, and not surprisingly, analysis of the biomass composition of the four different hardwood samples showed a range of lignin, hemicellulose and cellulose content (See Table 5 below). The amount of glucan varied from 32% to 44%, with the lowest content found in aspen (32%) and the highest in hybrid poplar (44%). Conversely, hybrid poplar had the lowest xylan content at 17%. Importantly, silver birch had the lowest lignin content (18%), while aspen, hybrid poplar, and sugar maple contained roughly equal amounts of lignin (25-26%).

Comparison of Different Alkaline Pretreatments

Figure 27:
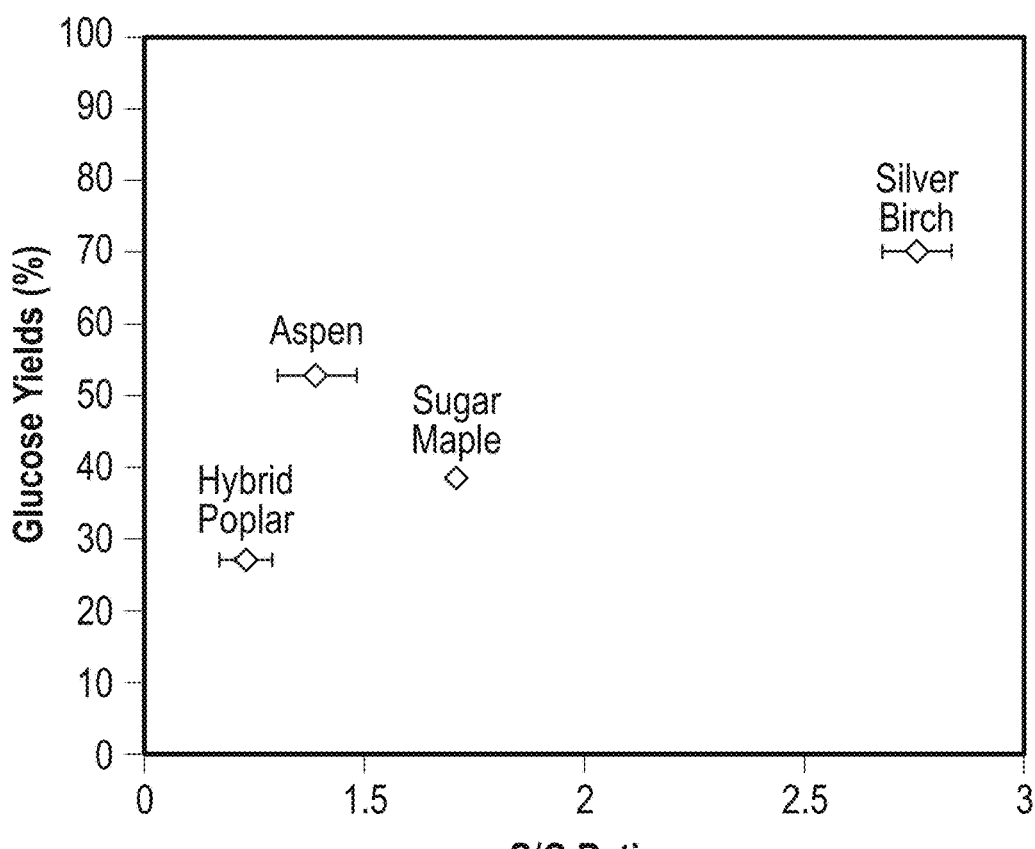
FIG. 27 is a graph showing glucose yield to S/G ratio for various types of hardwood species after undergoing various types of pretreatment processes according to various embodiments.

To ascertain the susceptibility of silver birch, aspen, hybrid poplar, and sugar maple to different alkaline pretreatments, each biomass was subjected to alkali-only, AOP, or Cu-AOP pretreatment followed by enzymatic hydrolysis (FIG. 27 and Table 7). While silver birch and aspen both responded quite well to alkali-only pretreatment, the enzymatic digestibility of hybrid poplar and sugar maple rose much more modestly when only NaOH was used for pretreatment. Intriguingly, while three of the four woody biomass samples tested had very high levels of enzymatic digestibilities following AOP pretreatment and exhibited only a slight increase in digestibility when AOP was performed in the presence of copper 2,2'-bipyridine complexes (Cu-AOP), hybrid poplar behaved quite differently. In the case of hybrid poplar, enzymatic digestibility following alkali-only pretreatment and AOP pretreatment were nearly identical, while glucose yields more than doubled following Cu-AOP pretreatment. Xylose yields demonstrated very similar results (Table 7). Ultimately, silver birch exhibited the highest sugar yields following Cu-AOP and enzymatic hydrolysis (79%), followed by aspen (69%), hybrid poplar (60%), and sugar maple (51%).

TABLE 7

Glucose and xylose yields (%) following enzymatic hydrolysis of alkali, alkaline oxidative peroxide (AOP) and copper catalyzed AOP (Cu-AOP) pretreatment for different biomasses

| Biomass | Alkali | AOP | Cu-AOP |
| --- | --- | --- | --- |
| Glucose yields (%) | | | |
| Silver Birch | 64.2 ± 3.4 | 74.0% ± 2.5 | 80.0 ± 1.1 |
| Aspen | 57.4 ± 5.0 | 63.3 ± 1.4 | 69.0 ± 2.3 |
| Hybrid Poplar | 32.5 ± 1.5 | 28.3 ± 0.2 | 60.6 ± 0.9 |
| Sugar Maple | 33.7 ± 0.3 | 48.7 ± 0.7 | 51.4 ± 0.8 |
| Xylose hydrolysis yields (%) | | | |
| Silver Birch | 75.6 ± 3.9 | 78.12 ± 1.9 | 79.5 ± 1.3 |
| Aspen | 63.7 ± 2.5 | 61.35 ± 0.6 | 62.9 ± 2.1 |
| Hybrid Poplar | 59.5 ± 0.3 | 48.29 ± 0.01 | 74.6 ± 1.4 |
| Sugar Maple | 42.7 ± 0.1 | 56.43 ± 0.7 | 72.8 ± 0.4 |

Figure 26:
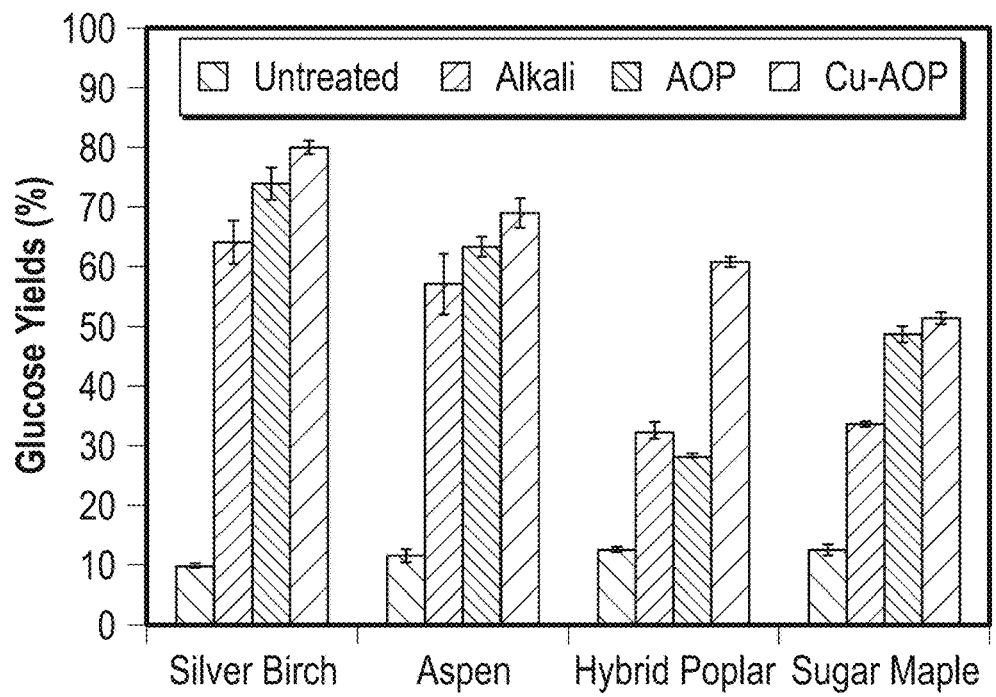
FIG. 26 is a graph showing glucose yields for various hardwood species after undergoing different pretreatments according to various embodiments.

Silver birch, which had the lowest lignin content (Table 5), gave the highest sugar yields following enzymatic digestion (FIG. 26). However, the other three hardwoods all contained approximately the same amount of lignin yet differed significantly their enzymatic digestibility following pretreatment, indicating that there must be other differences between these four biomass samples. FIG. 26 shows glucose yields of various types of wood under various treatment conditions according to various embodiments.

The S/G ratio, which is an important determinant in the extent of lignin crosslinking, is also known to affect biomass recalcitrance. S rich lignin has a less branched structure and lower degree of polymerization than G rich lignin, resulting in S rich lignin generally being more easily removed. In the present study, four different hardwoods were compared, and a correlation was found between the S/G ratio and biomass digestibility FIG. 28). Silver birch, with the lowest lignin content and the highest S/G ratio (2.7), showed highest glucose yields with all pretreatments (Table 5, FIG. 30).

TABLE 5

Compositional analysis of hardwoods used in this study[a]

| Biomass | Glucan (%) | Xylan (%) | Klason Lignin (%) | S/G ratios |
|---|---|---|---|---|
| Silver birch | 39.0 ± 1.9 | 24.2 ± 0.1 | 17.8 ± 0.8 | 2.7 ± 0.1 |
| Aspen | 32.0 ± 1.7 | 20.1 ± 1.0 | 25.0 ± 0.9 | 1.3 ± 0.1 |
| Hybrid poplar | 44.0 ± 1.2 | 17.0 ± 0.2 | 24.6 ± 1.0 | 1.2 ± 0.1 |
| Sugar maple | 42.0 ± 2.0 | 20.0 ± 0.8 | 25.0 ± 2.5 | 1.7 ± 0.1 |

[a]Errors represent standard deviations from either 6 (compositional analysis) or 3 biological replicates.

However, the digestibility of silver birch was only slightly higher than that of aspen even though aspen's S/G ratio was significantly lower (1.3). In addition, sugar maple had the second highest S/G ratio (1.7) and yet resulted in lower glucose yields following enzymatic digestion compared to both silver birch and aspen for all pretreatment tested. Together these results highlight the fact that while lignin content and composition are clearly important, other factors also impact how these four hardwoods respond to different alkali pretreatments.

Redox-Active Metal Content of the Cell Wall

It was noted that the addition of copper 2,2'-bipyridine complexes during AOP pretreatment (Cu-AOP) substantially increased the digestibility of hybrid poplar but only slightly increased the digestibility of the other hardwoods. It was hypothesized that AOP requires the presence of metal ions to be an effective pretreatment for hardwoods. It was further hypothesized that while the silver birch, aspen, and sugar maple samples already contained sufficient redox-active metal ions in their cell wall (thereby obviating the need for the additional copper ions during pretreatment), the hybrid poplar samples contained a relatively low level of redox-active metal ions. In this scenario, the addition of Cu(bpy) complexes during AOP pretreatment would compensate for the low natural levels of metal ions in our hybrid poplar samples.

To test these hypotheses, ICP-MS was performed to quantify cell wall redox-active metal ions in the four different hardwood samples (Table 6).

TABLE 6

ICP-MS analysis for total redox-active metals present in cell wall

| Biomass | Manganese | Iron | Copper | Total[a] |
|---|---|---|---|---|
| Silver birch (control)[b] | 100 | 10 | 1 | 111 ± 5 |
| Silver birch (non chelated)[c] | 98 | 16 | 1 | 115 ± 3 |
| Silver birch (chelated)[d] | 4 | 5 | 1 | 11 ± 2 |
| Aspen (control) | 19 | 26 | 6 | 51 ± 5 |
| Aspen (non chelated) | 16 | 23 | 6 | 45 ± 2 |
| Aspen (chelated) | 2 | 11 | 4 | 17 ± 3 |
| Hybrid poplar (control) | 1 | 5 | 1 | 7 ± 3 |
| Hybrid poplar (non chelated) | 1 | 5 | 1 | 7 ± 2 |
| Hybrid poplar (chelated) | 1 | 2 | 1 | 4 ± 4 |
| Sugar maple (control) | 34 | 10 | 1 | 45 ± 3 |
| Sugar maple (non chelated) | 34 | 6 | 1 | 41 ± 4 |
| Sugar maple (chelated) | 3 | 2 | 1 | 6 ± 3 |

[a]Errors represent the standard deviation from 3 biological replicates
[b]Control samples are untreated biomass.
[c]Non-chelated samples were incubated in pure deionized water for 24 hrs.
[d]Chelated samples were treated with the chelator DTPA for 24 hrs as described in the experimental section.

Figure 28:
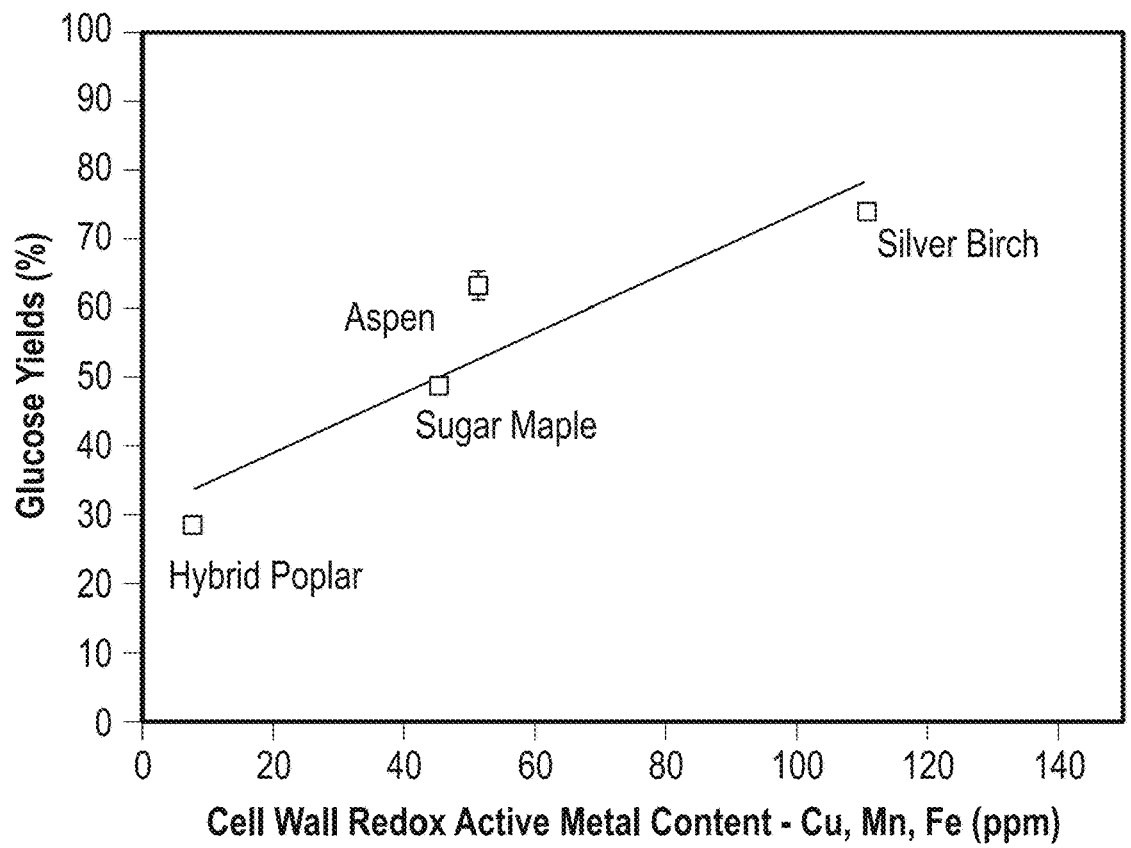
FIG. 28 is a graph showing glucose yield correlation to cell wall redox active metal content for Copper (Cu), Manganese (Mn) and iron (Fe) after undergoing a pretreatment process according to various embodiments.

The values ranged from only 7 ppm found in hybrid poplar to over 110 ppm in silver birch. As predicted, a strong positive correlation was discovered between the redox-active metal content of the woody biomass and enzymatic digestibility following AOP pretreatment (FIG. 28). This same correlation was not observed following Cu-AOP pretreatment. Analysis via ICP-MS of the cell wall metal ion content in Cu-AOP pretreated biomass demonstrated that all samples exhibited a very large increase in the amount of copper relative to the untreated samples, with copper essentially dominating the metal ratio (Table 8).

To corroborate the relationship between intracellular metal content and efficacy of AOP pretreatment, each of the different hard woods was incubated with the metal chelator DTPA prior to pretreatment. CP-MS analysis of the chelated biomass revealed a substantial decrease in metals, with DTPA treatment removing approximately 96% of cell wall redox metals (Table 6).

TABLE 8

ICP-MS concentrations (ppm) for untreated and Cu-AHP, Fe-AHP and Mn-AHP pretreated biomasses

| Biomass | Cu-AHP (Copper) ppm | Fe-AHP (Iron) ppm | Mn-AHP (Manganese) ppm |
|---|---|---|---|
| Silver Birch | 1481 ± 6 | | |
| Aspen | 1238 ± 9 | | |
| Hybrid Poplar | 1182 ± 8 | 619 | 249 |
| Sugar Maple | 1176 ± 9 | | |

Figure 29A:
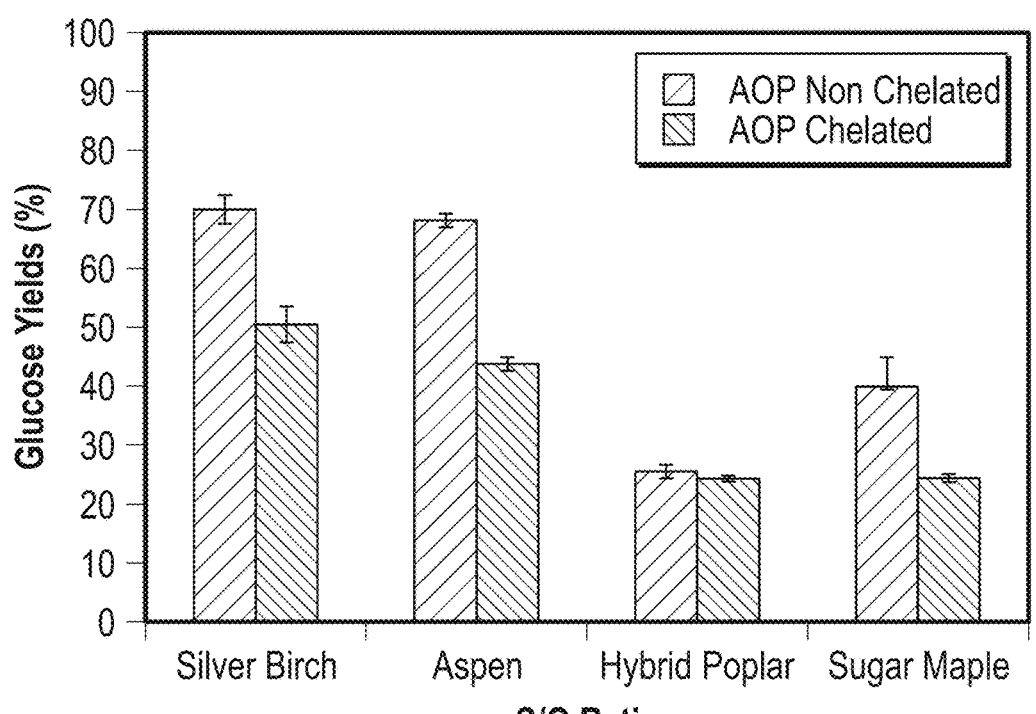
FIGS. 29A-29B is a graph showing glucose yields to S/G ratio for various hardwood species after undergoing an AOP-chelated and AOP-non-chelated pretreatment according to various embodiments.

The effect of chelation was dramatic for biomass that initially contained a large amount of redox-active metal ions. For example, the enzymatic digestibility of chelated silver birch was significantly diminished following uncatalyzed AOP pretreatment relative to biomass that had not been chelated, with glucose yields reduced from 70% to only 50% (FIG. 29A). Likewise, chelated aspen and sugar maple also exhibited lower enzymatic digestibility following uncatalyzed AOP pretreatment relative to unchelated samples. Conversely, the digestibility of hybrid poplar, which naturally had very low cell wall metal content, was not affected by incubation with DTPA.

Figure 29B:
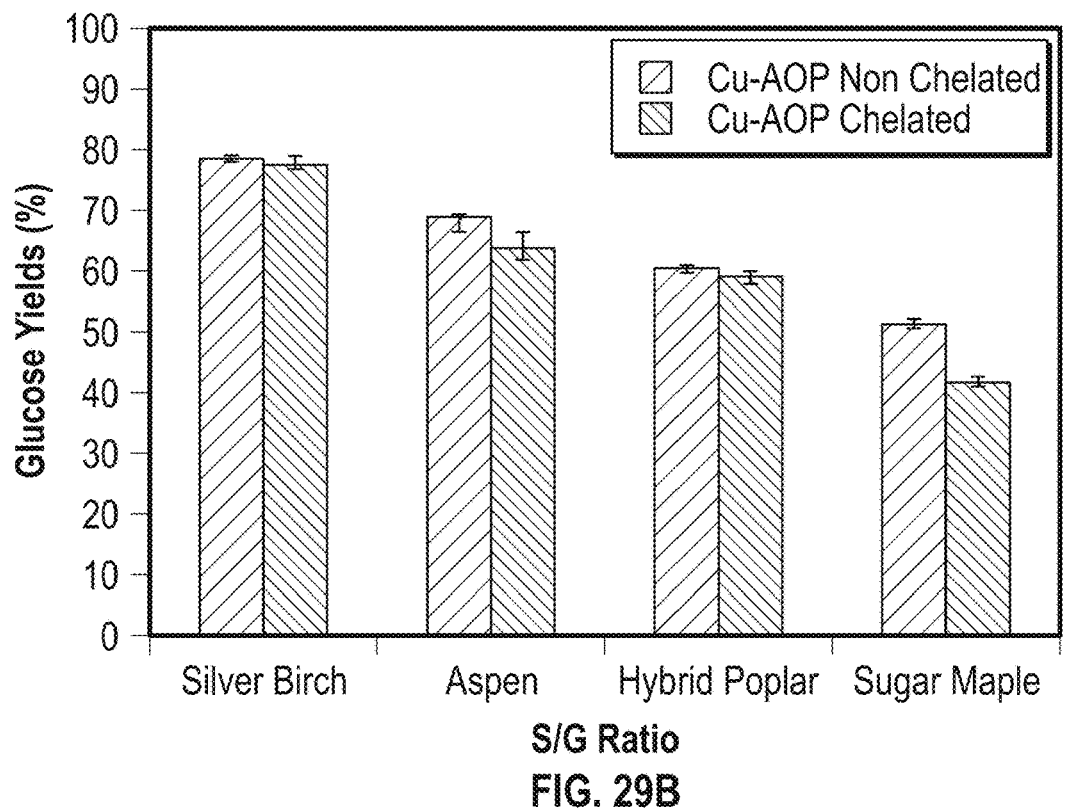
Figure 30:
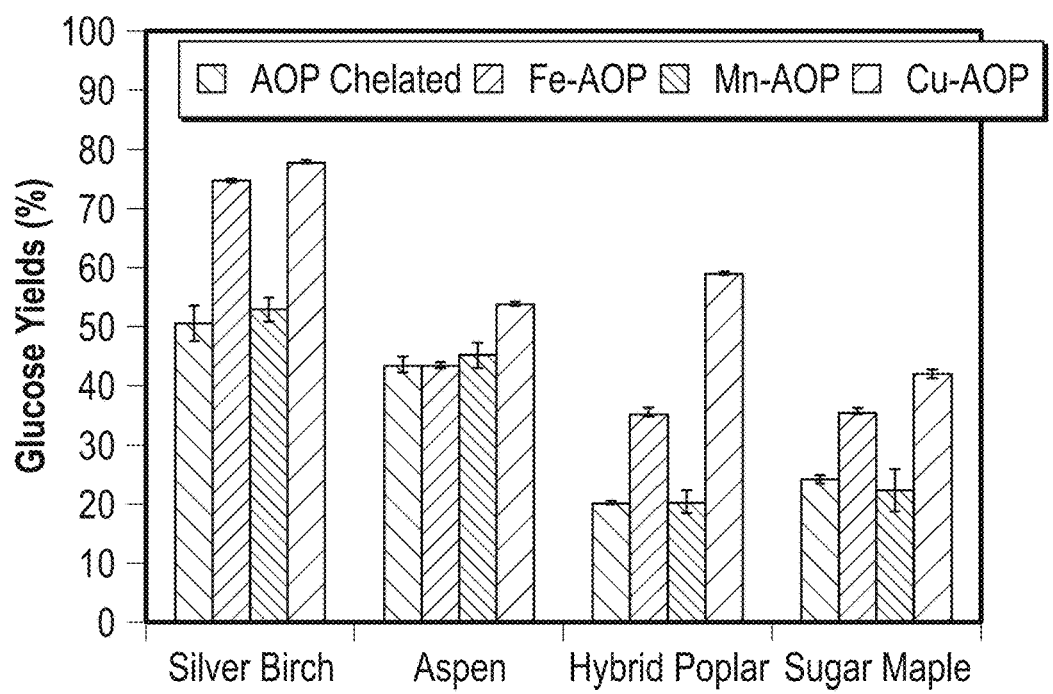
FIG. 30 is a graph showing glucose yields for various hardwood species after undergoing different pretreatments according to various embodiments.

To verify that the decreased efficacy of uncatalyzed AOP following incubation with DTPA was due to the loss of the metal ions, chelated biomass was subjected to metal-catalyzed AOP pretreatment FIG. 29B. As expected, chelation of the hardwoods with DTPA prior to pretreatment did not significantly alter the efficacy of Cu-AOP, presumably because the addition of Cu(bpy) complexes obviated the need for naturally occurring intracellular metal ions. Interestingly, the addition of Cu(bpy) complexes led to significantly higher enzymatic digestibility than the addition of either Mn(bpy) or Fe(bpy) complexes (i.e. Mn-AOP and Fe-AOP) (FIG. 30). Whether this difference is due to the superior reactivity of Cu(bpy) complexes, the result of better penetration of Cu(bpy) complexes into the plant cell wall (Table 8), or some other property cannot be determined from this data.

PROPHETIC EXAMPLES

Testing with other ligands will be performed to determine other candidates for use in the various embodiments described herein.

Recycling of the novel catalysts described herein will also be completed.

Optimization studies will be carried out to further reduce catalyst loading, alkali loading and $H_2O_2$ loading.

Detailed study for lignin degradation products will be conducted to identify lignin removal mechanism.

A detailed study will be conducted to determine sorption behavior of the catalyst for several other biomass fractions. Specifically, we will utilize untreated hybrid poplar as well as hybrid poplar that has been pretreated or pretreated and hydrolyzed, a model cellulose (Avicel®), and a model lignin generated in our lab from the alkali pulping of hybrid poplar. These feedstocks will be used to determine the sorption isotherms of both copper salt (e.g., as $CuSO_4$) and Cu(bpy) (ethylenediamine). The copper content of free liquid will be determined using atomic adsorption spectroscopy in the Chemistry department as employed previously by our group. Additionally, the survival of ligand-metal complexes and their residual catalytic activity following pretreatment will be evaluated using GC-MS, LC-MS and UV/Vis spectrometry.

The recycling of copper catalyst from pretreatment liquors, enzymatic hydrolysates, and clarified (cell-free) stillage following fermentation and distillation using untreated biomass as the bio-sorbent as a strategy to simultaneously detoxify liquors prior to fermentation, to recover catalyst, and to impregnate untreated biomass with catalyst will be further explored. Considering that about 60 to about 70% of the original mass of the biomass is solubilized by pretreatment and hydrolysis, even if the residual biomass strongly adsorbs catalyst, there will be substantially less present. Catalyst recovery will be assessed by analyzing the amount and activity of recovered catalyst as functions of operation parameters including pH, temperature, impregnation time and solids loading.

The feasibility of utilizing polyanionic flocculants and cationic ion exchange resins as a strategy to either remove residual catalyst not recovered by adsorption to untreated biomass or as a standalone recovery strategy will also be explored. Catalyst recovery will be by quantification of copper removal as a function of pH.

In one embodiment, a commercial process for the production of lignocellulose derived sugars is provided. This process can, for example, be converted by biological, chemical, or catalytic conversion to renewable biofuels, biochemicals, and biopolymers. This may function as a standalone pretreatment, or as a component of a multi-stage pretreatment process (as in the case of oxidative bleaching or delignification following alkaline pulping).

The various embodiments further include a homogeneous catalyst (e.g., copper (II) 2,2' bipyridine ethylenediamine (Cu(bpy)en) comprising one or more metals; and at least two metal coordinating ligands, wherein the homogeneous catalyst is a multi-ligand metal complex adapted for use with an oxidant (e.g., air, oxygen, hydrogen peroxide, persulfate, percarbonate and sodium peroxide and/or ozone) in an oxidation reaction to catalytically pretreat lignocellulosic biomass. In one embodiment, the multi-ligand metal complex is a multi-ligand copper complex. In one embodiment, the metals are selected from aluminum, zinc, nickel, magnesium and combinations thereof. In one embodiment, said metals and said metal coordinating ligands are in a state of interaction with each other.

In one embodiment, said metals are selected from Fe(II), Fe(III)), Cu(I), Cu(II), Co(III), Co(VI)), V(II), V(III), V(IV), V(V) and combinations thereof.

In one embodiment, the metal coordinating ligand is selected from pyridine, 1,10-phenanthroline, ethylenediamene, histidine, glycine and combinations thereof.

In one embodiment, the lignocellulosic biomass contains more than trace amounts of at least one transition metal, such as, but not limited to, iron, copper and/or manganese.

In one embodiment, a method of pretreating plant biomass is provided, comprising catalytically pretreating the plant biomass with a multi-ligand metal complex and oxidant in an alkaline oxidative pretreatment to produce a catalytically pretreated plant biomass.

In one embodiment, the plant biomass, the multi-ligand metal complex and the oxidant form a solution having a pH of at least 11.5. In one embodiment, the oxidant is hydrogen peroxide and the multi-ligand metal complex is a multi-ligand copper complex.

In one embodiment, the copper complex is a copper(II) 2,2'-bipyridine complex (Cu(bpy)) modified to contain at least one additional metal-coordinating ligand, such as ethylenediamine.

In one embodiment, the oxidant is added at a gradual rate. In one embodiment, the gradual rate is equal to or less than a rate of consumption of the oxidant by the plant biomass and the multi-ligand metal complex.

In various embodiments, the method can further comprise extracting the lignocellulosic biomass prior to produce a solids fraction and a liquid fraction, wherein the solids fraction is catalytically pretreated and/or recovering and reusing the multi ligand metal complex.

In one embodiment, the catalytic pretreating step also produces a liquid phase and the method further comprises separating the catalytically pretreated biomass from the liquid phase to produce separated catalytically pretreated biomass; and hydrolyzing the separated catalytically pretreated biomass to produce hydrolyzed catalytically pretreated biomass.

All publications, patents and patent documents are incorporated by reference herein, as though individually incorporated by reference, each in their entirety, as though individually incorporated by reference. In the case of any inconsistencies, the present disclosure, including any definitions therein, will prevail.

Although specific embodiments have been illustrated and described herein, it will be appreciated by those of ordinary skill in the art that any procedure that is calculated to achieve the same purpose may be substituted for the specific embodiments shown. For example, although the process has been discussed using particular types of plant biomass, any type of plant biomass, such as grasses, rice straw and the like, for example, may be used. Additionally, although the process has been discussed using primarily copper as the metal in the multi ligand metal catalyst, other metals, such as iron, in various oxidation states, for example, may be used. This application is intended to cover any adaptations or variations of the present subject matter. Therefore, it is manifestly intended that embodiments of this invention be limited only by the claims and the equivalents thereof.

What is claimed is:

1. A method comprising:
catalytically delignifying alkaline-pretreated lignocellulosic biomass having a lignin glass transition temperature by combining the biomass with a homogeneous multi-ligand metal complex catalyst and hydrogen peroxide in an oxidation reaction performed at atmospheric pressure and at a temperature below the lignin glass transition temperature, wherein the hydrogen peroxide is added at a rate equal to or less than a rate of consumption of the hydrogen peroxide by said biomass and the complex catalyst, further wherein a weight ratio of the hydrogen peroxide to biomass loading is less than 15% and said metal complex catalyst comprises a combination of a metal-ligand complex and at least one metal coordinating ligand selected from pyridine, 1,10-phenanthroline, ethylenediamene, histidine, glycine and combinations thereof, wherein said biomass, the multi-ligand complex catalyst and the hydrogen peroxide form a solution having a pH of at least 11, and radicals formed during the oxidation reaction react with lignin present in the alkaline-pretreated lignocellulosic biomass to solubilize the lignin to produce catalytically delignified lignocellulosic biomass, wherein the multi-ligand metal complex catalyst is a multi-ligand copper complex catalyst.

2. The method of claim 1 wherein the alkaline-pretreated lignocellulosic biomass, the multi-ligand metal complex catalyst and the hydrogen peroxide form a solution having a pH of at least 11.5.

3. The method of claim 2 wherein the radicals formed during the oxidation reaction are hydroxyl radicals.

4. The method of claim 3 wherein the copper complex catalyst is a copper(II) 2,2'-bipyridine complex (Cu(bpy)) catalyst modified to contain at least one additional metal-coordinating ligand.

5. The method of claim 4 wherein said additional metal-coordinating ligand is ethylenediamine.

6. The method of claim 1 wherein the hydrogen peroxide is added at a gradual rate equal to or less than a rate of consumption of the hydrogen peroxide by the alkaline-pretreated lignocellulosic biomass and the multi-ligand metal complex catalyst.

7. The method of claim 1 wherein the method further comprises extracting the alkaline-pretreated lignocellulosic biomass prior to producing a solids fraction and a liquid fraction, wherein the solids fraction is catalytically delignified.

8. The method of claim 1 wherein the method further comprises recovering and reusing the multi-ligand metal complex catalyst.

9. The method of claim 1 wherein the catalytically delignifying step also produces a liquid phase and the method further comprises:
separating the catalytically delignified biomass from the liquid phase to produce separated catalytically delignified biomass; and
hydrolyzing the separated catalytically delignified biomass to produce hydrolyzed catalytically delignified biomass.

10. The method of claim 1 wherein the multi-ligand metal complex catalyst contains metal elements selected from aluminum, zinc, nickel, magnesium and combinations thereof.

11. The method of claim 1 wherein the multi-ligand metal complex catalyst contains metal elements selected from Fe(II), Fe(III)), Cu(I), Cu(II), Co(III), Co(VI)), V(II), V(III), V(IV), V(V) and combinations thereof.

12. The method of claim 1 wherein the alkaline-pretreated lignocellulosic biomass contains more than trace amounts of at least one transition metal.

13. The method of claim 12 wherein the transition metal is selected from at least one of iron, copper, and manganese.

14. The method of claim 1 wherein the alkaline-pretreated lignocellulosic biomass also contains hemicellulose and the alkaline pretreatment removes a portion of the hemicellulose and lignin.

15. The method of claim 1 wherein a hydrogen peroxide to biomass loading ratio is from about 1% to less than 10%.

16. The method of claim 4 wherein the Cu(bpy)en contains substantially equal amounts of cupric sulfate pentahydrate, bipyridine and ethylenediamine in an aqueous solution.

17. The method of claim 1, wherein the metal-ligand complex in the multi-ligand metal complex catalyst comprises less than 50 µmol of metal complex per gram of the alkaline-pretreated lignocellulosic biomass and the oxidant comprises less than 10% by weight of the alkaline-pretreated lignocellulosic biomass.

18. The method of claim 1 wherein the alkaline pretreated lignocellulosic biomass has a cell wall matrix with nano-scale pores into which the multi-ligand metal complex catalyst diffuses.

19. The method of claim 1 wherein the temperature is room temperature.

20. The method of claim 1 wherein the hydrogen peroxide is added over at least about a two hour period.

* * * * *